(12) United States Patent
Finlay et al.

(10) Patent No.: US 11,136,340 B2
(45) Date of Patent: *Oct. 5, 2021

(54) AMINO-TRIAZOLOPYRIDINE COMPOUNDS AND THEIR USE IN TREATING CANCER

(71) Applicant: AstraZeneca AB, Södertälje (SE)

(72) Inventors: Maurice Raymond Verschoyle Finlay, Cambridge (GB); Frederick Woolf Goldberg, Cambridge (GB); Attilla Kuan Tsuei Ting, Cambridge (GB)

(73) Assignee: AstraZeneca AB, Södertälje (SE)

( * ) Notice: Subject to any disclaimer, the term of this patent is extended or adjusted under 35 U.S.C. 154(b) by 152 days.

This patent is subject to a terminal disclaimer.

(21) Appl. No.: 16/526,219

(22) Filed: Jul. 30, 2019

(65) Prior Publication Data

US 2020/0048281 A1 Feb. 13, 2020

Related U.S. Application Data

(63) Continuation of application No. 15/846,679, filed on Dec. 19, 2017, now Pat. No. 10,407,446.

(60) Provisional application No. 62/436,619, filed on Dec. 20, 2016.

(51) Int. Cl.
| | |
|---|---|
| A61K 31/522 | (2006.01) |
| A61P 35/00 | (2006.01) |
| C07D 519/00 | (2006.01) |
| C07D 473/18 | (2006.01) |
| A61K 31/502 | (2006.01) |
| A61K 45/06 | (2006.01) |

(52) U.S. Cl.
CPC .......... *C07D 519/00* (2013.01); *A61K 31/502* (2013.01); *A61K 31/522* (2013.01); *A61K 45/06* (2013.01); *A61P 35/00* (2018.01); *C07D 473/18* (2013.01)

(58) Field of Classification Search
CPC ............................. A61K 31/522; A61P 35/00
USPC .................................................. 514/263.22
See application file for complete search history.

(56) References Cited

U.S. PATENT DOCUMENTS

| | | | |
|---|---|---|---|
| 6,432,947 | B1 | 8/2002 | Arnaiz et al. |
| 7,902,187 | B2 | 3/2011 | Neagu et al. |
| 8,436,004 | B2 | 5/2013 | Bamba et al. |
| 10,407,446 | B2 | 9/2019 | Finlay et al. |
| 2007/0191447 | A1 | 8/2007 | Kodo et al. |
| 2011/0135601 | A1 | 6/2011 | Bamba |
| 2013/0245029 | A1 | 9/2013 | Xu et al. |

FOREIGN PATENT DOCUMENTS

| | | |
|---|---|---|
| AR | 086196 A1 | 11/2013 |
| CN | 102675897 A | 9/2012 |
| CN | 103864792 A | 6/2014 |
| EP | 1888578 A1 | 11/2006 |
| EP | 2527344 A1 | 11/2012 |
| JP | 2012-500805 A | 1/2012 |
| JP | 2013032343 A | 2/2013 |
| WO | WO2005023761 A2 | 3/2005 |
| WO | WO2006122806 A2 | 11/2006 |
| WO | WO2007035873 A1 | 3/2007 |
| WO | WO2007042299 A1 | 4/2007 |
| WO | WO2007058990 A2 | 5/2007 |
| WO | WO2006074985 A1 | 7/2007 |
| WO | WO2005080334 A1 | 8/2007 |
| WO | WO2007140222 A2 | 12/2007 |
| WO | WO2007146712 A2 | 12/2007 |
| WO | WO2008043031 A1 | 4/2008 |
| WO | WO2008051493 A1 | 5/2008 |
| WO | WO2009024824 A1 | 2/2009 |
| WO | WO2009122180 A1 | 10/2009 |
| WO | WO2008153207 A1 | 8/2010 |
| WO | WO2011016472 A1 | 2/2011 |
| WO | WO2011082337 A1 | 7/2011 |

(Continued)

OTHER PUBLICATIONS

An, et al., "DNA-PKcs plays a dominant role in the regulation of H2AX phosphorylation in response to DNA damage and cell cycle progression", BMC Mol. Biol. 11:18 (2010).

(Continued)

*Primary Examiner* — Raymond J Henley, III

(57) ABSTRACT

The specification generally relates to compounds of Formula (I):

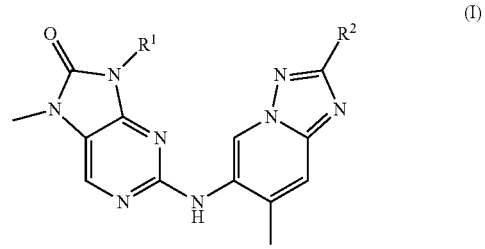

and pharmaceutically acceptable salts thereof, where $R^1$ and $R^2$ have any of the meanings defined herein. The specification also relates to the use of such compounds and salts thereof to treat or prevent DNA-PK mediated disease, including cancer. The specification further relates to pharmaceutical compositions comprising such compounds and salts; kits comprising such compounds and salts; methods of manufacture of such compounds and salts; intermediates useful in the manufacture of such compounds and salts; and to methods of treating DNA-PK mediated disease, including cancer, using such compounds and salts.

28 Claims, 7 Drawing Sheets

(56) References Cited

FOREIGN PATENT DOCUMENTS

| WO | WO2011097333 A1 | 8/2011 |
| WO | WO2011130232 A1 | 11/2011 |
| WO | WO2012143143 A1 | 10/2012 |
| WO | WO2012160030 A1 | 11/2012 |
| WO | WO2013059396 A2 | 4/2013 |
| WO | WO2014134240 A1 | 9/2014 |
| WO | WO2015170081 A1 | 11/2015 |

OTHER PUBLICATIONS

Ashley, et al., "DNA-PK phosphorylation of RPA32 Ser4/Ser8 regulates replication stress checkpoint activation, fork restart, homologous recombination and mitotic catastrophe", DNA Repair 21 (2014), pp. 131-139.

Buisson, et al., "Distinct but concerted roles of ATR, DNA-PK and Chk1 in countering replication stress during S phase", Molecular Cell 59 (2015), pp. 1011-1024.

Chan, et al., "Autophosphorylation of the DNA-dependent protein kinase catalytic subunit is required for rejoining of DNA double-strand breaks", Genes Dev 16 (2002), pp. 2333-2338.

Ciszewski, et al., "DNA-PK inhibition by NU7441 sensitizes breast cancer cells to ionizing radiation and doxorubicin", Breast Cancer Res. Treat. 143 (2014), pp. 47-55.

Dietlein, et al., "A functional cancer genomics screen identifies a druggable synthetic lethal interaction between MSH3 and PRKDC", Cancer Discovery 4:5 (2014), pp. 592-605.

Douglas, et al., "Identification of in vitro and in vivo phosphorylation sites in the catalytic subunit of the DNA-dependent protein kinase", Biochem J. 368 (2002), pp. 243-251.

Escribano-Diaz, et al., "A cell cycle-dependent regulatory circuit composed of 53BP1-RIF1 and BRCA1-CtIP controls DNA repair pathway choice", Mol. Cell 49 (2013), pp. 872-883.

Goodwin, et al., "Beyond DNA repair: DNA-PK function in cancer", Cancer Discovery 4:10 (2014), pp. 1126-1139.

Goodwin, et al., "A hormone-DNA repair circuit governs the response to genotoxic insult", Cancer Discovery 3:11 (2013), pp. 1254-1271.

Hartlerode, et al., "Mechanisms of double-strand break repair in somatic mammalian cells", Biochem J. 423 (2009), pp. 157-168.

Hartlerode, et al., "Mechanisms of double-strand break repair in somatic mammalian cells", Biochem J. 426 (2010), p. 389.

Huang, et al., "Approaching the active conformation of 1,3-diaminopyrimidine based covalent inhibitors of Bruton's tyrosine kinase for treatment of Rheumatoid arthritis", Bioorganic & Medicinal Chemistry Letters 26 (2016), pp. 1954-1957.

Lack, et al., "Targeting the Binding Function 3 (BF3) Site of the Human Androgen Receptor through Virtual Screening", J. Med. Chem. 54 (2011), pp. 8563-8573.

Lin, et al., "DNA-PKcs is required to maintain stability of Chk1 and claspin for optimal replication stress response", Nucleic Acids Res. 42:7 (2014), pp. 4463-4473.

Medunjanin, et al., "Interaction of the double-strand break repair kinase DNA-PK and estrogen receptor-α", Mol. Biol. of the Cell 21 (2010), pp. 1620-1628.

Munck, et al., "Chemosensitization of cancer cells by KU-0060648, a dual inhibitor of DNA-PK and PI-3K", Mol. Cancer Ther. 11:8 (2012), pp. 1789-1798.

Neal, et al., "Choosing the right path: does DNA-PK help make the decision?", Mutation Res 711 (2011), pp. 73-86.

Riabinska, et al., "Therapeutic targeting of a robust non-oncogene addiction to PRKDC in ATM-defective tumors", Science Translational Medicine 5:189 (2013), pp. 1-11.

San Filippo, et al., "Mechanism of eukaryotic homologous recombination", Annu. Rev. Biochem. 77 (2008), pp. 229-257.

Shao, et al., "Synthesis and SAR studies of trisubstituted purinones as potent and selective adenosine $A_{2A}$ receptor antagonists", Bioorganic & Medicinal Chemistry Letters 19 (2009), pp. 1399-1402.

Smith, et al., "The DNA-dependent protein kinase", Genes and Development 13 (1999), pp. 916-934.

Symington, et al., "Double-strand break end resection and repair pathway choice", Annu. Rev. Genet. 45 (2011), pp. 247-271.

Willmore, et al., "A novel DNA-dependent protein kinase inhibitor, NU7026, potentiates the cytotoxicity of topoisomerase II poisons used in the treatment of leukemia", Blood 103:12 (2004), pp. 4659-4665.

Wu, et al., "Cyclic thiourea/urea functionalized triphenylamine-based dyes for high-performance dye-sensitized solar cells", Organic Letters 15:7 (2013), pp. 1456-1459.

Yngve, et al., "Triazolopyrimidinones as γ-secretase modulators: structure-activity relationship, modulator profile, and in vivo profiling", Med. Chem. Commun. 4 (2013), pp. 422-431.

Yoo, et al., "Geometry of a complex formed by double strand break repair proteins at a single DNA end: recruitment of DNA-PKcs induces inward translocation of Ku protein", Nucleic Acids Res. 27:24 (1999), pp. 4679-4686.

International Search Report and Written Opinion for PCT/EP2017/083625 dated Apr. 19, 2018.

MedicineNet.com (2004) Web:<http://www.medterms.com>.

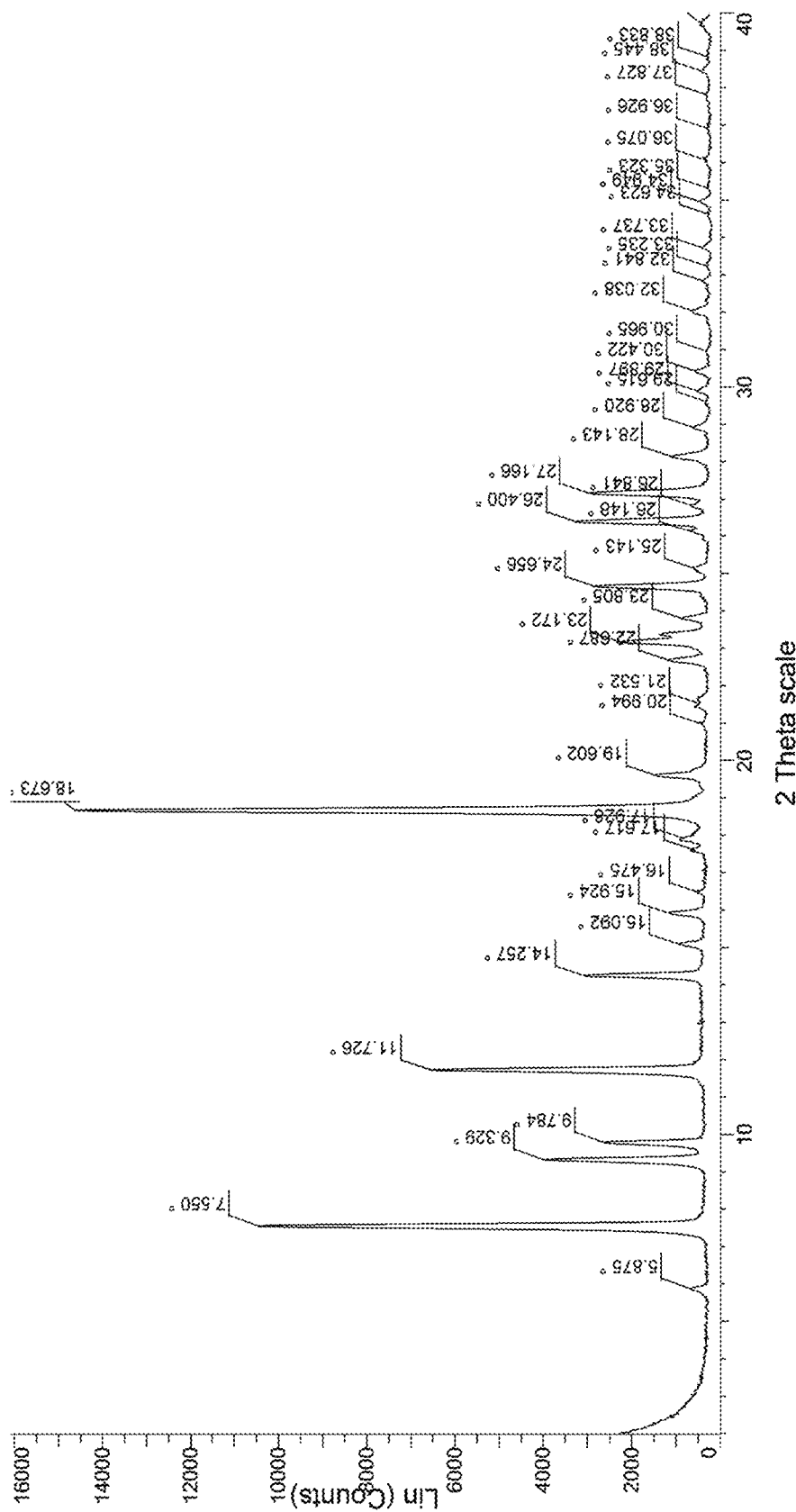
Figure 1: X-Ray Powder Diffraction Pattern of Compound A Form A

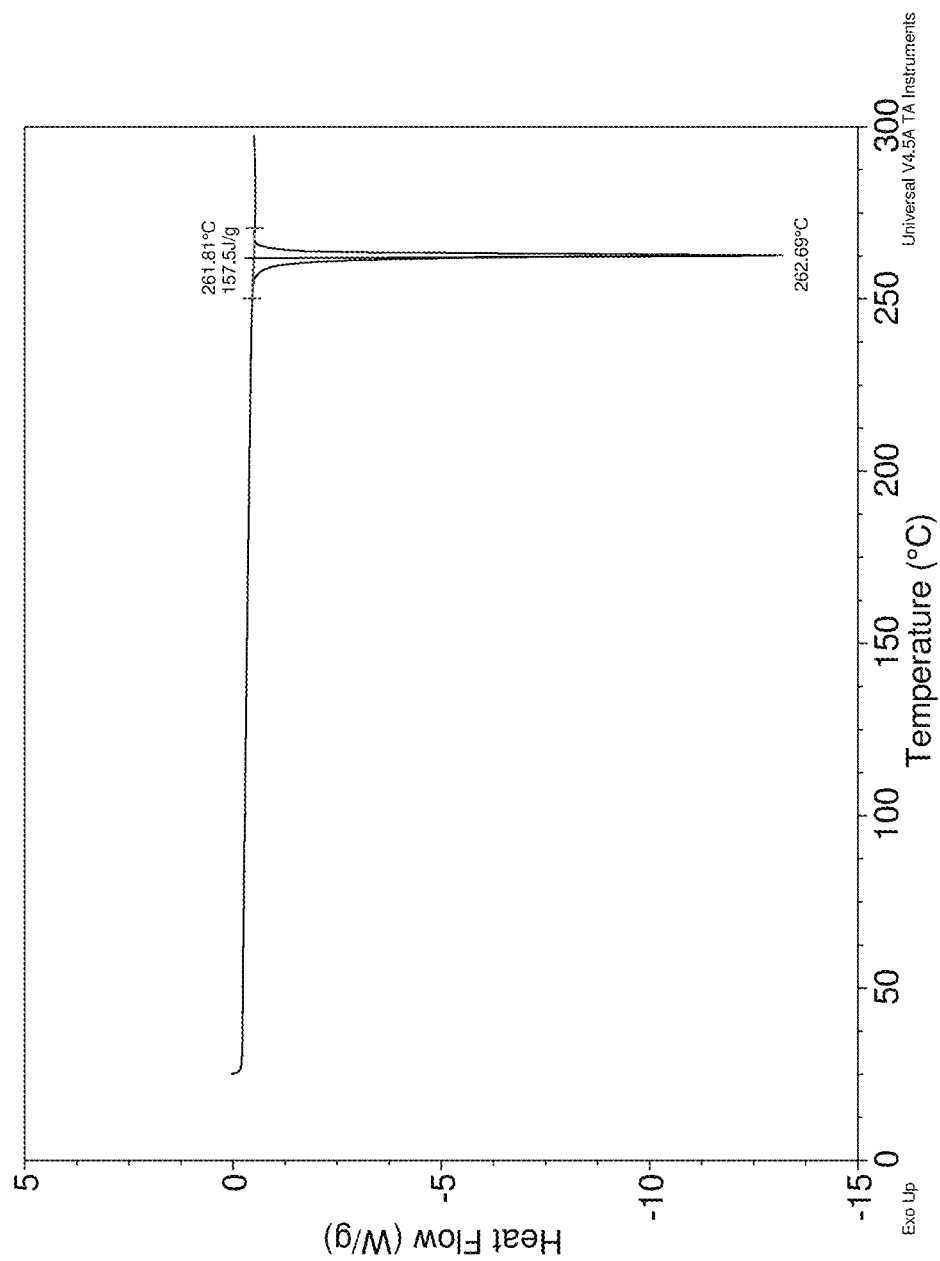
Figure 2: DSC thermogram of Compound A Form A

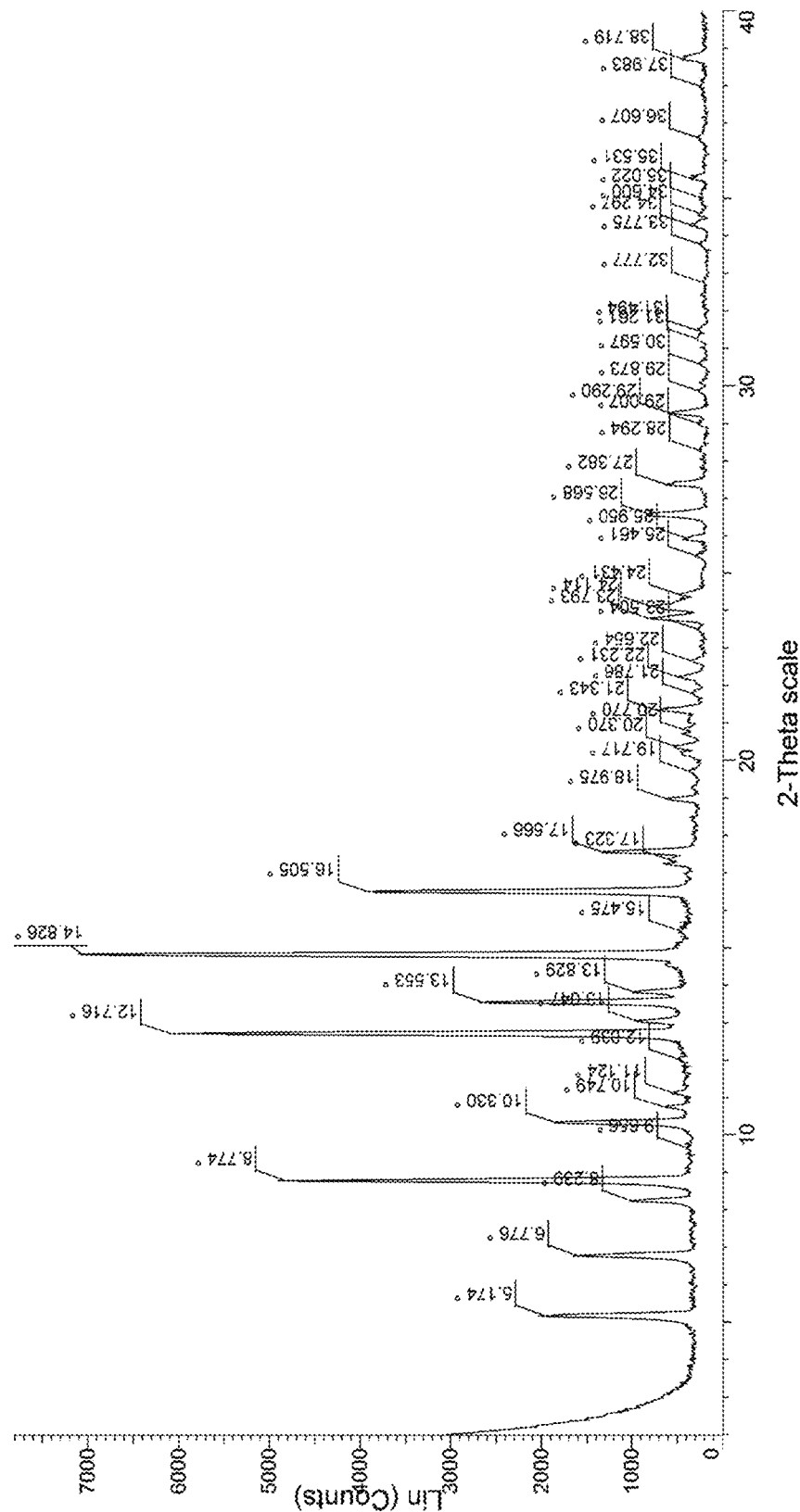
Figure 3: X-Ray Powder Diffraction Pattern of Compound B Form A

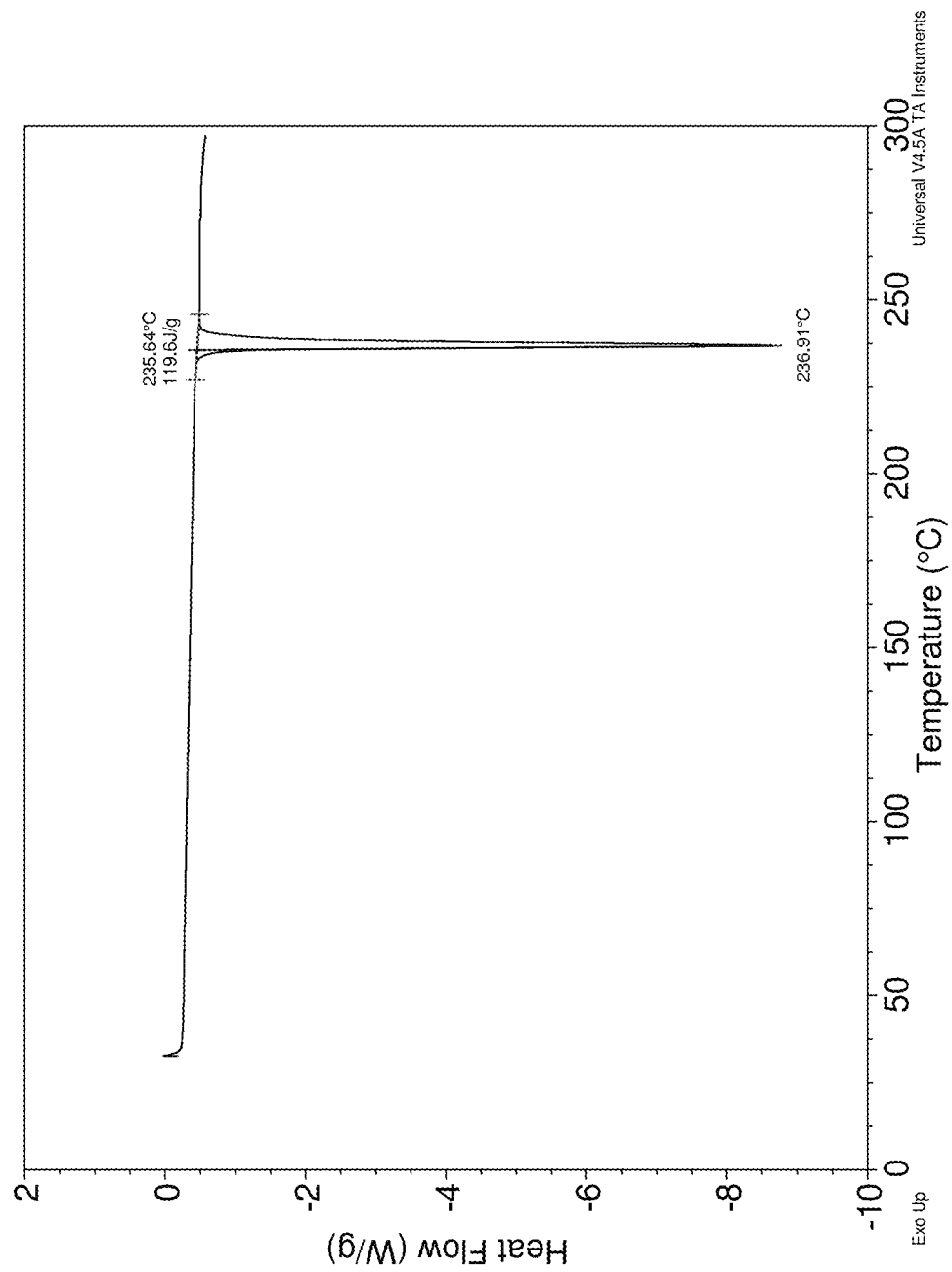
Figure 4: DSC thermogram of Compound B Form A

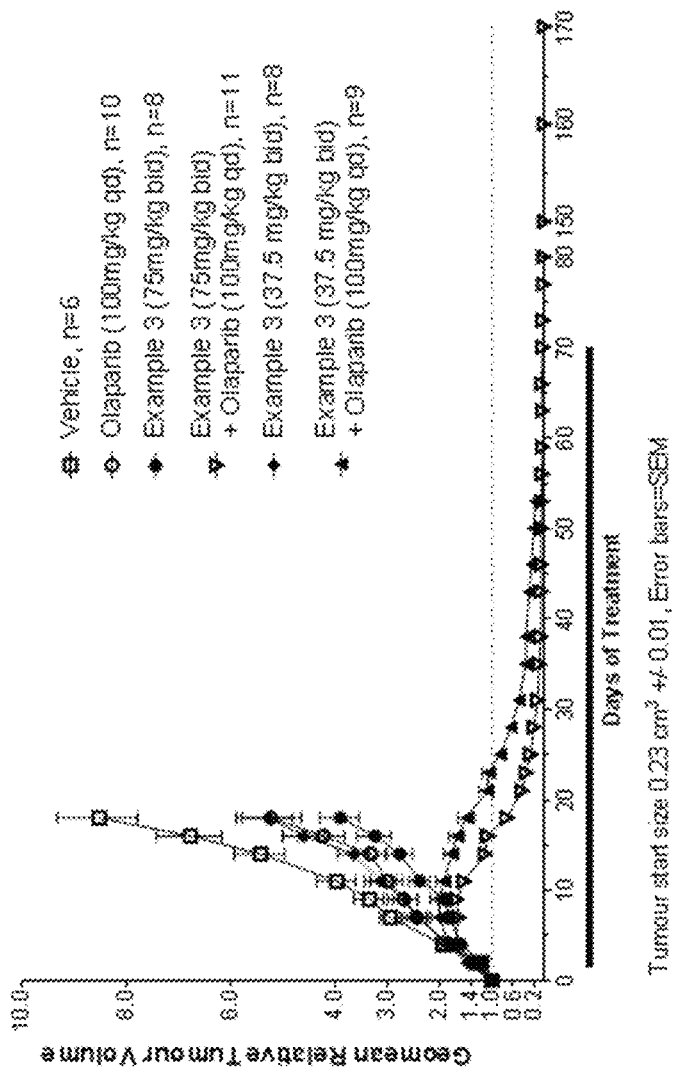
Figure 5: Tumour Growth Inhibition in Mouse Xenograft Model by Example 3 (Compound A) in Combination with Olaparib

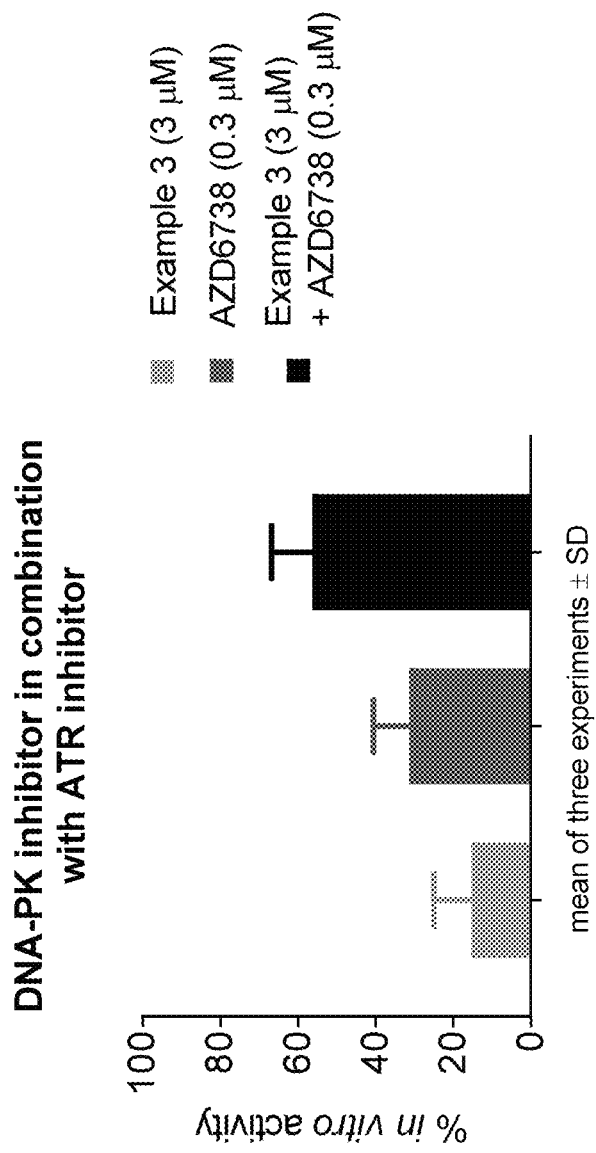
Figure 6: *In Vitro* Activity of Example 3 (Compound A) in Combination with AZD6738, an ATR inhibitor

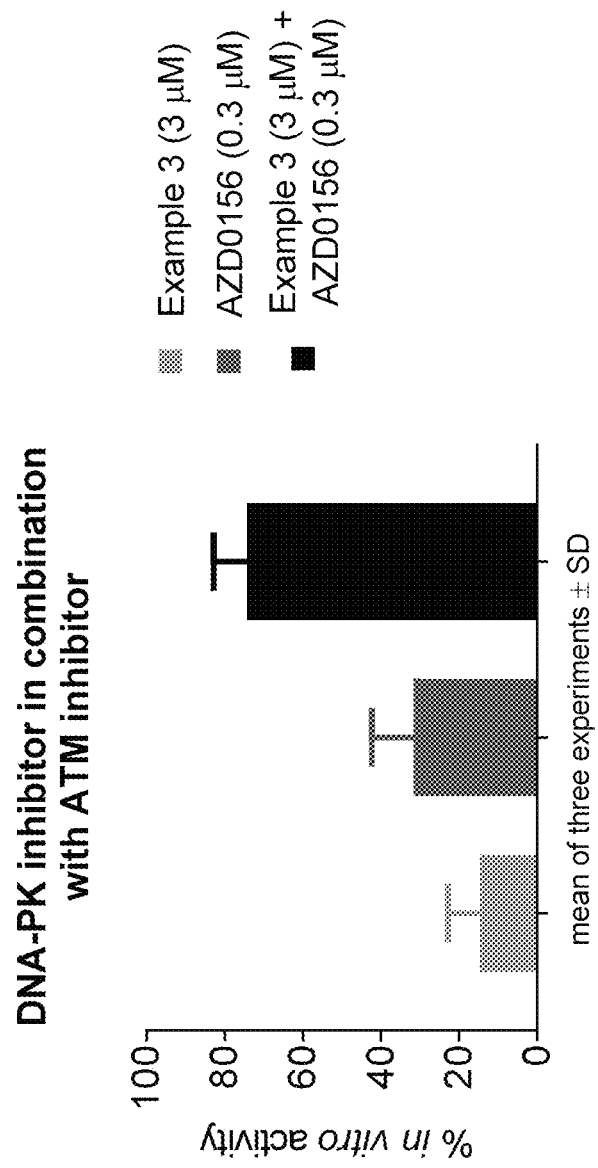
Figure 7: *In vitro* Activity of Example 3 (Compound A) in Combination with AZD0156, an ATM inhibitor

AMINO-TRIAZOLOPYRIDINE COMPOUNDS AND THEIR USE IN TREATING CANCER

CROSS REFERENCE TO RELATED APPLICATIONS

This application is a Continuation of U.S. application Ser. No. 15/846,679, filed Dec. 19, 2017, now U.S. Pat. No. 10,407,446; said application Ser. No. 15/846,679 claims the benefit under 35 U.S.C. § 119(e) of U.S. Provisional Application No. 62/436,619 filed on Dec. 20, 2016 all of which are incorporated by reference herein in their entirety for all purposes.

FIELD OF INVENTION

The specification generally relates to substituted amino-triazolopyridines compounds and pharmaceutically acceptable salts thereof. These compounds and their pharmaceutically acceptable salts selectively modulate DNA-dependent protein kinase ("DNA-PK"), and the specification therefore also relates to the use of such compounds and salts thereof to treat or prevent DNA-PK mediated disease, including cancer. The specification further relates to crystalline forms of compounds of substituted amino-triazolopyridine compounds and pharmaceutically acceptable salts thereof; pharmaceutical compositions comprising such compounds and salts; kits comprising such compounds and salts; methods of manufacture of such compounds and salts; intermediates useful in the manufacture of such compounds and salts; and to methods of treating DNA-PK mediated disease, including cancer, using such compounds and salts.

BACKGROUND

DNA-PK is a nuclear serine/threonine protein kinase complex composed of the catalytic subunit DNA-PKcs and a heterodimer of Ku proteins (Ku70/Ku80). DNA-PK plays a crucial role in the repair of DNA double strand breaks (DSBs), serving to maintain genomic integrity, and in the process of V(D)J recombination, resulting in the highly diverse repertoire of antibodies/immunoglobulins and T cell receptors found on B- and T-cells respectively. DNA-PK has also been implicated in a range of other biological processes, including modulation of chromatin structure, telomere maintenance, transcriptional regulation, and the response to replication stress (Smith and Jackson, 1999; Goodwin and Knudsen, 2014).

DNA DSBs are regarded as the most lethal lesion a cell can encounter. To combat the serious threats posed by DNA DSBs, eukaryotic cells have evolved several mechanisms to mediate their repair. In higher eukaryotes, the predominant mechanism is DNA non-homologous end-joining (NHEJ). This is an error-prone DSB repair pathway involving direct ligation of the broken ends of DSBs that occurs during all phases of the cell cycle, and is preferentially used during the early G1/S phases, where no template sister chromatid is available (Hartlerode and Scully, 2009). This is in contrast to the second major pathway of DSB repair, homologous recombination (HR), which occurs primarily in G2/M phases of the cell cycle when undamaged sister chromatids are available (San Filippo et al., 2008). Other mechanisms underlying the selection of NHEJ or HR for DSB repair are incompletely defined, although blunt, minimally processed DNA ends are repaired by NHEJ, whereas 3' end resection is required for HR to occur (Symington and Gautier, 2011). End resection is controlled by an interplay of BRCA1 and 53BP1, with 53BP1 supporting NHEJ by suppressing end resection (Escribano-Diaz et al., 2013).

NHEJ is initiated through the recognition and binding of broken DNA ends by the ring-shaped Ku70/Ku80 heterodimer, followed by recruitment of DNA-PKcs through its interaction with Ku and DNA. Recruitment of DNA-PKcs facilitates movement of the Ku heterodimer into the DNA duplex, allowing DNA-PKcs to serve as a tether for the broken DNA ends and prevent degradation by exonucleases (Yoo and Dynan, 1999). Binding to DNA promotes activation of DNA-PKcs catalytic activity. Perhaps the most important substrate of DNA-PK is the kinase subunit itself, as autophosphorylation is critical for the regulation of DNA end processing, enzyme inactivation and complex dissociation (Chan et al., 2002). The most well characterized autophosphorylation sites are Ser2056 and Thr2609 (Douglas et al., 2002). DNA-PKcs phosphorylates and alters the activity of a wide range of substrates that mediate NHEJ, including Artemis, Ku70, Ku80, and DNA ligase 4 (Neal and Meek, 2011); it also phosphorylates Ser139 on histone variant H2AX (γH2AX); this is a well known marker of DNA double strand breaks (An et al., 2010).

Double strand breaks can be generated endogenously via production of reactive oxygen species during metabolism or via developmental V(D)J recombination in the immune system, and exogenously by ionizing radiation, radiomimetic drugs such as bleomycin, and topoisomerise II inhibitors such as etoposide and doxorubicin. Therefore, DNA-PK inhibitors are likely to increase the lethality of these agents. DNA-PK inhibitors may also be effective as single agents in tumours with high endogenous levels of DNA damage resulting from defects in other DNA repair pathways such as HR and mismatch repair. For example, DNA-PK inhibitors have been shown to be effective as single agents against ATM defective lymphomas (Riabinska et al., 2013). ATM is important in HR repair, and when cancer cells are deficient in ATM the cells are "addicted" to NHEJ to enable their survival. A synthetic lethal interaction has also been demonstrated between DNA-PK and MSH3 (Deitlein et al., 2014). DNA-PK is a member of the phosphatidylinositol 3-kinase-related kinase (PIKK) family of protein kinases and older generation DNA-PK inhibitors such as NU7026, NU7441, KU-0060648 and CC-115 have suffered from poor selectivity against other PIKK family members. However, these compounds have demonstrated the therapeutic potential of targeting DNA-PK consistent with the known mechanisms of action of the DNA-PK protein. For example, NU7026 and KU-0060648 can potentiate the cytotoxicity of topoisomerase II inhibitors (Willmore et al, 2004; Munck et al., 2012) and NU7441 potentiated the effect of ionizing radiation in breast cancer models (Ciszewski et al., 2014). Other applications of DNA-PK inhibitors in oncology could include targeting tumours with high levels of replication stress (Lin et al., 2014; Ashley et al., 2014; Buisson et al., 2015), either as a monotherapy or in combination with other agents such as Wee 1, ATR or CHK inhibitors, or as a combination therapy with endocrine agents in prostate (Goodwin et al., 2013) and breast (Medunjanin et al., 2010) cancers.

Accordingly there is a need for DNA-PK inhibitors that are selective, demonstrate good bioavailability and are suitable for dosing.

SUMMARY OF INVENTION

Briefly, this specification describes, in part, a compound of Formula (I):

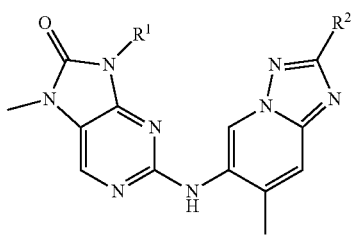

or a pharmaceutically acceptable salt thereof, where:

R¹ is a cyclohexyl, tetrahydrofuranyl or oxanyl ring, each of which is optionally substituted by one or more groups selected from hydroxyl, methoxy and methyl; and R² is hydrogen or methyl.

This specification also describes, in part, a pharmaceutical composition which comprises a compound of Formula (I), or a pharmaceutically acceptable salt thereof, and at least one pharmaceutically acceptable diluent or carrier.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of cancer.

This specification also describes, in part, a compound of Formula (I), or a pharmaceutically acceptable salt thereof, for the manufacture of a medicament for the treatment of cancer.

This specification also describes, in part, a method for treating cancer in a warm blooded animal in need of such treatment, which comprises administering to said warm-blooded animal a therapeutically effective amount of a compound of Formula (I), or a pharmaceutically acceptable salt thereof.

BRIEF DESCRIPTION OF THE FIGURES

FIG. 1 shows the XRPD for Form A of 7-methyl-2-((7-methyl-[1,2,4]triazolo[1,5-a]pyridin-6-yl)amino)-9-(tetrahydro-2H-pyran-4-yl)-7,9-dihydro-8H-purin-8-one (Compound A, Example 3).

FIG. 2 shows the DSC for Form A of 7-methyl-2-((7-methyl-[1,2,4]triazolo[1,5-a]pyridin-6-yl)amino)-9-(tetrahydro-2H-pyran-4-yl)-7,9-dihydro-8H-purin-8-one (Compound A, Example 3).

FIG. 3 shows the XRPD for Form A of 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one (Compound B, Example 10).

FIG. 4 shows the DSC for Form A of 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one (Compound B, Example 10).

FIG. 5 shows Tumour Growth Inhibition in the Mouse Xenograft Model by 7-methyl-2-((7-methyl-[1,2,4]triazolo[1,5-a]pyridin-6-yl)amino)-9-(tetrahydro-2H-pyran-4-yl)-7,9-dihydro-8H-purin-8-one (Compound A, Example 3) in Combination with Olaparib.

FIG. 6 shows In vitro Activity of 7-methyl-2-((7-methyl-[1,2,4]triazolo[1,5-a]pyridin-6-yl)amino)-9-(tetrahydro-2H-pyran-4-yl)-7,9-dihydro-8H-purin-8-one (Compound A, Example 3) in Combination with AZD6738, an ATR inhibitor.

FIG. 7 shows In vitro Activity of 7-methyl-2-((7-methyl-[1,2,4]triazolo[1,5-a]pyridin-6-yl)amino)-9-(tetrahydro-2H-pyran-4-yl)-7,9-dihydro-8H-purin-8-one (Compound A, Example 3) in Combination with AZD0156, an ATM inhibitor.

DESCRIPTION OF ILLUSTRATIVE EMBODIMENTS

Many embodiments of the invention are detailed throughout the specification and will be apparent to a reader skilled in the art. The invention is not to be interpreted as being limited to any particular embodiment(s) thereof.

In the first embodiment there is provided a compound of Formula (I):

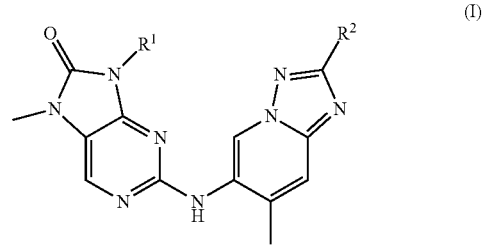

or a pharmaceutically acceptable salt thereof, where:

R¹ is a cyclohexyl, tetrahydrofuranyl or oxanyl ring, each of which is optionally substituted by one or more groups selected from hydroxyl, methoxy and methyl, and R² is hydrogen or methyl.

The term "cyclohexyl ring" refers to carbocyclic ring containing six carbon atoms and no heteroatoms. 1-methoxycyclohex-4-yl groups and 4-methoxycyclohex-1-yl groups have the same structure, as shown below.

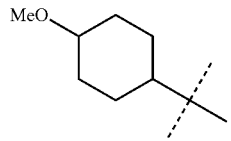

A cis-1-methoxy-cyclohex-4-yl group is equivalent to a cis-4-methoxy-cyclohex-1-yl and has the following structure:

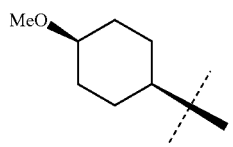

The same conventions apply to other cyclohexyl groups, for example 1-hydroxycyclohex-4-yl groups and 4-hydroxycyclohex-1-yl groups.

The term "tetrahydrofuranyl ring" includes tetrahydrofuran-3-yl, the structure of which is shown below.

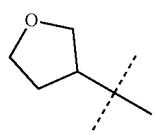

Tetrahydrofuran-3-yl

The term "oxanyl ring" includes oxan-3-yl and oxan-4-yl groups, the structures of which are shown below.

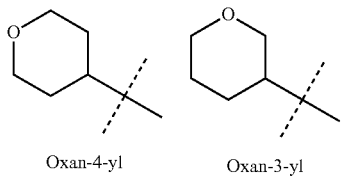

Oxan-4-yl    Oxan-3-yl

In the above structures the dashed line indicates the bonding position of the relevant group.

An oxanyl ring may also be referred to as a tetrahydropyranyl ring. Similarly, an oxan-4-yl ring may be referred to as a tetrahydropyran-4-yl ring, and an oxan-3-yl ring may be referred to as a tetrahydropyran-3-yl ring.

Where the term "optionally" is used, it is intended that the subsequent feature may or may not occur. As such, use of the term "optionally" includes instances where the feature is present, and also instances where the feature is not present. For example, a group "optionally substituted by one methoxy group" includes groups with and without a methoxy substituent.

The term "substituted" means that one or more hydrogens (for example 1 or 2 hydrogens, or alternatively 1 hydrogen) on the designated group is replaced by the indicated substituent(s) (for example 1 or 2 substituents, or alternatively 1 substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH/VHCA, 2002. A suitable pharmaceutically acceptable salt of a compound of Formula (I) is, for example, an acid-addition salt. An acid addition salt of a compound of Formula (I) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid or para-toluenesulfonic acid salt. In one embodiment there is provided a compound of Formula (I) or a pharmaceutically acceptable salt thereof, where the pharmaceutically acceptable salt is a trifluoroacetic acid, formic acid or methanesulfonic acid salt. In one embodiment there is provided a compound of Formula (I) or a pharmaceutically acceptable salt thereof, where the pharmaceutically acceptable salt is a trifluoroacetic acid or methanesulfonic acid salt. In one embodiment there is provided a compound of Formula (I) or a pharmaceutically acceptable salt thereof, where the pharmaceutically acceptable salt is a methanesulfonic acid salt. In one embodiment there is provided a compound of Formula (I) or a pharmaceutically acceptable salt thereof, where the pharmaceutically acceptable salt is a mono-methanesulfonic acid salt, i.e. the stoichiometry of the compound of the compound of Formula (I) to methanesulfonic acid is 1:1.

A further embodiment provides any of the embodiments defined herein (for example the embodiment of claim 1) with the proviso that one or more specific Examples (for instance one, two or three specific Examples) selected from the group consisting of Examples 1, 2, 3, 4, 5, 6, 7, 8, 9, 10, 11, 12 and 13 is individually disclaimed.

A further embodiment provides any of the embodiments defined herein (for example the embodiment of claim 1) with the proviso that one or more specific Examples (for instance one, two or three specific Examples) selected from the group consisting of Examples 1, 2, 3, 4, 5, 6, 7, 8, 9 and 10 is individually disclaimed.

Some values of variable groups in Formula (I) are as follows. Such values may be used in combination with any of the definitions, claims (for example claim 1), or embodiments defined herein to provide further embodiments.

a) $R^1$ is a cyclohexyl ring which is optionally substituted by one or more groups selected from hydroxyl, methoxy and methyl, or $R^1$ is a tetrahydrofuranyl or oxanyl ring.
b) $R^1$ is a cyclohexyl ring which is optionally substituted by one or more groups selected from hydroxyl, methoxy and methyl.
c) $R^1$ is a tetrahydrofuranyl or oxanyl ring.
d) $R^1$ is a cyclohexyl ring which is optionally substituted by one hydroxyl or methoxy group.
e) $R^1$ is a cyclohexyl ring which is optionally substituted by a hydroxyl and a methyl group.
f) $R^1$ is 1-methoxy-cyclohex-4-yl, 1-hydroxy-cyclohex-4-yl, 1-hydroxy-1-methylhex-4yl or 1-hydroxy-4-methyl-cyclohex-4-yl.
g) $R^1$ is 1-methoxy-cyclohex-4-yl, 1-hydroxy-cyclohex-4-yl or 1-hydroxy-1-methyl-cyclohex-4yl.
h) $R^1$ is 1-hydroxy-1-methyl-cyclohex-4-yl.
i) $R^1$ is cis-1-hydroxy-1-methyl-cyclohex-4-yl.
j) $R^1$ is cis-1-methoxy-cyclobut-4-yl or cis-1-hydroxy-cyclohex-4-yl.
k) $R^1$ is cis-1-hydroxy-cyclohex-4-yl.
l) $R^1$ is an oxetanyl ring.
m) $R^1$ is oxetan-3-yl.
n) $R^1$ is an cyclohexyl ring.

o) $R^1$ is a tetrahydrofuranyl ring.
p) $R^1$ is tetrahydrofuran-3-yl.
q) $R^1$ is an oxanyl ring.
r) $R^1$ is an oxan-3-yl.
s) $R^1$ is oxan-4-yl.
t) $R^2$ is hydrogen.
u) $R^2$ is methyl.

In one embodiment there is provided a compound of Formula (I), or a pharmaceutically acceptable salt thereof, wherein the compound is selected from the group consisting of:
9-((1r,4r)-4-hydroxycyclohexyl)-7-methyl-2-((7-methyl-[1,2,4]triazolo[1,5-a]pyridin-6-yl)amino)-7,9-dihydro-8H-purin-8-one;
9-((1s,4s)-4-hydroxycyclohexyl)-7-methyl-2-((7-methyl-[1,2,4]triazolo[1,5-a]pyridin-6-yl)amino)-7,9-dihydro-8H-purin-8-one;
7-methyl-2-((7-methyl-[1,2,4]triazolo[1,5-a]pyridin-6-yl)amino)-9-(tetrahydro-2H-pyran-4-yl)-7,9-dihydro-8H-purin-8-one;
2-((2,7-dimethyl-[1,2,4]triazolo[1,5-a]pyridin-6-yl)amino)-7-methyl-9-(tetrahydro-2H-pyran-4-yl)-7,9-dihydro-8H-purin-8-one;
9-((1s,4s)-4-methoxycyclohexyl)-7-methyl-2-((7-methyl-[1,2,4]triazolo[1,5-a]pyridin-6-yl)amino)-7,9-dihydro-8H-purin-8-one;
9-((1r,4r)-4-methoxycyclohexyl)-7-methyl-2-((7-methyl-[1,2,4]triazolo[1,5-a]pyridin-6-yl)amino)-7,9-dihydro-8H-purin-8-one;
(S)-7-methyl-2-((7-methyl-[1,2,4]triazolo[1,5-a]pyridin-6-yl)amino)-9-(tetrahydro-2H-pyran-3-yl)-7,9-dihydro-8H-purin-8-one;
(R)-7-methyl-2-((7-methyl-[1,2,4]triazolo[1,5-a]pyridin-6-yl)amino)-9-(tetrahydro-2H-pyran-3-yl)-7,9-dihydro-8H-purin-8-one;
9-((1r,4r)-4-hydroxy-4-methylcyclohexyl)-7-methyl-2-((7-methyl-[1,2,4]triazolo[1,5-a]pyridin-6-yl)amino)-7,9-dihydro-8H-purin-8-one;
9-((1 s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one;
(S)-7-methyl-2-((7-methyl-[1,2,4]triazolo[1,5-a]pyridin-6-yl)amino)-9-(tetrahydrofuran-3-yl)-7,9-dihydro-8H-purin-8-one;
9-((1s,4s)-4-hydroxy-1-methylcyclohexyl)-7-methyl-2-((7-methyl-[1,2,4]triazolo[1,5-a]pyridin-6-yl)amino)-7,9-dihydro-8H-purin-8-one; and
9-cyclohexyl-7-methyl-2-((7-methyl-[1,2,4]triazolo[1,5-a]pyridin-6-yl)amino)-7,9-dihydro-8H-purin-8-one.

In one embodiment there is provided a compound of Formula (I), or a pharmaceutically acceptable salt thereof, wherein the compound is selected from the group consisting of:
7-methyl-2-((7-methyl-[1,2,4]triazolo[1,5-a]pyridin-6-yl)amino)-9-(tetrahydro-2H-pyran-4-yl)-7,9-dihydro-8H-purin-8-one;
9-((1r,4r)-4-hydroxy-4-methylcyclohexyl)-7-methyl-2-((7-methyl-[1,2,4]triazolo[1,5-a]pyridin-6-yl)amino)-7,9-dihydro-8H-purin-8-one; and
9-((1 s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one.

In one embodiment there is provided a compound of Formula (I), or a pharmaceutically acceptable salt thereof, wherein the compound is selected from the group consisting of:
7-methyl-2-((7-methyl-[1,2,4]triazolo[1,5-a]pyridin-6-yl)amino)-9-(tetrahydro-2H-pyran-4-yl)-7,9-dihydro-8H-purin-8-one; and
9-((1 s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one.

In one embodiment there is provided a compound of Formula (I), or a pharmaceutically acceptable salt thereof, wherein the compound is 7-methyl-2-((7-methyl-[1,2,4]triazolo[1,5-a]pyridin-6-yl)amino)-9-(tetrahydro-2H-pyran-4-yl)-7,9-dihydro-8H-purin-8-one.

In one embodiment there is provided a compound of Formula (I), or a pharmaceutically acceptable salt thereof, wherein the compound is 9-((1r,4r)-4-hydroxy-4-methylcyclohexyl)-7-methyl-2-((7-methyl-[1,2,4]triazolo[1,5-a]pyridin-6-yl)amino)-7,9-dihydro-8H-purin-8-one.

In one embodiment there is provided a compound of Formula (I), or a pharmaceutically acceptable salt thereof, wherein the compound is 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof.

The invention encompasses all such solvated and unsolvated forms of compounds of Formula (I), particularly to the extent that such forms possess DNA-PK inhibitory activity, as for example measured using the tests described herein.

Atoms of the compounds and salts described in this specification may exist as their isotopes. The invention encompasses all compounds of Formula (I) where an atom is replaced by one or more of its isotopes (for example a compound of Formula (I) where one or more carbon atom is an $^{11}C$ or $^{13}C$ carbon isotope, or where one or more hydrogen atoms is a $^2H$ or $^3H$ isotope, or where one or more nitrogen atoms is a $^{15}N$ isotope or where one of more oxygen atoms is an $^{17}O$ or $^{18}O$ isotope).

Compounds and salts described in this specification may exist in optically active or racemic forms by virtue of one or more asymmetric carbon atoms. The invention includes any optically active or racemic form of a compound of Formula (I) which possesses DNA-PK inhibitory activity, as for example measured using the tests described herein. The synthesis of optically active forms may be carried out by standard techniques of organic chemistry well known in the art, for example by synthesis using optically active materials or by resolution of a racemic form.

Therefore, in one embodiment there is provided a compound of Formula (I), or a pharmaceutically acceptable salt thereof, which is a single optical isomer being in an enantiomeric excess (% ee) of >95%, >98% or >99%. In one embodiment, the single optical isomer is present in an enantiomeric excess (% ee) of >99%.

Some of the compounds of Formula (I) may be crystalline and may have more than one crystalline form. It is to be understood that the disclosure encompasses any crystalline or amorphous form, or mixtures thereof, which form possess properties useful in DNA-PK inhibitory activity. It is well known how to determine the efficacy of a crystalline or amorphous form by the standard tests described hereinafter.

It is generally known that crystalline materials may be analysed using conventional techniques such as, for example, X-ray powder diffraction (hereinafter XRPD) analysis and Differential Scanning Calorimetry (hereinafter DSC).

As an example, the compound of Example 3, 7-methyl-2-((7-methyl-[1,2,4]triazolo[1,5-a]pyridin-6-yl)amino)-9-(tetrahydro-2H-pyran-4-yl)-7,9-dihydro-8H-purin-8-one, exhibits crystallinity and a crystalline form, Form A, has been identified.

Accordingly, in a further aspect there is provided Form A of Compound A (Example 3, 7-methyl-2-((7-methyl-[1,2,4]triazolo[1,5-a]pyridin-6-yl)amino)-9-(tetrahydro-2H-pyran-4-yl)-7,9-dihydro-8H-purin-8-one).

According to the present disclosure there is provided a crystalline form, Form A of Compound A, which has an XRPD pattern with at least one specific peak at about 2-theta=7.6°, as measured using CuKα radiation.

According to the present disclosure there is provided a crystalline form, Form A of Compound A, which has an XRPD pattern with at least one specific peak at about 2-theta=18.7°, as measured using CuKα radiation.

According to the present disclosure there is provided a crystalline form, Form A of Compound A, which has an XRPD pattern with at least two specific peaks at about 2-theta=7.6° and 18.7°, as measured using CuKα radiation.

According to the present disclosure there is provided a crystalline form, Form A of Compound A, which has an XRPD pattern with specific peaks at about 2-theta=7.6, 9.3, 11.7, 14.3, 15.1, 18.7, 23.2, 24.7, 26.4, 27.2°, as measured using CuKα radiation.

According to the present disclosure there is provided crystalline form, Form A of Compound A, which has an XRPD pattern substantially the same as the XRPD pattern shown in FIG. 1.

According to the present disclosure there is provided crystalline form, Form A of Compound A, which has an XRPD pattern with at least one specific peak at 2-theta=7.60 plus or minus 0.2° 2-theta, as measured using CuKα radiation.

According to the present disclosure there is provided a crystalline form, Form A of Compound A, which has an XRPD pattern with at least one specific peak at 2-theta=18.7° plus or minus 0.2° 2-theta, as measured using CuKα radiation.

According to the present disclosure there is provided a crystalline form, Form A of Compound A, which has an XRPD pattern with at least two specific peaks at 2-theta=7.6° and 18.7° wherein said values may be plus or minus 0.2° 2-theta, as measured using CuKα radiation.

According to the present disclosure there is provided a crystalline form, Form A of Compound A, which has an XRPD pattern with specific peaks at 2-theta=7.6, 9.3, 11.7, 14.3, 15.1, 18.7, 23.2, 24.7, 26.4, 27.2° wherein said values may be plus or minus 0.2° 2-theta, as measured using CuKα radiation.

DSC analysis of Compound A, Form A shows a melting endotherm with an onset of about 261.8° C. plus or minus 0.5° C. and a peak at about 262.7° C. plus or minus 0.5° C. (FIG. 2).

The compound of Example 10, 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one, exhibits crystallinity and a crystalline form, Form A, has been identified.

Accordingly, in a further aspect there is provided Form A of Compound B (Example 10, 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one).

According to the present disclosure there is provided a crystalline form, Form A of Compound B, which has an XRPD pattern with at least one specific peak at about 2-theta=8.8°, as measured using CuKα radiation.

According to the present disclosure there is provided a crystalline form, Form A of Compound B, which has an XRPD pattern with at least one specific peak at about 2-theta=12.7°, as measured using CuKα radiation.

According to the present disclosure there is provided a crystalline form, Form A of Compound B, which has an XRPD pattern with at least two specific peaks at about 2-theta=8.8° and 12.7°, as measured using CuKα radiation.

According to the present disclosure there is provided a crystalline form, Form A of Compound B, which has an XRPD pattern with specific peaks at about 2-theta=5.1, 8.8, 10.3, 12.7, 13.0, 13.8, 14.8, 16.5, 23.8, 24.2°, as measured using CuKα radiation.

According to the present disclosure there is provided crystalline form, Form A of Compound B, which has an XRPD pattern substantially the same as the X-ray powder diffraction pattern shown in FIG. 3.

According to the present disclosure there is provided crystalline form, Form A of Compound B, which has an XRPD pattern with at least one specific peak at 2-theta=8.8° plus or minus 0.2° 2-theta, as measured using CuKα radiation.

According to the present disclosure there is provided a crystalline form, Form A of Compound B, which has an XRPD pattern with at least one specific peak at 2-theta=12.7° plus or minus 0.2° 2-theta, as measured using CuKα radiation.

According to the present disclosure there is provided a crystalline form, Form A of Compound B, which has an XRPD pattern with at least two specific peaks at 2-theta=8.8° and 12.7° wherein said values may be plus or minus 0.2° 2-theta, as measured using CuKα radiation.

According to the present disclosure there is provided a crystalline form, Form A of Compound B, which has an XRPD pattern with specific peaks at 2-theta=5.1, 8.8, 10.3, 12.7, 13.0, 13.8, 14.8, 16.5, 23.8, 24.2° wherein said values may be plus or minus 0.2° 2-theta, as measured using CuKα radiation.

DSC analysis of Compound B, Form A shows a melting endotherm with an onset of about 235.6° C. plus or minus 0.5° C. and a peak at about 236.9° C. plus or minus 0.5° C. (FIG. 4).

When it is stated that the present disclosure relates to a crystalline form of Form A of Compound A or Compound B, the degree of crystallinity is conveniently greater than about 60%, more conveniently greater than about 80%, preferably greater than about 90% and more preferably greater than about 95%. Most preferably the degree of crystallinity is greater than about 98%.

It will be understood that the 2-theta values of the XRPD pattern may vary slightly from one machine to another or from one sample to another, and so the values quoted are not to be construed as absolute.

It is known that an XRPD pattern may be obtained which has one or more measurement errors depending on measurement conditions (such as equipment or machine used). In particular, it is generally known that intensities in an XRPD pattern may fluctuate depending on measurement conditions. Therefore it should be understood that Compound A, Form A and Compound B, Form A of the present disclosure are not limited to the crystals that provide XRPD patterns identical to the XRPD pattern shown in FIGS. 1 and 3, and any crystals providing XRPD patterns substantially the same as that shown in FIGS. 1 and 3 fall within the scope of the present disclosure. A person skilled in the art of XRPD is able to judge the substantial identity of XRPD patterns.

Persons skilled in the art of XRPD will understand that the relative intensity of peaks can be affected by, for example, grains above 30 microns in size and non-unitary aspect ratios, which may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the XRPD pattern in FIGS. 1 and 3 and when reading Tables A and B. Furthermore, it should be understood that intensities might fluctuate depending on experimental conditions and sample preparation (preferred orientation).

Compounds of Formula (I) may for example be prepared by the reaction of a compound of Formula (II):

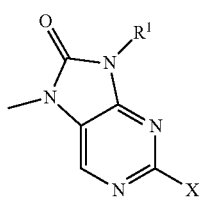
(II)

or a salt thereof, where $R^1$ is as defined in any of the embodiments herein, or a protected form thereof, and X is a leaving group (for example a halogen atom, such as a chlorine atom) with a compound of Formula (III):

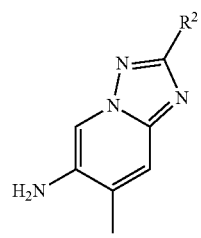
(III)

or a salt thereof. The reaction is conveniently performed in a suitable solvent (for example 1,4-dioxane) in the presence of a base (for example cesium carbonate) and optionally in the presence of a suitable catalyst (for example Brettphos $3^{rd}$ Gen) at a suitable temperature (for example a temperature in the range of about 80-100° C.).

Compounds of Formula (II) or (III), and salts thereof, are therefore useful as intermediates in the preparation of the compounds of Formula (I) and provide a further embodiment. In one embodiment there is provided a compound of Formula (II), or a salt thereof, where:

$R^1$ is a cyclohexyl, tetrahydrofuranyl or oxanyl ring, each of which is optionally substituted by one or more groups selected from hydroxyl, methoxy and methyl; and X is a leaving group.

In one embodiment X is a halogen atom or a triflate group. In one embodiment X is a chlorine atom.

In any of the embodiments where a compound of Formula (II) or (III) or a salt thereof is mentioned it is to be understood that such salts do not need to be pharmaceutically acceptable salts. A suitable salt of a compound of Formula (II) or (III) is, for example, an acid-addition salt. An acid addition salt of a compound of Formula (II) or (III) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

Therefore, in one embodiment there is provided a compound of Formula (II) or (III) or a salt thereof, where the salt is a hydrochloric acid, hydrobromic acid, sulphuric acid, phosphoric acid, trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid or para-toluenesulfonic acid salt.

The compounds of Formula (II) may for example be prepared by the reaction of a compound of Formula (IV):

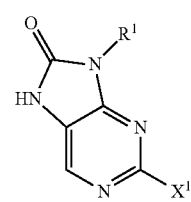
(IV)

where $R^1$ is as defined in any of the embodiments herein, and $X^1$ is a leaving group (for example an iodine, bromine, or chlorine atom or a triflate group) with a methylating agent. Suitable methylating agents include methyl iodide, DMF-DMA.

The compounds of Formula (IV) may for example be prepared by the reaction of a compound of Formula (V):

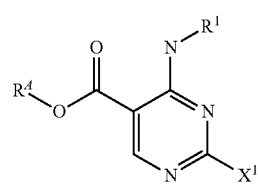
(V)

where $R^1$ is as defined in any of the embodiments herein; $R^4$ is hydrogen; and $X^1$ is a leaving group (for example an iodine, bromine, chlorine atom or a triflate group) with diphenylphosphoryl azide (DPPA). The reaction may be performed under standard conditions well known to those skilled in the art, for example DPPA, triethylamine, THF, reflux.

Compounds of Formula (IV) and (V) are therefore useful as intermediates in the preparation of the compounds of Formula (I) and provide a further embodiment.

Compounds of Formula (IV) and (V) can be prepared by methods similar to those shown in the Examples section.

The compound of Formula (III) may for example be prepared by the reaction of a compound of Formula (VI):

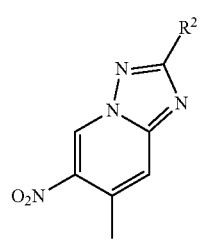

(VI)

with a reducing agent. Suitable reducing agents include 10% Pd/C and hydrogen, 10% Pd/C and ammonium formate, iron/ammonium chloride.

The compound of Formula (VI) may for example be prepared by the reaction of a compound of Formula (VII):

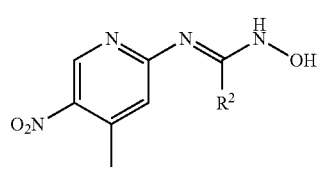

(VII)

with a cyclisation reagent. Suitable cyclisation reagents include trifluoroacetic anhydride.

The compound of Formula (VII) may for example be prepared by the reaction of a compound of Formula (VIII):

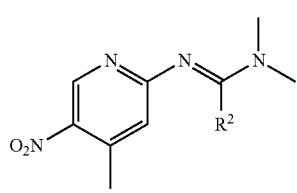

(VIII)

with hydroxylamine hydrochloride.

The compound of Formula (VIII) may for example be prepared by the reaction of a compound of Formula (IX):

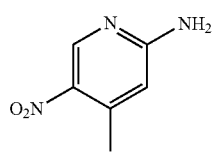

(IX)

with 1,1-dimethoxy-N,N-dimethylmethanamine.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example compounds of Formula (I) may be converted into further compounds of Formula (I) by standard aromatic substitution reactions or by conventional functional group modifications. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

Compounds of Formula (I), (II) and (III), and any intermediates used to make these, can be prepared by methods similar to those shown in the Examples section.

Biological Assays

The following assays were used to measure the effects of the compounds described herein: a) DNAPK enzyme potency assay; b) DNAPK cellular potency assay. During the description of the assays, generally:

i. The following abbreviations have been used; DMSO=Dimethyl Sulphoxide; DTT=Dithiothreitol; EDTA=Ethylenediaminetetraacetic Acid, TR-FRET=Time Resolved Fluorescence Resonance Energy Transfer, ATP=Adenosine triphosphate, DTT=Dithiothreitol, DNA=Deoxyribonucleic acid, HEPES=(2-hydroxyethyl)-1-piperazineethanesulfonic acid ii. The $IC_{50}$ value was the concentration of test compound that inhibited 50% of biological activity.

Assay a): DNAPK Enzyme Potency Assay (DNA-PK Enz)

The inhibitory activity of compounds against DNAPK was determined by TR-FRET measuring a fluorescent labelled peptide substrate converting to a phosphorylated product. fluorescently tagged peptide substrate were purchased from Thermo Fisher Scientific. 12 point half-log compound concentration-response curves, with a top concentration of 100 μM were generated from 10 mM stocks of compound solubilised in DMSO using an Echo 555 (Labcyte Inc., Sunnyvale, Calif.). All assays were preformed in white Greiner 1536 well low volume plates (Greiner Bio-One, UK), in a total reaction volume of 3 µL and 1% (v/v) final DMSO concentration. Enzymes and substrates were added separately to the compound plates and incubated at room temperature. The kinase reaction was then quenched by the addition of 3 µL of stop buffer. Stopped assay plates were read using a BMG Pherastar. $IC_{50}$ values were calculated using a Genedata Screener® software (Genedata, Inc., Basel, Switzerland).

Full length human DNAPK protein was purified from HeLa cell extract by ion exchange. Initially DNAPK protein was incubated with compound for 30 minutes at room temperature in reaction buffer (50 mM Hepes pH 7.5, 0.01% Brij-35, 10 mM $MgCl_2$, 1 mM EGTA, 1 mM DTT, 2 µg/ml Calf Thymus DNA). The reaction was then initiated by the addition of ATP and fluorescently tagged peptide substrate (Fluorescein-EPPLSQEAFADLWKK, Thermo Fisher Scientific). The kinase reaction (18 µM ATP, 35 µM DNAPK, 1.6 µM peptide substrate) was quenched after 40 minutes by the addition of 3 µL of stop buffer (20 mM Tris pH7.5, 0.02% sodium azide, 0.01% Nonidet-P40, 20 m EDTA, 4 nM Tb anti-phospho-p53 [Ser15] Antibody. The reaction was incubated for a further hour and the plates were read on a BMG Pherastar.

Data was analysed and IC50 values were calculated using Genedata Screener® software (Genedata, Inc., Basel, Switzerland). The $pIC_{50}$ values were calculated as the negative logarithm of the molar concentration of compound required for 50% reduction in measured response.

b) DNAPK Cellular Potency Assay (DNA-PK Cell)

Compounds or DMSO (dimethyl sulphoxide) were dispensed from source plates containing compounds at 10 mM in 100% (v/v) DMSO or 100% DMSO, directly into cell assay plates using an Echo 555 Acoustic dispenser (Labcyte Inc™). 10 mM compound stocks were diluted 1:100 using a fixed-tip 96-head Agilent VPrep liquid handler (Agilent Technologies, Santa Clara, Calif.) to give four intermediate dilutions (10 mM, 100 µM, 1 µM, 10 nM). This 1:100 intermediate dilution plate was then used by the Echo to dispense compounds and DMSO directly into the cell plates with a 12 point dose range (30, 10, 3.125, 1.25, 0.3, 0.1, 0.03125, 0.0125, 0.003, 0.001, 0.0003125, 0.00003 µM) in order to calculate compound $IC_{50}$ values, with a total DMSO concentration in the assay of 0.3% (v/v).

The DNAPK cell ELISA assay was performed in the A549 cell line. A549 cells were cultured in cell media composed of MEM-F12 (Minimum Essential Medium F12 Sigma #D6421), 10% (v/v) Foetal Calf Serum and 1% (v/v) 200 mM L-Glutamine. After harvesting, cells were dispensed into black, 384-well Costar plates (#3712, Corning) to give 15,000 cells per well in a total volume of 40 ul cell media, and were incubated overnight at 37° C., 90% relative humidity and 5% $CO_2$ in a rotating incubator. Greiner 781077 all-black high-bind 384-well ELISA plates were coated with 0.5 ug/ml DNAPK antibody (Abcam #ab1832) in PBS/A overnight at 4° C. The following day the Greiner ELISA plates were washed 3× with PBS-T and blocked with 3% BSA/PBS for 2 h, before a further 3× wash with PBS-T.

Test compounds and reference controls were dosed directly into the cell plates using a Labcyte Echo 555 acoustic dispenser. The cell plates were then incubated for 1 h at 37° C. before receiving a radiation dose of 8 Gy (XRAD 320, table height 65). The cells were incubated for a further 1 h before removal of cell media. Lysis buffer (in-house preparation with addition of protease inhibitor cocktail tablets, Roche #04 693 116 001 and phosphatase inhibitor tablets, Roche #04906837001) was dispensed at 25 l/well and plates were incubated at 4° C. for 30 min. Cell lysates (20 l/well) were transferred to the DNAPK antibody-coated ELISA plates using a CyBio Felix liquid handling platform, and ELISA plates were incubated at 4° C. overnight.

The following day, ELISA plates were washed 3× with PBS-T and dispensed with in-house pS2056-DNAPK antibody (0.5 µg/ml in 3% BSA/PBS) at 20 l/well. Plates were incubated with antibody for 2 h at room temperature (RT) before 3× wash with PBS-T. Goat anti-rabbit HRP secondary antibody (1:2000 dilution in 3% BSA/PBS; Cell Signaling #7074) was dispensed at 20 l/well and plates were incubated at RT for 1 h before 3× wash with PBS-T.

QuantaBlu Working Substrate Solution (Thermo Scientific #15169, prepared according to manufacturer's instructions) was dispensed at 20 µl/well and plates were incubated at RT for 1 h before a further 20 l/well dispense with QuantaBlu Stop Solution provided within kit (Thermo Scientific #15169). The fluorescence intensity of individual wells was determined using a PerkinElmer EnVision plate reader.

Data was analysed and $IC_{50}$ values were calculated using Genedata Screener® software (Genedata, Inc., Basel, Switzerland). The $pIC_{50}$ values were calculated as the negative logarithm of the molar concentration of compound required for 50% reduction in measured response.

c) TTK Enzyme Assay

The inhibitory activity of compounds against TTK was determined in a LanthaScreen® Eu Kinase Binding assay run by ThermoFisher Scientific as part of their SelectScreen® Biochemical Kinase Profiling Service. The LanthaScreen® Eu Kinase Binding assay format uses binding of an Alexa Fluor® conjugate or "tracer" to a kinase, which is detected by addition of a Eu-labeled anti-tag antibody. Binding of the tracer and antibody to a kinase results in a high degree of FRET, whereas displacement of the tracer with a kinase inhibitor results in a loss of FRET. The degree of FRET measured in the assay is used to determine the binding of a compound.

10 point three-fold dilution compound concentration-response curves, with a top concentration of 10 µM were generated from 10 mM stocks of compound solubilised in DMSO. All assays were performed in white, low volume Greiner 384-well plates (cat. #784207, Greiner), in a total reaction volume of 16 µL and 1% (v/v) final DMSO concentration. 3.84 µL Kinase Buffer (50 mM HEPES pH 7.5, 0.01% BRIJ-35, 10 mM $MgCl_2$, 1 mM EGTA), 8 µL 2× Kinase/Antibody mixture (final concentrations 5 nM TTK, 2 nM Eu-anti-GST, prepared in Kinase Buffer) and 4 µL 4× AlexaFluor® labeled Tracer Solution (final concentrations 30 nM Tracer 236, prepared in Kinase Buffer) were added separately to the compound plates, placed on a plate shaker for 30 sec, and then incubated for 60 mins at room temperature. Plates were then read using a fluorescence plate reader. $IC_{50}$ values were calculated using XLfit software (IDBS Ltd, Surrey, UK), with the curve fit to model number 205 (sigmoidal dose-response model).

d) Aurora-A, Aurora-B, JAK1, JAK2, JAK3 Enzyme Assays

The inhibitory activity of compounds against AURKA, AURKB, JAK1, JAK2 and JAK3 was determined in Z'-LYTE® assays run by ThermoFisher Scientific as part of their SelectScreen® Biochemical Kinase Profiling Service. The Z'-LYTE® biochemical assay format employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair. In the primary reaction, the kinase transfers the gamma-phosphate of ATP to a single tyrosine, serine or threonine residue in a synthetic FRET-peptide. In the secondary reaction, a site-specific protease recognises and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress. Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

10 point three-fold dilution compound concentration-response curves, with a top concentration of 10 µM were generated from 10 mM stocks of compound solubilised in DMSO. All assays were performed in black, non-binding, low volume Corning 384-well plates (cat. #4514, Corning), in a total reaction volume of 10 µL and 1% (v/v) final DMSO concentration. 2.4 µL Kinase Buffer (50 mM HEPES pH 7.5, 0.01% BRIJ-35, 10 mM $MgCl_2$, 1 mM EGTA), 5 µL 2× Peptide/Kinase mixture (detailed below for each kinase) and 2.5 µL 4×ATP Solution (prepared in Kinase Buffer) were added separately to the compound plates, placed on a plate shaker for 30 sec, and then incubated for 60 mins at room temperature. The kinase reaction was then quenched by the addition of 5 µL of Development Reagent (ThermoFisher Scientific proprietary). Assay plates were placed on a plate shaker for 30 sec, incubated for 60 mins at room temperature, and then read using a fluorescence plate reader. $IC_{50}$ values were calculated using XLfit software (IDBS Ltd, Surrey, UK), with the curve fit to model number 205 (sigmoidal dose-response model).

Aurora A (AurA):

The 2X AURKA (Aurora A)/Ser/Thr 01 (ThermoFisher Scientific proprietary) mixture was prepared in 50 mM HEPES pH 7.5, 0.01% BRIJ-35, 10 mM $MgCl_2$, 1 mM EGTA. The final 10 µL Kinase Reaction consisted of 15 nM AURKA (Aurora A), 2 µM Ser/Thr 01 and 10 µM ATP (Km app) in 50 mM HEPES pH 7.5, 0.01% BRIJ-35, 10 mM $MgCl_2$, 1 mM EGTA. After the 1 hour Kinase Reaction incubation, 5 µL of a 1:4096 dilution of Development Reagent was added.

Aurora B (AurB):

The 2X AURKB (Aurora B)/Ser/Thr 01 (ThermoFisher Scientific proprietary) mixture was prepared in 50 mM HEPES pH 7.5, 0.01% BRIJ-35, 10 mM $MgCl_2$, 1 mM EGTA. The final 10 µL Kinase Reaction consisted of 23 nM AURKB (Aurora B), 2 µM Ser/Thr 01 and 75 µM ATP (Km app measured as 81 µM ATP) in 50 mM HEPES pH 7.5, 0.01% BRIJ-35, 10 mM $MgCl_2$, 1 mM EGTA. After the 1 hour Kinase Reaction incubation, 5 µL of a 1:4096 dilution of Development Reagent was added.

JAK1:

The 2X JAK1/Tyr 06 (ThermoFisher Scientific proprietary) mixture was prepared in 50 mM HEPES pH 6.5, 0.01% BRIJ-35, 10 mM $MgCl_2$, 1 mM EGTA, 0.02% NaN3. The final 10 µL Kinase Reaction consisted of 74 nM JAK1, 2 µM Tyr 06 and 75 µM ATP (Km app measured as 87 µM ATP) in 50 mM HEPES pH 7.0, 0.01% BRIJ-35, 10 mM $MgCl_2$, 1 mM EGTA, 0.01% NaN3. After the 1 hour Kinase Reaction incubation, 5 µL of a 1:128 dilution of Development Reagent was added.

JAK2:

The 2×JAK2/Tyr 06 (ThermoFisher Scientific proprietary) mixture was prepared in 50 mM HEPES pH 7.5, 0.01% BRIJ-35, 10 mM $MgCl_2$, 1 mM EGTA. The final 10 µL Kinase Reaction consisted of 0.27 nM JAK2, 2 µM Tyr 06 and 25 µM ATP (Km app measured as 31 µM ATP) in 50 mM HEPES pH 7.5, 0.01% BRIJ-35, 10 mM $MgCl_2$, 1 mM EGTA. After the 1 hour Kinase Reaction incubation, 5 µL of a 1:128 dilution of Development Reagent was added.

JAK3:

The 2×JAK3/Tyr 06 (ThermoFisher Scientific proprietary) mixture was prepared in 50 mM HEPES pH 7.5, 0.01% BRIJ-35, 10 mM $MgCl_2$, 1 mM EGTA. The final 10 µL Kinase Reaction consisted of 2.4 nM JAK3, 2 µM Tyr 06 and 10 µM ATP (Km app measured as 14 µM ATP) in 50 mM HEPES pH 7.5, 0.01% BRIJ-35, 10 mM $MgCl_2$, 1 mM EGTA. After the 1 hour Kinase Reaction incubation, 5 µL of a 1:128 dilution of Development Reagent was added.

e) Mouse Xenograft Model—Olaparib Combination

Female scid mice were transplanted s.c. with 5 million cells of the ATM null pharynx cancer cell line FaDu ATM KO to determine the in-vivo anti-tumour activity of a DNA-PK inhibitor and its combination with olaparib.

Animals were initially randomised into groups of 15 when tumours reached a volume of 290 $mm^3$ and treatment commenced. This tumour model has a tumour loss rate of 50%, where up to 8 animals per group were expected to be lost from the study analysis due to spontaneous ulceration of their tumours. Animals were dosed twice daily with a compound of Formula (I) orally, with both oral doses separated by 8 h. Olaparib was dosed daily 1 h after the first daily dose of a compound of Formula (I). Tumours were measured three times weekly by caliper and volume of tumours calculated using formula [length×$width^2$]/2 was used, where the length and the width are the longest and the shortest diameters of the tumour, respectively. Olaparib was formulated in a 10% (w/v) DMSO/10% (w/v) HP-b-CD (Kleptose), 80% water for injection solution. Compounds of Formula (I) were formulated in a 0.5% (w/v) hydroxypropyl methylcellulose (HPMC), 0.1% (v/v) Tween 80.

The results of testing Example 3 in assay e) are shown in FIG. 5. "qd" means a once daily dose. "bid" means a twice daily dose.

f) Cell Growth Assays—In Vitro Activity of Combination with ATR or ATM Inhibitor Cell growth assays were used to determine the in vitro activity of a compound of Formula (I) and its combination with an ATR (AZD6738) and ATM inhibitor (AZD0156).

FaDu pharynx cancer cell line was routinely cultured in phenol red-free RPMI medium (Sigma) supplemented with 10% foetal calf serum and 1% GlutaMAX (Thermo Fisher). Cultures were maintained at 37° C. in a humidified atmosphere with 5% $CO_2$. Cells were detached using TryLE Express solution (Thermo Fisher) and were plated at 500 cells per well in 70 µl culture medium in two 384 well flat bottomed plates (Greiner, Catalogue Number 781090). In the test plate, cells were treated the following day (Day 0) with either Example 3 (3 µM), AZD6738 (1 NM), AZD0156 (0.3 µM), a combination of inhibitor compounds or vehicle at the appropriate volume as a control experiment, using the Echo 555 Liquid Handler (Labcyte). All inhibitors were reconstituted in 100% DMSO vehicle.

Cell numbers were determined using the SYTOX Green Nucleic Acid Stain (Thermo Fisher, Catalogue Number S7020). Cells were incubated with 5 µl SYTOX Green solution (1:2500 in Tris-buffered saline and 5 mM EDTA) for 1.5 hours at room temperature in the dark and the dead cell number was quantified using the Acumen high content imager (TTP LabTech). Total cell number was quantified following 16 hours incubation at room temperature in the dark with 10 µl Saponin solution (0.25% in Tris-buffered saline and 5 mM EDTA) on the Acumen.

Data were analysed using GeneData Screener (Assay Analyzer) software. Briefly, live cell numbers were calculated by subtracting dead cell numbers from total cell numbers. Live cell numbers were normalised relative to Day 0 cell numbers. Cell growth in response to inhibitor treatment (% activity) was determined by fitting the data to a 0-200% scale relative to the control experiments, where 0% represents no change relative to control, 100% represents total cell growth inhibition and 200% represents total cell death. Data were plotted as mean % activity±SD of three independent experiments.

The results of testing Example 3 in assay f) are shown in FIGS. 6 and 7.

The examples were tested in the assays a) b) c) and d) and the following data was observed. The pIC50 values reported below are the calculated mean result of at least 2 experiments.

| Example | DNA-PK enz pIC50 | DNA-PK cell pIC50 | TTK enz pIC50 | JAK1 enz pIC50 | JAK2 enz pIC50 | JAK3 enz pIC50 | AurA enz pIC50 | AurB enz pIC50 |
|---|---|---|---|---|---|---|---|---|
| 1 | >10 | 7.3 | 5.5 | <5 | <5 | <5 | <5 | <5 |
| 2 | 9.8 | 7.3 | 6.1 | <5 | <5 | <5 | <5 | <5 |
| 3 | 9.2 | 7.1 | 5.3 | <5 | <5 | <5 | <5 | <5 |
| 4 | 8.9 | 6.8 | 5.1 | <5 | <5 | <5 | <5 | <5 |
| 5 | 9 | 6.9 | 5.3 | <5 | <5 | <5 | <5 | <5 |
| 6 | 9.6 | 7.4 | 5.9 | <5 | <5 | <5 | <5 | <5 |
| 7 | 9.8 | 7.3 | 5.2 | <5 | <5 | <5 | <5 | <5 |
| 8 | 9.4 | 7.2 | 5.2 | <5 | <5 | <5 | <5 | <5 |
| 9 | 9.5 | 6.9 | 5.4 | <5 | <5 | <5 | <5 | <5 |
| 10 | 9.4 | 7.2 | 6.3 | <5 | <5 | <5 | <5 | <5 |
| 11 | 9.3 | 6.8 | <5.1 | <5 | <5 | <5 | <5 | <5 |
| 12 | 9.7 | 7.4 | 5.8 | <5 | <5 | <5 | <5 | <5 |
| 13 | 9.8 | 7.6 | 6.3 | <5 | <5 | <5 | 5.4 | <5 |

From the data measured it can be seen that the Examples are DNA-PK inhibitors that are selective against these particular targets—TTK, JAK1, JAK2, JAK3, Aurora A, Aurora B. Comparing the enzyme pIC50 values indicate that the Examples have >3 log units of selectivity from DNA-PK to the other targets shown. This equates to >1000× fold selectivity between the IC50 values.

Compounds may be further selected on the basis of further biological or physical properties which may be measured by techniques known in the art and which may be used in the assessment or selection of compounds for therapeutic or prophylactic application.

As a result of their DNA-PK inhibitory activity, the compounds of Formula (I), and pharmaceutically acceptable salts thereof are expected to be useful in therapy.

We have found that the compounds of Formula (I) possess potent anti-tumour activity which it is believed is obtained by way of inhibition of DNA-PK.

Accordingly, the compounds of the present invention are of value as anti-tumour agents. Particularly, the compounds of the present invention are of value as anti-proliferative, apoptotic and/or anti-invasive agents in the containment and/or treatment of solid and/or liquid tumour disease. Particularly, the compounds of the present invention are expected to be useful in the prevention or treatment of those tumours which are sensitive to inhibition of DNA-PK. Further, the compounds of the present invention are expected to be useful in the prevention or treatment of those tumours which are mediated alone or in part by DNA-PK. The compounds may thus be used to produce an DNA-PK enzyme inhibitory effect in a warm-blooded animal in need of such treatment.

As stated herein, inhibitors of DNA-PK should be of therapeutic value for the treatment of proliferative disease such as cancer and in particular solid tumours such as carcinoma and sarcomas and the leukaemias and lymphoid malignancies and in particular for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias [including chronic lymphocytic leukaemia (CLL), acute lymphoctic leukaemia (ALL) and chronic myelogenous leukaemia (CML)], multiple myeloma and lymphomas.

Anti-cancer effects which are accordingly useful in the treatment of cancer in a patient include, but are not limited to, anti-tumour effects, the response rate, the time to disease progression and the survival rate. Anti-tumour effects of a method of treatment of the present invention include but are not limited to, inhibition of tumour growth, tumour growth delay, regression of tumour, shrinkage of tumour, increased time to regrowth of tumour on cessation of treatment, slowing of disease progression. Anti-cancer effects include prophylactic treatment as well as treatment of existing disease.

A DNA-PK inhibitor, or a pharmaceutically acceptable salt thereof, may also be useful for the treatment patients with cancers, including, but not limited to, haematologic malignancies such as leukaemia, multiple myeloma, lymphomas such as Hodgkin's disease, non-Hodgkin's lymphomas (including mantle cell lymphoma), and myelodysplastic syndromes, and also solid tumours and their metastases such as breast cancer, lung cancer (non-small cell lung cancer (NSCLC), small cell lung cancer (SCLC), squamous cell carcinoma), endometrial cancer, tumours of the central nervous system such as gliomas, dysembryoplastic neuroepithelial tumour, glioblastoma multiforme, mixed gliomas, medulloblastoma, retinoblastoma, neuroblastoma, germinoma and teratoma, cancers of the gastrointestinal tract such as gastric cancer, oesophagal cancer, hepatocellular (liver) carcinoma, cholangiocarcinomas, colon and rectal carcinomas, cancers of the small intestine, pancreatic cancers, cancers of the skin such as melanomas (in particular metastatic melanoma), thyroid cancers, cancers of the head and neck and cancers of the salivary glands, prostate, testis, ovary, cervix, uterus, vulva, bladder, kidney (including renal cell carcinoma, clear cell and renal oncocytoma), squamous cell carcinomas, sarcomas such as osteosarcoma, chondrosarcoma, leiomyosarcoma, soft tissue sarcoma, Ewing's sarcoma, gastrointestinal stromal tumour (GIST), Kaposi's sarcoma, and paediatric cancers such as rhabdomyosarcomas and neuroblastomas. Where "cancer" is mentioned, this includes both non-metastatic cancer and also metastatic cancer, such that treating cancer involves treatment of both primary tumours and also tumour metastases.

"DNA-PK inhibitory activity" refers to a decrease in the activity of DNA-PK as a direct or indirect response to the presence of a compound of Formula (I), or pharmaceutically acceptable salt thereof, relative to the activity of DNA-PK kinase in the absence of compound of Formula (I), or pharmaceutically acceptable salt thereof. Such a decrease in activity may be due to the direct interaction of the compound of Formula (I), or pharmaceutically acceptable salt thereof with DNA-PK, or due to the interaction of the compound of Formula (I), or pharmaceutically acceptable salt thereof with one or more other factors that in turn affect DNA-PK activity. For example, the compound of Formula (I), or pharmaceutically acceptable salt thereof may decrease DNA-PK by directly binding to the DNA-PK, by causing (directly or indirectly) another factor to decrease DNA-PK activity, or by (directly or indirectly) decreasing the amount of DNA-PK present in the cell or organism.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In one embodiment there is provided a compound of Formula (I), or a pharmaceutically acceptable salt thereof, for use in therapy.

In one embodiment there is provided the use of the compound of Formula (I), or a pharmaceutically acceptable salt thereof, for the manufacture of a medicament.

In one embodiment there is provided a compound of Formula (I), or a pharmaceutically acceptable salt thereof, for use in the treatment of a disease mediated by DNA-PK. In one embodiment, said disease mediated by DNA-PK is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In one embodiment there is provided a compound of Formula (I), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of a disease mediated by DNA-PK. In one embodiment, said disease mediated by DNA-PK is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In one embodiment there is provided the use of the compound of Formula (I), or a pharmaceutically acceptable salt thereof, for the manufacture of a medicament for the treatment of cancer.

In one embodiment there is provided a method for treating a disease in which inhibition of DNA-PK is beneficial in a warm-blooded animal in need of such treatment, which comprises administering to said warm-blooded animal a therapeutically effective amount of a compound of Formula (I), or a pharmaceutically acceptable salt thereof. In one embodiment, said disease is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

The term "therapeutically effective amount" refers to an amount of a compound of Formula (I) as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of DNA-PK activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of DNA-PK activity as described above.

Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

"Warm-blooded animals" include, for example, humans.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In any embodiment where cancer is mentioned in a general sense, said cancer may be selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer and non-small cell lung cancer. Said cancer may also be selected from the group consisting of colorectal cancer, glioblastoma, gastric cancer, ovarian cancer, diffuse large B-cell lymphoma, chronic lymphocytic leukaemia, head and neck squamous cell carcinoma and lung cancer.

In any embodiment where cancer is mentioned in a general sense the following embodiments may apply:

In one embodiment the cancer is colorectal cancer.
In one embodiment the cancer is glioblastoma.
In one embodiment the cancer is gastric cancer.
In one embodiment the cancer is oesophageal cancer.
In one embodiment the cancer is ovarian cancer.
In one embodiment the cancer is endometrial cancer.
In one embodiment the cancer is cervical cancer.
In one embodiment the cancer is diffuse large B-cell lymphoma.
In one embodiment the cancer is chronic lymphocytic leukaemia.
In one embodiment the cancer is acute myeloid leukaemia.
In one embodiment the cancer is head and neck squamous cell carcinoma.
In one embodiment the cancer is breast cancer.
In one embodiment the cancer is triple negative breast cancer.
In one embodiment the cancer is prostate cancer.
In one embodiment the cancer is bladder cancer.

"Triple negative breast cancer" is any breast cancer that does not express the genes for the oestrogen receptor, progesterone receptor and Her2/neu.

In one embodiment the cancer is hepatocellular carcinoma.
In one embodiment the cancer is lung cancer.

In one embodiment the lung cancer is small cell lung cancer.
In one embodiment the lung cancer is non-small cell lung cancer.
In one embodiment the cancer is metastatic cancer.
In one embodiment the metastatic cancer comprises metastases of the central nervous system.
In one embodiment the metastases of the central nervous system comprise brain metastases.
In one embodiment the metastases of the central nervous system comprise leptomeningeal metastases.

"Leptomeningeal metastases" occur when cancer spreads to the meninges, the layers of tissue that cover the brain and the spinal cord. Metastases can spread to the meninges through the blood or they can travel from brain metastases, carried by the cerebrospinal fluid (CSF) that flows through the meninges.

In one embodiment the cancer is non-metastatic cancer.

The anti-cancer treatment described in this specification may be useful as a sole therapy, or may involve, in addition to administration of the compound of Formula (I), conventional surgery, radiotherapy or chemotherapy; or a combination of such additional therapies. Such conventional surgery, radiotherapy or chemotherapy may be administered simultaneously, sequentially or separately to treatment with the compound of Formula (I).

Radiotherapy may include one or more of the following categories of therapy:
i. External radiation therapy using electromagnetic radiation, and intraoperative radiation therapy using electromagnetic radiation;
ii. Internal radiation therapy or brachytherapy; including interstitial radiation therapy or intraluminal radiation therapy; or
iii. Systemic radiation therapy, including but not limited to iodine 131 and strontium 89.

Therefore, in one embodiment there is provided a compound of Formula (I), or a pharmaceutically acceptable salt thereof, and radiotherapy, for use in the treatment of cancer. In one embodiment the cancer is NSCLC, SCLC, bladder, prostate cancer, esophageal, head and neck, or breast cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with radiotherapy. In one embodiment the cancer is NSCLC, SCLC, bladder, prostate cancer, oesophageal, head and neck, or breast cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, and radiotherapy, for use in the simultaneous, separate or sequential treatment of cancer. In one embodiment the cancer is selected from glioblastoma, lung cancer (for example small cell lung cancer or non-small cell lung cancer), breast cancer (for example triple negative breast cancer), prostate cancer, bladder cancer, head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with radiotherapy. In one embodiment the cancer is selected from glioblastoma, lung cancer (for example small cell lung cancer or non-small cell lung cancer), breast cancer (for example triple negative breast cancer), prostate cancer, bladder cancer, head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a method of treating cancer in a warm-blooded animal who is in need of such treatment, which comprises administering to said warm-blooded animal a compound of Formula (I), or a pharmaceutically acceptable salt thereof and radiotherapy, wherein the compound of Formula (I), or a pharmaceutically acceptable salt thereof, and radiotherapy are jointly effective in producing an anti-cancer effect. In one embodiment the cancer is selected from glioblastoma, lung cancer (for example small cell lung cancer or non-small cell lung cancer), breast cancer (for example triple negative breast cancer), prostate cancer, bladder cancer, head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a method of treating cancer in a warm-blooded animal who is in need of such treatment, which comprises administering to said warm-blooded animal a compound of Formula (I), or a pharmaceutically acceptable salt thereof and simultaneously, separately or sequentially administering radiotherapy, wherein the compound of Formula (I), or a pharmaceutically acceptable salt thereof, and radiotherapy are jointly effective in producing an anti-cancer effect. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases.

In one embodiment the metastases of the central nervous system comprise leptomeningeal metastases.

In any embodiment the radiotherapy is selected from the group consisting of one or more of the categories of radiotherapy listed under points (i)-(iii) above.

Chemotherapy may include one or more of the following categories of anti-tumour substance:

i. Antineoplastic agents and combinations thereof, such as DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; ATM inhibitors (such as AZD0156 and AZD1390); inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEE1 kinase (such as AZD1775/MK-1775);

ia. Antineoplastic agents and combinations thereof, such as DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; ATM inhibitors (such as AZD0156); inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEE1 kinase (such as AZD1775/MK-1775);

ii. Antiangiogenic agents such as those that inhibit the effects of vascular endothelial growth factor, for example the anti-vascular endothelial cell growth factor antibody bevacizumab and for example, a VEGF receptor tyrosine kinase inhibitor such as vandetanib (ZD6474), sorafenib, vatalanib (PTK787), sunitinib (SU11248), axitinib (AG-013736), pazopanib (GW 786034) and cediranib (AZD2171); compounds such as those disclosed in International Patent Applications WO97/22596, WO 97/30035, WO 97/32856 and WO 98/13354; and compounds that work by other mechanisms (for example linomide, inhibitors of integrin αvβ3 function and angiostatin), or inhibitors of angiopoietins and their receptors (Tie-1 and Tie-2), inhibitors of PDGF, inhibitors of delta-like ligand (DLL-4);

iii. Immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor; approaches to decrease T-cell anergy or regulatory T-cell function; approaches that enhance T-cell responses to tumours, such as blocking antibodies to CTLA4 (for example ipilimumab and tremelimumab), B7H1, PD-1 (for example BMS-936558 or AMP-514), PD-L1 (for example MEDI4736 (durvalumab)) and agonist antibodies to CD137; approaches using transfected immune cells such as cytokine-transfected dendritic cells; approaches using cytokine-transfected tumour cell lines, approaches using antibodies to tumour associated antigens, and antibodies that deplete target cell types (e.g., unconjugated anti-CD20 antibodies such as Rituximab, radiolabeled anti-CD20 antibodies Bexxar and Zevalin, and anti-CD54 antibody Campath); approaches using anti-idiotypic antibodies; approaches that enhance Natural Killer cell function; and approaches that utilize antibody-toxin conjugates (e.g. anti-CD33 antibody Mylotarg); immunotoxins such as moxetumumab pasudotox; agonists of toll-like receptor 7 or toll-like receptor 9;

iv. Efficacy enhancers, such as leucovorin.

Therefore, in one embodiment there is provided a compound of Formula (I), or a pharmaceutically acceptable salt thereof, and at least one additional anti-tumour substance, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof is administered in combination with an additional anti-tumour substance. In one embodiment there is one additional anti-tumour substance. In one embodiment there are two additional anti-tumour substances. In one embodiment there are three or more additional anti-tumour substances.

In one embodiment there is provided a compound of Formula (I), or a pharmaceutically acceptable salt thereof, and at least one additional anti-tumour substance for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with an additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is selected from the group consisting of one or more of the anti-tumour substances listed under points (i)-(iv) above.

In one embodiment there is provided a compound of Formula (I), or a pharmaceutically acceptable salt thereof, and at least one anti-neoplastic agent for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one anti-neoplastic agent. In one embodiment the anti-neoplastic agent is selected from the list of antineoplastic agents in point (i) above.

In one embodiment there is provided a compound of Formula (I), or a pharmaceutically acceptable salt thereof, and at least one anti-neoplastic agent for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with at least one anti-neoplastic agent. In one embodiment the antineoplastic agent is selected from the list of antineoplastic agents in point (i) above.

In one embodiment there is provided a compound of Formula (I), or a pharmaceutically acceptable salt thereof, and at least one additional anti-tumour substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, MEDI4736 (durvalumab), AZD1775, AZD6738, AZD1390 and AZD0156, for use in the treatment of cancer.

In one embodiment there is provided a compound of Formula (I), or a pharmaceutically acceptable salt thereof, and at least one additional anti-tumour substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, MEDI4736 (durvalumab), AZD1775 and AZD6738, for use in the treatment of cancer.

In one embodiment there is provided a compound of Formula (I), or a pharmaceutically acceptable salt thereof, and at least one additional anti-tumour substance selected from the group consisting of cisplatin, oxaliplatin, carboplatin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, AZD1775, AZD6738, AZD1390 and AZD0156 for use in the treatment of cancer.

In one embodiment there is provided a compound of Formula (I), or a pharmaceutically acceptable salt thereof, and at least one additional anti-tumour substance selected from the group consisting of cisplatin, oxaliplatin, carboplatin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, AZD1775 and AZD6738, for use in the treatment of cancer.

In one embodiment there is provided a comout of Formula (I), or a pharmaceutically acceptable salt thereof, and olaparib for use in the treatment of cancer.

In one embodiment there is provided a comout of Formula (I), or a pharmaceutically acceptable salt thereof, and AZD6738 for use in the treatment of cancer.

In one embodiment there is provided a comout of Formula (I), or a pharmaceutically acceptable salt thereof, and AZD0156 for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, MEDI4736 (durvalumab), AZD1775, AZD6738, AZD1390 and AZD0156.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of cisplatin, oxaliplatin, carboplatin, valrubicin, idarubicin, doxorubicin, pirarubicin, irinotecan, topotecan, ammrubicin, epirubicin, etoposide, mitomycin, bendamustine, chlorambucil, cyclophosphamide, ifosfamide, carmustine, melphalan, bleomycin, olaparib, MEDI4736 (durvalumab), AZD1775 and AZD6738.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with olaparib.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with AZD6738.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with AZD0156.

In one embodiment there is provided a compound of Formula (I), or a pharmaceutically acceptable salt thereof, and at least one additional anti-tumour substance selected from the group consisting of doxorubicin, irinotecan, topotecan, etoposide, mitomycin, bendamustine, chlorambucil, cyclophosphamide, ifosfamide, carmustine, melphalan, bleomycin and olaparib for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, irinotecan, topotecan, etoposide, mitomycin, bendamustine, chlorambucil, cyclophosphamide, ifosfamide, carmustine, melphalan, bleomycin and olaparib.

In one embodiment there is provided a compound of Formula (I), or a pharmaceutically acceptable salt thereof, and at least one additional anti-tumour substance selected from the group consisting of doxorubicin, irinotecan, topotecan, etoposide, mitomycin, bendamustine, chlorambucil, cyclophosphamide, ifosfamide, carmustine, melphalan and bleomycin, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, irinotecan, topotecan, etoposide, mitomycin, bendamustine, chlorambucil, cyclophosphamide, ifosfamide, carmustine, melphalan and bleomycin.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, pirarubicin, amrubicin and epirubicin. In one embodiment the cancer is acute myeloid leukaemia. In one embodiment the cancer is breast cancer (for example triple negative breast cancer). In one embodiment the cancer is hepatocellular carcinoma.

In one embodiment there is provided a compound of Formula (I), or a pharmaceutically acceptable salt thereof, and irinotecan, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with irinotecan. In one embodiment the cancer is colorectal cancer.

In one embodiment there is provided a compound of Formula (I), or a pharmaceutically acceptable salt thereof, and FOLFIRI, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with FOLFIRI. In one embodiment the cancer is colorectal cancer.

FOLFIRI is a dosage regime involving a combination of leucovorin, 5-fluorouracil and irinotecan.

In one embodiment there is provided a compound of Formula (I), or a pharmaceutically acceptable salt thereof, and R-CHOP, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with R-CHOP. In one embodiment the cancer is non Hodgkin Lymphoma.

R-CHOP is a dosage regime involving a combination of rituximab, cyclophosphamide, hydroxydaunomycin (doxorubicin hydrochloride), onvavin (vincristine) and prednisolone.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with olaparib. In one embodiment the cancer is gastric cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with topotecan. In one embodiment the cancer is small cell lung cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with immunotherapy. In one embodiment the immunotherapy is one or more of the agents listed under point (iii) above. In one embodiment the immunotherapy is an anti-PD-L1 antibody (for example MEDI4736 (durvalumab)).

In one embodiment there is provided a pharmaceutical composition comprising a compound of Formula (I) and at least one additional anti-tumour substance. In one embodiment the pharmaceutical composition also comprises at least one pharmaceutically acceptable diluent or carrier. In one embodiment the anti-tumour substance is an anti-neoplastic agent.

In one embodiment there is provided a pharmaceutical composition comprising a compound of Formula (I) and at least one additional anti-tumour substance, for use in the treatment of cancer. In one embodiment the pharmaceutical composition also comprises at least one pharmaceutically acceptable diluent or carrier. In one embodiment the anti-tumour substance is an anti-neoplastic agent.

According to a further embodiment there is provided a kit comprising:
a) A compound of Formula (I), or a pharmaceutically acceptable salt thereof, in a first unit dosage form;
b) A further additional anti-tumour substance in a further unit dosage form;
c) Container means for containing said first and further unit dosage forms; and optionally
d) Instructions for use. In one embodiment the anti-tumour substance comprises an anti-neoplastic agent.

In any embodiment where an anti-neoplastic agent is mentioned, the anti-neoplastic agent is one or more of the agents listed under point (i) above.

The compounds of Formula (I), and pharmaceutically acceptable salts thereof, may be administered as pharmaceutical compositions, comprising one or more pharmaceutically acceptable diluents or carriers.

Therefore, in one embodiment there is provided a pharmaceutical composition comprising a compound of Formula (I), or a pharmaceutically acceptable salt thereof, and at least one pharmaceutically acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and/or preservative agents.

In one embodiment there is provided a pharmaceutical composition comprising a compound of Formula (I), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

The compound of Formula (I) will normally be administered to a warm-blooded animal at a unit dose within the range 2.5-5000 mg/m$^2$ body area of the animal, or approximately 0.05-100 mg/kg, and this normally provides a therapeutically-effective dose. A unit dose form such as a tablet or capsule will usually contain, for example 0.1-250 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

The various embodiments are illustrated by the following Examples. The invention is not to be interpreted as being limited to the Examples.

Unless stated otherwise, starting materials were commercially available. All solvents and commercial reagents were of laboratory grade and were used as received.

During the preparation of the Examples, generally:
(i) operations were carried out at rt (rt), i.e. in the range 17 to 25° C. and under an atmosphere of an inert gas such as $N_2$ or Ar unless otherwise stated;
(ii) in general, the course of reactions was followed by thin layer chromatography (TLC) and/or analytical high performance liquid chromatography (HPLC or UPLC) which was usually coupled to a mass spectrometer (LCMS). The reaction times that are given are not necessarily the minimum attainable;
(iii) when necessary, organic solutions were dried over anhydrous $MgSO_4$ or $Na_2SO_4$, work-up procedures were carried out using traditional phase separating techniques or by using SCX as described in (xiii), evaporations were carried out either by rotary evaporation in vacuo or in a Genevac HT-4/EZ-2 or Biotage V10;
(iv) yields, where present, are not necessarily the maximum attainable, and when necessary, reactions were repeated if a larger amount of the reaction product was required;

(v) in general, the structures of the end-products of the Formula (I) were confirmed by nuclear magnetic resonance (NMR) and/or mass spectral techniques; electrospray mass spectral data were obtained using a Waters Acquity UPLC coupled to a Waters single quadrupole mass spectrometer acquiring both positive and negative ion data, and generally, only ions relating to the parent structure are reported; proton NMR chemical shift values were measured on the delta scale using either a Bruker AV500 spectrometer operating at a field strength of 500 MHz, a Bruker AV400 operating at 400 MHz or a Bruker AV300 operating at 300 MHz. Unless otherwise stated, NMR spectra were obtained at 500 MHz in d6-dimethylsulfoxide. The following abbreviations have been used: s, singlet; d, doublet; t, triplet; q, quartet; m, multiplet; br, broad; qn, quintet; (vi) Unless stated otherwise compounds containing an asymmetric carbon and/or sulfur atom were not resolved;
(vii) Intermediates were not necessarily fully purified but their structures and purity were assessed by TLC, analytical HPLC/UPLC, and/or NMR analysis and/or mass spectrometry;
(viii) unless otherwise stated, flash column chromatography (fcc) was performed on Merck Kieselgel silica (Art. 9385) or on reversed phase silica (Fluka silica gel 90 C18) or on Silicycle cartridges (40-63 m silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 μm silica) either manually or automated using an Isco CombiFlash Companion system or similar system;
(ix) Preparative reverse phase HPLC (RP HPLC) was performed on C18 reversed-phase silica typically using a Waters XSelect CSH C18 column (5 m silica, 30 mm diameter, 100 mm length) using decreasingly polar mixtures as eluent, for example [containing 0.1% formic acid or 0.3-5% aqueous ammonium hydroxide (d=0.91)] as solvent A and acetonitrile as solvent B; a typical procedure would be as follows: a solvent gradient over 10-20 minutes, at 40-50 mL per minute, from a 95:5 mixture of solvents A and B respectively to a 5:95 mixture of solvents A and B (or alternative ratio as appropriate).
(x) The following analytical UPLC methods were used; in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B.
(xi) Where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;
(xii) Where reactions refer to the use of a microwave, one of the following microwave reactors were used: Biotage Initiator, Personal Chemistry Emrys Optimizer, Personal Chemistry Smithcreator or CEM Explorer;
(xiii) Compounds were purified by strong cation exchange (SCX) chromatography using Isolute SPE flash SCX-2 or SCX-3 columns (International Sorbent Technology Limited, Mid Glamorgan, UK);
(xiv) the following preparative chiral HPLC methods were carried out using a Gilson GX-281 HPLC and a DAICEL CHIRALPAK IC (2×25 cm, 5 um) or DAICEL CHIRALPAK IF (2×25 cm, 5 um); in general a flow rate of between 10-350 ml/minute and detection was by UV absorbance at a typical wavelength of 254 nm. A sample concentration of about 1-100 mg/ml was used in a suitable solvent mixture with an injection volume of between 0.5-10 ml and run time of between 10-150 minutes and a typical oven temperature of 25-35° C.;
(xv) the following analytical chiral HPLC methods were carried out using Shimadzu UFLC and a Daicel CHIRALPAK IC-3 (50×4.6 mm 3 um) or Daicel CHIRALPAK IF-3 (50×4.6 mm 3 um); in general a flow rate of 1 ml/minute and detection was by UV absorbance at a typical wavelength of 254 nm. A sample concentration of about 1 mg/ml was used in a suitable solvent such as EtOH with an injection volume of about 10 μl and run time of between 10-60 minutes and a typical oven temperature of 25-35° C.;
(xvi) the following preparative chiral supercritical fluid chromatography (SFC) methods were used; in general a flow rate of about 70 ml/minute and detection was by UV absorbance at a typical wavelength of 254 nm. A sample concentration of about 100 mg/ml was used in a suitable solvent such as MeOH with an injection volume of about 0.5 ml and run time of between 10-150 minutes and a typical oven temperature of 25-35° C.;
(xvii) in general Examples and intermediate compounds were named using ACD Name, "Structure to Name" part of ChemDraw Ultra (CambridgeSoft), Biovia Draw 2016 or Open Eye OEChem 2.0.2;
(xviii) In addition to the ones mentioned above, the following abbreviations have been used:

| DMF | N,N-dimethylformamide | DMA | N,N-dimethylacetamide |
|---|---|---|---|
| DCM | dichloromethane | THF | tetrahydrofuran |
| conc. | Concentrated | m/z | mass spectrometry peak(s) |
| TBAF | tetra n-butylammonium fluoride | NMP | 1-methylpyrrolidin-2-one |
| EtOAc | ethyl acetate | DIPEA | N,N-diisopropylethylamine |
| DME | 1,2-dimethoxyethane | MeOH | methanol |
| MeCN | acetonitrile | TBAB | tetra n-butylammonium bromide |
| $Et_2O$ | diethyl ether | DBU | 1,8-diazabicyclo[5.4.0]undec-7-ene |
| $Ac_2O$ | acetic anhydride | DMAP | 4-dimethylaminopyridine |
| h | hour(s) | EtOH | ethanol |
| MTBE | methyl tert-butyl ether | Sat. | saturated |
| rt | Rt | fcc | flash column chromatography |

Intermediate 1: (E)-N,N-dimethyl-N'-(4-methyl-5-nitropyridin-2-yl)formimidamide

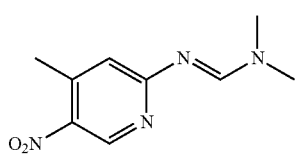

1,1-Dimethoxy-N,N-dimethylmethanamine (26.0 mL, 196 mmol) was added to 4-methyl-5-nitropyridin-2-amine (10.0 g, 65.3 mmol) in toluene (100 mL) at rt. The reaction mixture was heated at reflux for 2 h and the reaction mixture was allowed to cool to rt. The reaction mixture was concentrated to afford the title compound (13.5 g, 99%) as a yellow solid; $^1$H NMR (400 MHz, DMSO) 2.53 (3H, d), 3.06 (3H, d), 3.17 (3H, s), 6.79-6.84 (1H, m), 8.69 (1H, s), 8.88 (1H, s); m/z MH$^+$ 209.

Intermediate 2: (E)-N-hydroxy-N'-(4-methyl-5-nitropyridin-2-yl)formimidamide

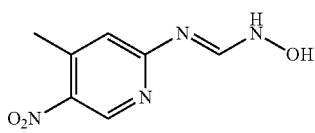

Hydroxylamine hydrochloride (9.01 g, 130 mmol) was added to (E)-N,N-dimethyl-N'-(4-methyl-5-nitropyridin-2-yl)formimidamide (13.5 g, 64.8 mmol) in MeOH (100 mL) at rt. The reaction mixture was heated at reflux for 1 h and then allowed to cool to rt. The reaction mixture was partitioned between EtOAc (200 mL) and water (100 mL). The organic layer was isolated and washed with sat. brine (50 mL), passed through a phase separating filter paper and concentrated to afford the title compound (11.9 g, 94%) as a yellow solid; $^1$H NMR (400 MHz, DMSO) 2.52 (3H, s), 7.06 (1H, s), 7.89 (1H, d), 8.89 (1H, s), 10.10 (1H, d), 10.53 (1H, s); m/z MH$^+$ 197.

Intermediate 3: 7-methyl-6-nitro-[1,2,4]triazolo[1,5-a]pyridine

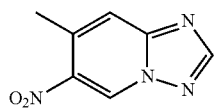

2,2,2-Trifluoroacetic anhydride (10.1 mL, 72.8 mmol) was added to (E)-N-hydroxy-N'-(4-methyl-5-nitropyridin-2-yl)formimidamide (11.9 g, 60.7 mmol) in THF (100 mL) at 0° C. The reaction mixture was stirred at rt for 18 h and was then concentrated. The resulting crude mixture was purified by fcc, eluting with 0-100% EtOAc in heptane, to afford an impure pale orange solid. This solid was recrystallised from heptane:EtOAc, filtered and dried in vacuo, then taken up in EtOAc (100 mL), washed with 0.1 M aq. HCl (50 mL), water (50 mL) and sat. brine (50 mL). The organic layer was passed through a phase separating filter paper and concentrated in vacuo to afford the title compound (3.42 g, 32%); $^1$H NMR (400 MHz, DMSO) 2.67 (3H, s), 7.88-8.01 (1H, m), 8.73 (1H, s), 9.97 (1H, s); m/z MH$^+$ 179.

Intermediate 4: 7-methyl-[1,2,4]triazolo[1,5-a]pyridin-6-amine

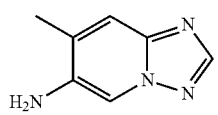

Pd/C (10%, wet support) (0.409 g, 3.84 mmol) was added to 7-methyl-6-nitro-[1,2,4]triazolo[1,5-a]pyridine (3.42 g, 19.2 mmol) and ammonium formate (6.05 g, 96.0 mmol) in ethanol (150 mL) at rt. The reaction mixture was heated at reflux for 2 h The reaction mixture was allowed to cool to rt, filtered and concentrated to afford the title compound (2.60 g, 91%) as a pale brown solid; $^1$H NMR (400 MHz, DMSO) 2.26 (3H, s), 5.00 (2H, s), 7.47 (1H, s), 8.10 (2H, d).

Intermediate 5: 2,7-dimethyl-6-nitro-[1,2,4]triazolo[1,5-a]pyridine

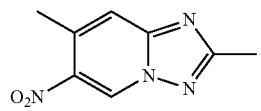

A mixture of 2-chloro-4-methyl-5-nitropyridine (1499 mg, 8.68 mmol), 5-methyl-1,3,4-thiadiazol-2-amine (500 mg, 4.34 mmol) and N-ethyl-N-isopropylpropan-2-amine (1.51 mL, 8.68 mmol) in toluene (5 mL) was placed in a sealed tube and heated at 140° C. thermally for 2 days. Reaction mixture was allowed to cool to rt and concentrated in vacuo. Crude material purified by fcc, elution gradient 0 to 100% EtOAc in heptane to afford the title compound (275 mg, 33%); $^1$H NMR (400 MHz, DMSO) 2.51 (3H, s), 2.64 (3H, s), 7.78 (1H, s), 9.83 (1H, s); m/z MH$^+$ 193.

Intermediate 6: 2,7-dimethyl-[1,2,4]triazolo[1,5-a]pyridin-6-amine

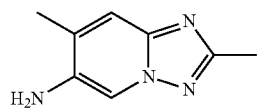

Water (2.32 mL) was added to a stirred mixture of 2,7-dimethyl-6-nitro-[1,2,4]triazolo[1,5-a]pyridine (312 mg, 1.62 mmol), iron (544 mg, 9.74 mmol) and ammonia hydrochloride (60.8 mg, 1.14 mmol) in EtOH (13.9 mL) and the resulting slurry was heated to 90° C. for 2 h. The cooled reaction mixture was loaded onto a 10 g SCX column, washing with MeOH, then eluting with 1M NH$_3$/MeOH to afford crude product. The crude product was purified by fcc, elution gradient 0 to 5% MeOH in DCM, to afford the title compound (108 mg, 41%) as a pale yellow solid; $^1$H NMR (400 MHz, DMSO) 2.24 (3H, s), 2.35 (3H, s), 4.90 (2H, s), 7.33 (1H, s), 8.00 (1H, s); m/z MH$^+$ 163.

Intermediate 7: (1r,4r)-4-((tert-butyldimethylsilyl)oxy)cyclohexanamine (trans-4-{[dimethyl(2-methyl-2-propanyl)silyl]oxy}cyclohexanamine)

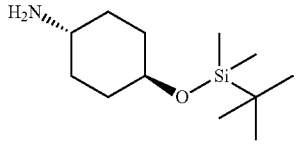

Imidazole (29.6 g, 434 mmol) was added to (trans)-4-aminocyclohexanol (20 g, 174 mmol), in DCM (200 mL). TBDMS-Cl (39.3 g, 260 mmol) was added portionwise and the reaction mixture was stirred at rt for 18 h. The reaction mixture was evaporated to dryness and redissolved in EtOAc (200 mL) and washed sequentially with water (100 mL), 2 M aq. NaOH (100 mL), water (100 mL) and sat. brine (100 mL). The organic layer was dried over $MgSO_4$, filtered and the solvent was removed in vacuo. The crude product was purified by fcc, elution gradient 0 to 10% 1 M methanolic ammonia in DCM, to afford the title compound (30 g, 75%) as a dark golden oil; $^1$H NMR (500 MHz, $CDCl_3$) 0.05 (6H, s), 0.88 (9H, s), 1.05-1.22 (2H, m), 1.26-1.43 (2H, m), 1.44-1.76 (1H, br s) 1.76-1.81 (4H, m), 1.82-2.29 (1H, br s), 2.67 (1H, tt), 3.51-3.63 (1H, m).

Intermediate 8: N-((1r,4r)-4-((tert-butyldimethylsilyl)oxy)cyclohexyl)-2-chloro-5-nitropyrimidin-4-amine (2-chloro-N-(trans-4-{[dimethyl(2-methyl-2-propanyl)silyl]oxy}cyclohexyl)-5-nitro-4-pyrimidinamine)

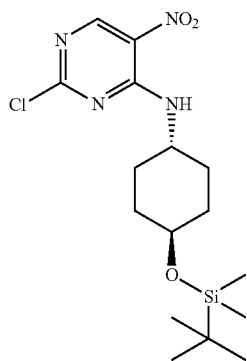 [SMILES: CC(C)(C)[Si](C)(C)O[C@H]1CC[C@H](Nc2nc(Cl)ncc2[N+](=O)[O-])CC1]

2,4-Dichloro-5-nitropyrimidine (20 g, 103 mmol), dissolved in DCM (400 mL), was cooled to −78° C. DIPEA (35.9 mL, 206 mmol) was added followed by dropwise addition of (1r,4r)-4-((tert-butyldimethylsilyl)oxy)cyclohexanamine (23.7 g, 103 mmol), dissolved in DCM (50 mL). The reaction mixture was stirred at −78° C. for 30 minutes then at rt for 18 h. The reaction mixture was washed sequentially with water (200 mL) and saturated brine (200 mL). The organic layer was filtered through a phase separating filter paper and the solvent was removed in vacuo and the residue was triturated in EtOAc:heptane (~1:1) and the resulting solid was filtered off and dried to afford the title compound (32.0 g, 80%) as a pale orange solid; $^1$H NMR (500 MHz, $CDCl_3$) 0.07 (6H, s), 0.90 (9H, s), 1.36-1.48 (2H, m), 1.49-1.6 (2H, m), 1.84-1.96 (2H, m), 2.06-2.19 (2H, m), 3.70 (1H, td), 4.17-4.3 (1H, m), 8.30 (1H, d), 9.03 (1H, s); m/z MH$^+$ 387.

Intermediate 9: N4-((1r,4r)-4-((tert-butyldimethylsilyl)oxy)cyclohexyl)-2-chloropyrimidine-4,5-diamine (2-chloro-N-4-(trans-4-{[dimethyl(2-methyl-2-propanyl)silyl]oxy}cyclohexyl)-4,5-pyrimidinediamine)

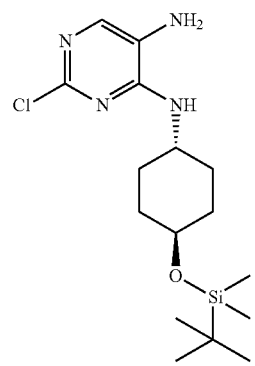

Platinum (10% on carbon) (0.207 g, 1.06 mmol) was added to N-((1r,4r)-4-((tert-butyldimethylsilyl)oxy)cyclohexyl)-2-chloro-5-nitropyrimidin-4-amine (8.20 g, 21.2 mmol) in EtOAc (100 mL) at rt under nitrogen. The reaction mixture was purged with hydrogen and stirred at rt for 18 h. The reaction mixture was filtered, washed with EtOAc and the solvent was removed in vacuo to afford the title compound (7.40 g, 98%); $^1$H NMR (500 MHz, $CDCl_3$) 0.05 (6H, d), 0.89 (9H, d), 1.2-1.32 (2H, m), 1.51 (2H, tdd), 1.87 (2H, dd), 2.06-2.15 (2H, m), 2.91 (2H, br s), 3.63 (1H, ddd), 3.99 (1H, dtd), 4.90 (1H, d), 7.59 (1H, s); m/z MH$^+$ 357.

Intermediate 10: 9-((1r,4r)-4-((tert-butyldimethylsilyl)oxy)cyclohexyl)-2-chloro-7,9-dihydro-8H-purin-8-one (2-chloro-9-(trans-4-{[dimethyl(2-methyl-2-propanyl)silyl]oxy}cyclohexyl)-7,9-dihydro-8H-purin-8-one)

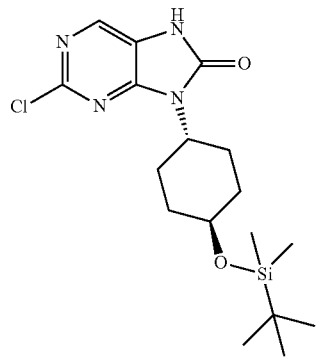 [SMILES: CC(C)(C)[Si](C)(C)O[C@H]1CC[C@H](n2c(=O)[nH]c3cnc(Cl)nc32)CC1]

N4-((r,4r)-4-((tert-butyldimethylsilyl)oxy)cyclohexyl)-2-chloropyrimidine-4,5-diamine (21.8 g, 61.1 mmol) was placed in a flask in EtOAc (400 mL) at rt. Di(1H-imidazol-1-yl)methanone (15.84 g, 97.71 mmol) was added and the reaction mixture was stirred at 70° C. for 2 h. Roughly half of the solvent was removed in vacuo and the solution was cooled on ice for 30 minutes. The resulting solid was filtered off and dried to afford the title compound (10.2 g, 44%) as a pale brown solid; $^1$H NMR (500 MHz, $CDCl_3$) 0.09 (6H, s), 0.90 (9H, s), 1.45-1.56 (2H, m), 1.81 (2H, d), 2.01 (2H, d), 2.45 (2H, qd), 3.75 (1H, ddd), 4.35 (1H, tt), 8.10 (1H, s) NH not observed; m/z MH⁺ 383.

Intermediate 11: 9-((1r,4r)-4-(tert-butyldimethylsilyloxy)cyclohexyl)-2-chloro-7-methyl-7H-purin-8(9H)-one (2-chloro-9-(trans-4-{[dimethyl(2-methyl-2-propanyl)silyl]oxy}cyclohexyl)-7-methyl-7,9-dihydro-8H-purin-8-one)

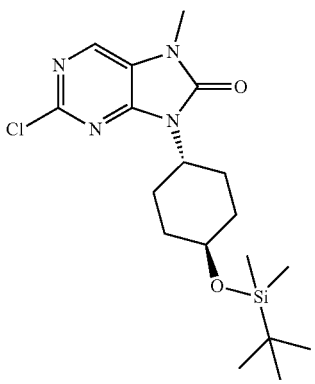 [SMILES: Cn1c(=O)n([C@H]2CC[C@H](O[Si](C)(C)C(C)(C)C)CC2)c2nc(Cl)ncc21]

Sodium hydride (60%) (2.26 g, 56.4 mmol) was added portionwise 9-((1r,4r)-4-((tert-butyldimethylsilyl)oxy)cyclohexyl)-2-chloro-7,9-dihydro-8H-purin-8-one (14.4 g, 37.6 mmol) in DMF (150 mL) at rt. The reaction mixture was stirred for 30 minutes, cooled on ice and then iodomethane (3.92 mL, 62.7 mmol) was added dropwise. The reaction mixture was stirred at rt for 1 h. The reaction mixture was diluted with EtOAc (500 mL), and washed sequentially with water (3×200 mL) and sat. brine (200 mL). The organic layer was filtered through a phase separating filter paper and the solvent was removed in vacuo to afford the title compound (10.4 g, 67%) as a light brown solid; ¹H NMR (500 MHz, CDCl₃) 0.09 (6H, s), 0.90 (9H, s), 1.44-1.54 (2H, m), 1.78 (2H, d), 1.99 (2H, d), 2.43 (2H, qd), 3.43 (3H, s), 3.74 (1H, ddd), 4.36 (1H, tt), 7.98 (1H, s); m/z MH⁺ 397.

Intermediate 12: 9-((1r,4r)-4-((tert-butyldimethylsilyl)oxy)cyclohexyl)-7-methyl-2-((7-methyl-[1,2,4]triazolo[1,5-a]pyridin-6-yl)amino)-7,9-dihydro-8H-purin-8-one (9-(trans-4-{[tert-butyl(dimethyl)silyl]oxy}cyclohexyl)-7-methyl-2-[(7-methyl[1,2,4]triazolo[1,5-a]pyridin-6-yl)amino]-7,9-dihydro-8H-purin-8-one)

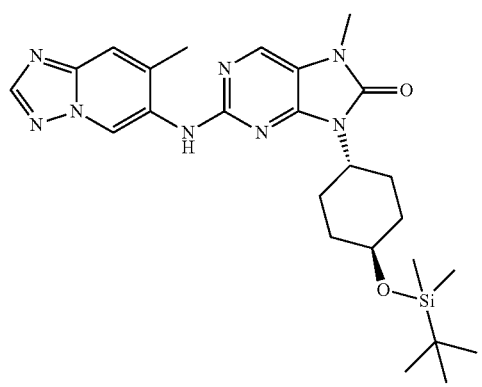 [SMILES: Cc1cc2ncnn2cc1Nc1ncc2c(n1)n([C@H]1CC[C@H](O[Si](C)(C)C(C)(C)C)CC1)c(=O)n2C]

Cesium carbonate (328 mg, 1.01 mmol) was added to 9-((1r,4r)-4-(tert-butyldimethylsilyloxy)cyclohexyl)-2-chloro-7-methyl-7H-purin-8(9H)-one (200 mg, 0.50 mmol) and 7-methyl-[1,2,4]triazolo[1,5-a]pyridin-6-amine (112 mg, 0.76 mmol) in 1,4-dioxane (4 mL). The reaction was degassed and Brettphos precat G3 (45.7 mg, 0.05 mmol) was added. The reaction mixture was stirred at 100° C. for 18 h. Reaction stalled at ~60% conversion. Added a further 10% catalyst and stirred at 100° C. for 2 h. The reaction mixture was cooled to rt, diluted with EtOAc (10 mL), filtered and concentrated to dryness. The crude product was purified by fcc, elution gradient 0 to 10% MeOH in DCM, to afford the title compound (190 mg, 74%) as a brown solid; m/z MH⁺ 509.

Example 1: 9-((1r,4r)-4-hydroxycyclohexyl)-7-methyl-2-((7-methyl-[1,2,4]triazolo[1,5-a]pyridin-6-yl)amino)-7,9-dihydro-8H-purin-8-one

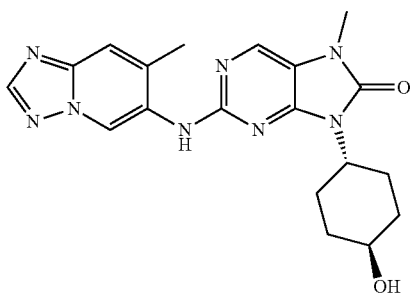 [SMILES: Cc1cc2ncnn2cc1Nc1ncc2c(n1)n([C@H]1CC[C@H](O)CC1)c(=O)n2C]

Conc. hydrochloric acid (0.011 mL, 0.37 mmol) was added to 9-((1r,4r)-4-((tert-butyldimethylsilyl)oxy)cyclohexyl)-7-methyl-2-((7-methyl-[1,2,4]triazolo[1,5-a]pyridin-6-yl)amino)-7,9-dihydro-8H-purin-8-one (190 mg, 0.37 mmol) in EtOH (5 mL) at rt. The reaction mixture was stirred at reflux for 1 h, then was purified by preparative reverse phase HPLC. The resulting impure product was triturated in MeCN, filtered and dried to afford the title compound (55 mg, 37%) as an off-white solid; ¹H NMR (500 MHz, DMSO) 1.17-1.34 (2H, m), 1.68 (2H, d), 1.90 (2H, d), 2.21-2.33 (2H, m), 2.39 (3H, d), 3.28 (3H, s), 3.35-3.46 (1H, m), 4.11 (1H, ddt), 4.61 (1H, d), 7.63-7.71 (1H, m), 8.08 (1H, s), 8.36 (1H, s), 8.61 (1H, s), 9.15 (1H, s); m/z MH⁺ 395.

Intermediate 13: ethyl 2-chloro-4-[(cis-4-hydroxycyclohexyl)amino]pyrimidine-5-carboxylate

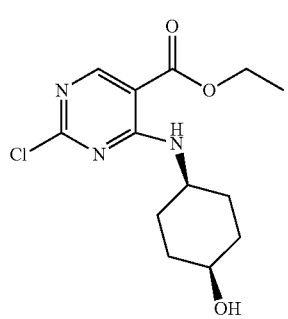 [SMILES: CCOC(=O)c1cnc(Cl)nc1N[C@H]1CC[C@@H](O)CC1]

Potassium carbonate (78 g, 565 mmol) was added to ethyl 2,4-dichloropyrimidine-5-carboxylate (50.0 g, 226 mmol) and cis-4-aminocyclohexanol hydrochloride (34.3 g, 226 mmol) in acetonitrile (700 mL) at rt under air. The reaction mixture was stirred at rt for 16 h. The mixture was filtered through a Celite pad. The filtrate was concentrated under reduced pressure. The precipitate was collected by filtration, washed with MeCN (100 mL) and dried under vacuum to afford the title compound (41.0 g, 61%) as a white solid; $^1$H NMR (400 MHz, DMSO) 1.32 (3H, t), 1.42-1.58 (2H, m), 1.60-1.75 (6H, m), 3.66 (1H, d), 4.06 (1H, dd), 4.33 (2H, q), 4.57 (1H, d), 8.46 (1H, d), 8.63 (1H, s); m/z MH$^+$ 300.

Intermediate 14: 2-chloro-4-[(cis-4-hydroxycyclohexyl)amino]pyrimidine-5-carboxylic Acid

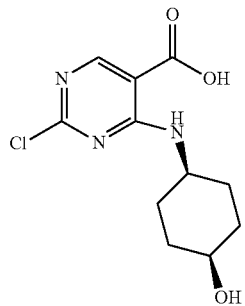 [SMILES: O=C(O)c1cnc(Cl)nc1N[C@H]1CC[C@@H](O)CC1]

LiOH (9.75 g, 407 mmol) was added to ethyl 2-chloro-4-[(cis-4-hydroxycyclohexyl)amino]pyrimidine-5-carboxylate (61.0 g, 204 mmol) in THF (400 mL) and water (400 mL) at rt under air. The reaction mixture was stirred at rt for 16 h. The mixture was concentrated under reduced pressure and adjusted to pH=2 with 2 M aq. HCl. The precipitate was collected by filtration, washed with water (500 mL) and dried under vacuum to afford the title compound (52 g, 94%) as a white solid; $^1$H NMR (400 MHz, DMSO) 1.51 (2H, d), 1.58-1.75 (6H, m), 3.63-3.69 (1H, m), 4.00-4.07 (1H, m), 4.56 (1H, s), 8.59 (1H, s), 8.69 (1H, d), 13.82 (1H, s); m/z MH$^+$ 272.

Intermediate 15: 2-chloro-9-((1s,4s)-4-hydroxycyclohexyl)-7,9-dihydro-8H-purin-8-one

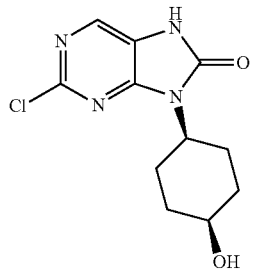 [SMILES: O=c1[nH]c2cnc(Cl)nc2n1[C@H]1CC[C@@H](O)CC1]

Triethylamine (28.2 mL, 202 mmol) was added to 2-chloro-4-[(cis-4-hydroxycyclohexyl)amino]pyrimidine-5-carboxylic acid (55.0 g, 202 mmol) in acetonitrile (550 mL) at rt under air. The reaction mixture was stirred at rt for 15 minutes. DPPA (55.7 g, 202 mmol) was added. The reaction mixture was stirred at rt for 30 minutes and then 90° C. for 6 h. The reaction mixture was poured into water (4 L). The precipitate was collected by filtration, washed with water (1 L) and dried under vacuum to afford the title compound (34.9 g, 64%) as a white solid; m/z MH$^+$ 269.

Intermediate 16: 2-chloro-9-((1s,4s)-4-hydroxycyclohexyl)-7-methyl-7,9-dihydro-8H-purin-8-one

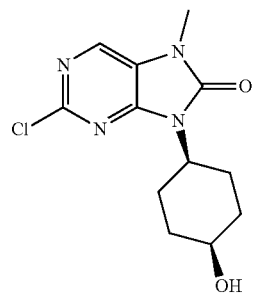

Iodomethane (31.7 g, 223 mmol) was added to 2-chloro-9-((1s,4s)-4-hydroxycyclohexyl)-7,9-dihydro-8H-purin-8-one (30.0 g, 112 mmol), NaOH (22.3 g, 558 mmol) in THF (300 mL) and water (150 mL) at rt. The reaction mixture was stirred at rt for 16 h. The reaction mixture was concentrated in vacuo. The precipitate was collected by filtration, washed with water (250 mL) and dried under vacuum to afford the title compound (24.0 g, 76%) as a white solid; $^1$H NMR (400 MHz, DMSO) 1.43-1.61 (4H, m), 1.79 (2H, d), 2.54-2.68 (2H, m), 3.34 (3H, s), 3.87 (1H, s), 4.15-4.21 (1H, m), 4.46 (1H, d), 8.34 (1H, s); m/z MH$^+$ 283.

Example 2: 9-((1s,4s)-4-hydroxycyclohexyl)-7-methyl-2-((7-methyl-[1,2,4]triazolo[1,5-a]pyridin-6-yl)amino)-7,9-dihydro-8H-purin-8-one

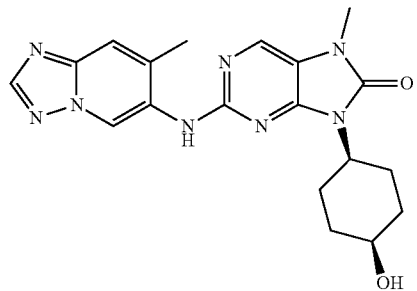 [SMILES: Cc1cc2ncnn2cc1Nc1ncc2c(n1)n([C@H]1CC[C@@H](O)CC1)c(=O)n2C]

Brettphos precat G3 (64.1 mg, 0.07 mmol) was added to 2-chloro-9-((1s,4s)-4-hydroxycyclohexyl)-7-methyl-7,9-dihydro-8H-purin-8-one (100 mg, 0.35 mmol), 7-methyl-[1,2,4]triazolo[1,5-a]pyridin-6-amine (62.9 mg, 0.42 mmol) and cesium carbonate (230 mg, 0.71 mmol) in 1,4-dioxane (3 mL) under nitrogen. The reaction mixture was stirred at 100° C. for 16 h. The crude product was purified by preparative HPLC to afford the title compound (102 mg, 73%) as a white solid; $^1$H NMR (400 MHz, DMSO) 1.41-1.57 (4H, m), 1.74-1.85 (2H, m), 2.39 (3H, s), 2.58-2.74 (2H, m), 3.29 (3H, s), 3.84-3.91 (1H, m), 4.11-4.24 (1H, m), 4.34 (1H, m), 4.58 (1H, s), 7.69 (1H, d), 8.05 (1H, s), 8.37 (1H, s), 8.61 (1H, s), 9.13 (1H, s); m/z MH$^+$ 395.

Intermediate 17: ethyl 2-chloro-4-((tetrahydro-2H-pyran-4-yl)amino)pyrimidine-5-carboxylate

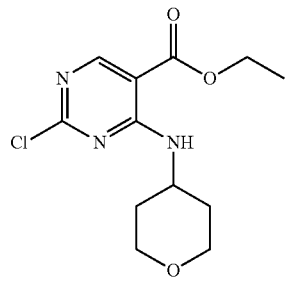 [SMILES: CCOC(=O)c1cnc(Cl)nc1NC1CCOCC1]

Potassium carbonate (62.5 g, 452 mmol) was added to ethyl 2,4-dichloropyrimidine-5-carboxylate (40 g, 181 mmol) and tetrahydro-2H-pyran-4-amine hydrochloride (24.9 g, 181 mmol) in acetonitrile (1000 mL). The reaction mixture was stirred at rt for 16 h. The precipitate was collected by filtration, washed with THF (750 mL) and the organic layers were removed under reduced pressure. The crude product was purified by fcc, elution gradient 0 to 2% THF in DCM, to afford the title compound (37.7 g, 73%) as a pale yellow solid; $^1$H NMR (400 MHz, DMSO) 1.32 (3H, t), 1.54-1.63 (2H, m), 1.85-1.89 (2H, m), 3.46 (2H, td), 3.85 (2H, dt), 4.19 (1H, dtt), 4.31 (2H, q), 8.34 (1H, d), 8.64 (1H, s); m/z MH$^+$ 286.

Intermediate 18: 2-chloro-4-((tetrahydro-2H-pyran-4-yl)amino)pyrimidine-5-carboxylic Acid

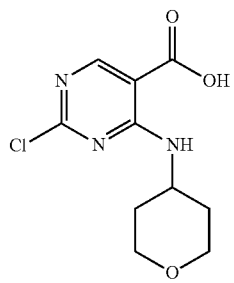 [SMILES: O=C(O)c1cnc(Cl)nc1NC1CCOCC1]

A solution of LiOH (13.1 g, 547 mmol) in water (800 mL) was added to a stirred solution of ethyl 2-chloro-4-((tetrahydro-2H-pyran-4-yl)amino)pyrimidine-5-carboxylate (78.2 g, 273 mmol) in THF (800 mL). The reaction mixture was stirred at rt for 3 h. The organic layers were removed under reduced pressure. The reaction mixture was acidified with 2 M aq. HCl. The precipitate was collected by filtration, washed with water (500 mL) and dried under vacuum to afford the title compound (66.4 g, 92%) as a white solid; $^1$H NMR (400 MHz, DMSO) 1.5-1.63 (2H, m), 1.85-1.95 (2H, m), 3.47 (2H, td), 3.85 (2H, dt), 4.08-4.26 (1H, m), 8.57 (1H, dd), 8.60 (1H, s), 13.76 (1H, s); m/z MH$^+$ 258.

Intermediate 19: 2-chloro-9-(tetrahydro-2H-pyran-4-yl)-7,9-dihydro-8H-purin-8-one

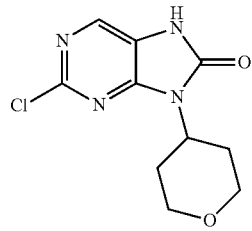

Triethylamine (25.4 g, 251 mmol) was added to 2-chloro-4-((tetrahydro-2H-pyran-4-yl)amino)pyrimidine-5-carboxylic acid (64.8 g, 251 mmol) and DPPA (69.2 g, 251 mmol) in DMA (330 mL). The reaction mixture was stirred at rt for 1 h, then was stirred at 120° C. for 16 h. The reaction mixture was poured into ice (2 L), the precipitate was collected by filtration, washed with water (400 mL) and dried under vacuum to afford the title compound (44.8 g, 70%) as a white solid; $^1$H NMR (400 MHz, DMSO) 1.66-1.70 (2H, m), 2.43 (2H, td), 3.45 (2H, t), 3.97 (2H, dd), 4.42 (1H, tt), 8.14 (1H, s), 11.65 (1H, s); m/z MH$^+$ 255.

Intermediate 20: 2-chloro-7-methyl-9-(tetrahydro-2H-pyran-4-yl)-7,9-dihydro-8H-purin-8-one

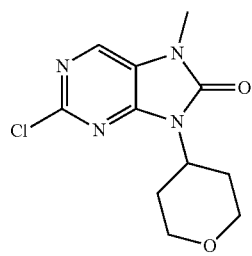

A solution of NaOH (31.0 g, 776 mmol) in water (80 mL) was added to a stirred solution of 2-chloro-9-(tetrahydro-2H-pyran-4-yl)-7,9-dihydro-8H-purin-8-one (39.5 g, 155 mmol) and MeI (48.5 mL, 776 mmol) in THF (720 mL). The reaction mixture was stirred at rt for 16 h. The organic layer was removed under reduced pressure. The reaction mixture was diluted with water. The precipitate was collected by filtration, washed with water (300 mL) and dried under vacuum to afford the title compound (32.5 g, 69%) as a white solid; $^1$H NMR (400 MHz, DMSO) 1.67-1.71 (2H, m), 2.39-2.48 (2H, m), 3.37 (3H, s), 3.46 (2H, td), 3.97 (2H, dd), 4.45 (1H, tt), 8.37 (1H, s); m/z MH$^+$ 269.

Example 3: 7-methyl-2-((7-methyl-[1,2,4]triazolo[1,5-a]pyridin-6-yl)amino)-9-(tetrahydro-2H-pyran-4-yl)-7,9-dihydro-8H-purin-8-one

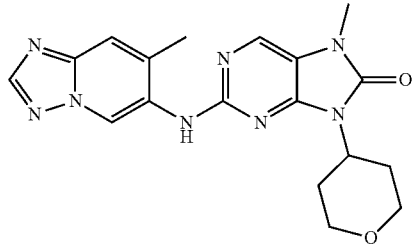 [SMILES: Cc1cc2ncnn2cc1Nc1ncc2c(n1)n(C1CCOCC1)c(=O)n2C]

Cesium carbonate (24.3 g, 74.4 mmol) was added to 2-chloro-7-methyl-9-(tetrahydro-2H-pyran-4-yl)-7,9-dihydro-8H-purin-8-one (10.0 g, 37.2 mmol) and 7-methyl-[1,2,4]triazolo[1,5-a]pyridin-6-amine (5.51 g, 37.2 mmol) in 1,4-dioxane (200 mL). Brettphos precat G3 (1.69 g, 1.86 mmol) was added and the resulting suspension was stirred vigorously at 100° C. for 1 h. Added a further 1% of catalyst and stirred for a further 30 minutes. The reaction mixture was cooled to rt, filtered and the solid was washed with 10% MeOH in DCM (100 mL). The filtrate was taken and the solvent was removed in vacuo. The resulting crude product was purified by fcc, eluting with 0-10% MeOH in DCM, then by recrystallization from MeOH and DCM to afford the title compound (7.59 g, 54%) as a cream solid; $^1$H NMR (400 MHz, DMSO) 1.63-1.72 (2H, m), 2.40 (3H, s), 2.52-2.58 (2H, m), 3.31 (3H, s), 3.42 (2H, t), 3.97 (2H, dd), 4.42 (1H, tt), 7.70 (1H, s), 8.08 (1H, s), 8.37 (1H, s), 8.65 (1H, s), 9.11 (1H, s); m/z MH$^+$ 381.

Form A

The final product, 7-methyl-2-((7-methyl-[1,2,4]triazolo[1,5-a]pyridin-6-yl)amino)-9-(tetrahydro-2H-pyran-4-yl)-7,9-dihydro-8H-purin-8-one, was analysed by XRPD and DSC and found to be crystalline. XRPD of a sample of the material gave rise to a diffraction pattern as shown in FIG. 1. 7-methyl-2-((7-methyl-[1,2,4]triazolo[1,5-a]pyridin-6-yl)amino)-9-(tetrahydro-2H-pyran-4-yl)-7,9-dihydro-8H-purin-8-one Form A is characterised by at least one peak at a 2θ value of 7.6° and 18.7°, measured using CuKα radiation. The ten most prominent peaks of the XRPD are shown in Table A.

TABLE A

Ten most prominent XRPD peaks for 7-methyl-2-((7-methyl-[1,2,4]triazolo[1,5-a]pyridin-6-yl)amino)-9-(tetrahydro-2H-pyran-4-yl)-7,9-dihydro-8H-purin-8-one Form A

| Angle 2-Theta (2θ) | Intensity % |
|---|---|
| 18.7 | 100 |
| 7.6 | 71.4 |
| 11.7 | 45.2 |
| 9.3 | 27.5 |
| 26.4 | 22.3 |
| 14.3 | 21.0 |
| 27.2 | 20.3 |
| 24.7 | 19.5 |
| 23.2 | 15.5 |
| 15.1 | 6.3 |

Example 4: 2-((2,7-dimethyl-[1,2,4]triazolo[1,5-a]pyridin-6-yl)amino)-7-methyl-9-(tetrahydro-2H-pyran-4-yl)-7,9-dihydro-8H-purin-8-one

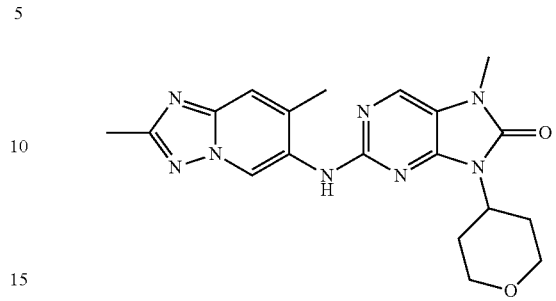

Cesium carbonate (388 mg, 1.19 mmol) was added in one portion to 2-chloro-7-methyl-9-(tetrahydro-2H-pyran-4-yl)-7,9-dihydro-8H-purin-8-one (160 mg, 0.60 mmol) and 2,7-dimethyl-[1,2,4]triazolo[1,5-a]pyridin-6-amine (97 mg, 0.60 mmol) in 1,4-dioxane (5 mL) at rt and degassed by bubbling nitrogen through the mixture for 5 minutes. Brettphos precat G3 (54.0 mg, 0.06 mmol) was added and the reaction was heated at 100° C. for 2 h. The mixture was diluted with DCM and filtered. The organic layer was evaporated and the residue was purified by fcc, elution gradient 0 to 5% MeOH in DCM, then by trituration with MeCN, to afford the title compound (125 mg, 53%) as a cream solid; $^1$H NMR (400 MHz, CDCl$_3$) 1.69-1.79 (2H, m), 2.49 (3H, s), 2.58 (3H, s), 2.76 (2H, qd), 3.41 (3H, s), 3.55 (2H, t), 4.14 (2H, dd), 4.55 (1H, tt), 6.60 (1H, s), 7.43 (1H, s), 7.87 (1H, s), 9.60 (1H, s); m/z MH$^+$ 395.

Intermediate 21: ethyl 2-chloro-4-((4-oxocyclohexyl)amino)pyrimidine-5-carboxylate

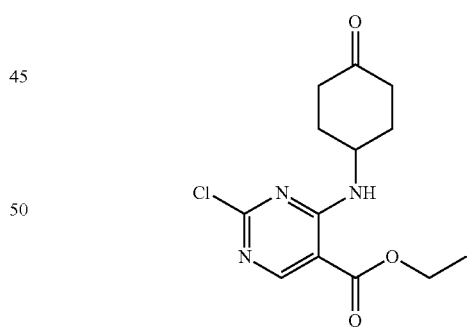

DIPEA (8.38 mL, 48.0 mmol) was added dropwise to ethyl 2,4-dichloropyrimidine-5-carboxylate (8.84 g, 40 mmol) and 4-aminocyclohexan-1-one hydrochloride (5.98 g, 40.0 mmol) in acetonitrile (200 mL) at 0° C. over a period of 2 minutes. The reaction mixture was stirred at rt for 16 h. The solvent was removed under reduced pressure. The crude product was purified by fcc, eluting with 0-5% EtOAc in DCM, to afford the title compound (6.13 g, 52%) as a white solid; $^1$H NMR (400 MHz, CDCl$_3$) 1.41 (3H, t), 1.84-1.97 (2H, m), 2.28-2.41 (2H, m), 2.44-2.62 (4H, m), 4.38 (2H, q), 4.53-4.66 (1H, m), 8.55 (1H, d), 8.72 (1H, s); m/z MH$^+$ 298.

Intermediate 22: 2-chloro-4-((4-oxocyclohexyl)amino)pyrimidine-5-carboxylic Acid

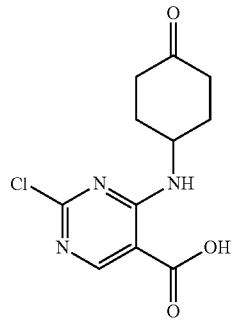 [SMILES: O=C1CCC(Nc2nc(Cl)ncc2C(=O)O)CC1]

LiOH (0.981 g, 41.0 mmol) was added in one portion to ethyl 2-chloro-4-((4-oxocyclohexyl)amino)pyrimidine-5-carboxylate (6.10 g, 20.5 mmol) in THF (50 mL) and water (50 mL) at 0° C. The reaction mixture was stirred at rt for 16 h. The organic solvent was removed under reduced pressure. The reaction mixture was acidified with 2M aq. HCl. The precipitate was collected by filtration, washed with water (20 mL) and dried in vacuo to afford the title compound (3.50 g, 63%) as a white solid, which was used without further purification; $^1$H NMR (400 MHz, DMSO) 1.79-1.93 (2H, m), 2.11-2.31 (4H, m), 2.50-2.63 (2H, m), 4.37-4.51 (1H, m), 8.60 (1H, s), 8.70 (1H, d), 13.90 (1H, s); m/z MH$^+$ 270.

Intermediate 23: 2-chloro-9-(4-oxocyclohexyl)-7,9-dihydro-8H-purin-8-one

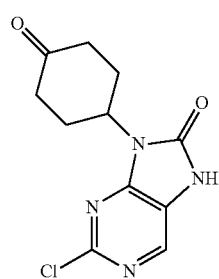 [SMILES: O=C1CCC(n2c(=O)[nH]c3cnc(Cl)nc32)CC1]

Diphenylphosphoryl azide (2.80 mL, 13.0 mmol) was added in one portion to 2-chloro-4-((4-oxocyclohexyl)amino)pyrimidine-5-carboxylic acid (3.5 g, 13.0 mmol) and Et$_3$N (1.81 mL, 13.0 mmol) in THF (70 mL) at rt. The reaction mixture was stirred at 80° C. for 16 h.

The solvent was removed under reduced pressure. The crude product was purified by fcc, eluting with 0-40% EtOAc in DCM, to afford the title compound (2.00 g, 58%) as a white solid; $^1$H NMR (400 MHz, DMSO) 2.03-2.13 (2H, m), 2.25-2.36 (2H, m), 2.51-2.65 (2H, m), 2.65-2.77 (2H, m), 4.72-4.85 (1H, m), 8.15 (1H, s), 11.68 (1H, s); m/z MH$^+$ 267.

Intermediate 24: 2-chloro-7-methyl-9-(4-oxocyclohexyl)-7,9-dihydro-8H-purin-8-one

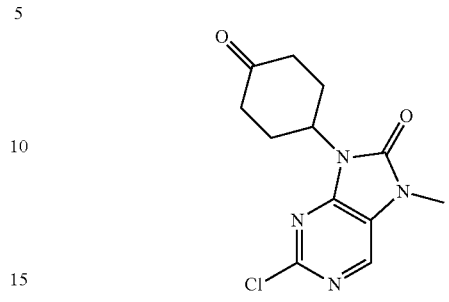

NaH (0.420 g, 10.5 mmol) was added in one portion to 2-chloro-9-(4-oxocyclohexyl)-7,9-dihydro-8H-purin-8-one (2.8 g, 10.5 mmol) in DMF (50 mL) at 0° C. The reaction mixture was stirred at rt for 30 minutes. MeI (1.97 mL, 31.5 mmol) was added and the reaction mixture was stirred at rt for 16 h. The reaction mixture was poured into water (150 mL) and the precipitate was collected by filtration, washed with water (50 mL) and dried in vacuo to afford the title compound (1.80 g, 61%) as a white solid, which was used without further purification; $^1$H NMR (400 MHz, DMSO) 2.03-2.14 (2H, m), 2.26-2.36 (2H, m), 2.53-2.65 (2H, m), 2.65-2.78 (2H, m), 3.37 (3H, s), 4.76-4.89 (1H, m), 8.38 (1H, s); m/z MH$^+$ 281.

Intermediate 25: 2-chloro-9-(4-hydroxycyclohexyl)-7-methyl-7,9-dihydro-8H-purin-8-one

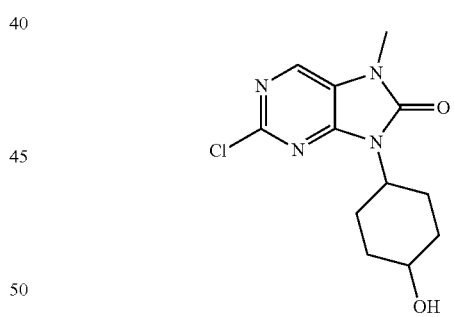

NaBH$_4$ (121 mg, 3.21 mmol) was added to 2-chloro-7-methyl-9-(4-oxocyclohexyl)-7,9-dihydro-8H-purin-8-one (900 mg, 3.21 mmol) in MeOH (15 mL). The reaction mixture was stirred at rt for 4 hours. The reaction mixture was diluted with EtOAc (100 mL), and washed with water (100 mL), The organic layer was dried over Na$_2$SO$_4$, filtered and evaporated to afford the title compound as an unknown mixture of cis and trans isomers (800 mg, 88%) as a white solid; $^1$H NMR (major isomer) (300 MHz, CDCl$_3$) 0.83-0.90 (1H, m), 1.42-1.52 (2H, m), 1.78-1.87 (2H, m), 2.11-2.17 (2H, m), 2.41-2.58 (2H, m), 3.44 (3H, s), 3.78-3.87 (1H, m), 4.33-4.44 (1H, m), 8.02 (1H, s); m/z MH$^+$ 283.

Intermediate 26: 2-chloro-9-((1s,4s)-4-methoxycyclohexyl)-7-methyl-7,9-dihydro-8H-purin-8-one

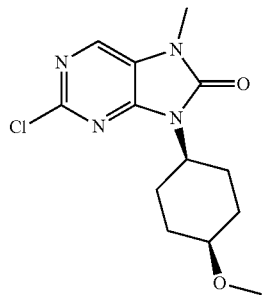 [SMILES: CO[C@H]1CC[C@@H](n2c(=O)n(C)c3cnc(Cl)nc32)CC1]

NaH (113 mg, 2.83 mmol) was added to 2-chloro-9-(4-hydroxycyclohexyl)-7-methyl-7,9-dihydro-8H-purin-8-one (800 mg, 2.83 mmol) in THF (15 mL) at 0° C. The mixture was stirred at rt for 1 h. MeI (0.531 mL, 8.49 mmol) was added. The reaction mixture was stirred at rt for 5 h. The crude product was purified by preparative HPLC to afford 2-chloro-9-((1r,4r)-4-methoxycyclohexyl)-7-methyl-7,9-dihydro-8H-purin-8-one (220 mg, 26%) as a white solid and the title compound (60 mg, 0.202 mmol, 7%) as a white solid; $^1$H NMR (400 MHz, DMSO) 1.46-1.59 (4H, m), 1.95-2.05 (2H, m), 2.37-2.48 (2H, m), 3.26 (3H, s), 3.35 (3H, s), 3.40-3.45 (1H, m), 4.22 (1H, tt), 8.34 (1H, s); m/z MH$^+$ 297.

Example 5: 9-((1s,4s)-4-methoxycyclohexyl)-7-methyl-2-((7-methyl-[1,2,4]triazolo[1,5-a]pyridin-6-yl)amino)-7,9-dihydro-8H-purin-8-one

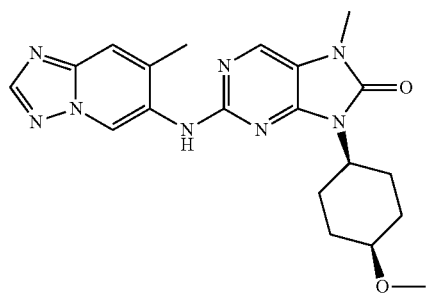 [SMILES: CO[C@H]1CC[C@@H](n2c(=O)n(C)c3cnc(Nc4cn5ncnc5cc4C)nc32)CC1]

Brettphos precat G3 (14 mg, 0.02 mmol) and 2-dicyclohexylphosphino-2',6'-di-i-propoxy-1,1'-biphenyl (7.9 mg, 0.02 mmol) were added to 2-chloro-9-((1s,4s)-4-methoxycyclohexyl)-7-methyl-7,9-dihydro-8H-purin-8-one (50 mg, 0.17 mmol), 7-methyl-[1,2,4]triazolo[1,5-a]pyridin-6-amine (25.0 mg, 0.17 mmol) and cesium carbonate (110 mg, 0.34 mmol) in 1,4-dioxane (2 mL) under nitrogen. The reaction mixture was stirred at 100° C. for 4 h. The crude product was purified by preparative HPLC to afford the title compound (0.054 g, 78%) as a white solid; $^1$H NMR (400 MHz, DMSO) 1.36-1.50 (4H, m), 1.90-1.99 (2H, m), 2.37 (3H, s), 2.38-2.50 (2H, m), 3.06 (3H, s), 3.29 (3H, s), 3.35-3.38 (1H, m), 4.10-4.23 (1H, m), 7.71 (1H, s), 8.07 (1H, s), 8.38 (1H, s), 8.66 (1H, s), 9.02 (1H, s); m/z MH$^+$ 409.

Intermediate 27: ethyl 2-chloro-4-((4-methoxycyclohexyl)amino)pyrimidine-5-carboxylate

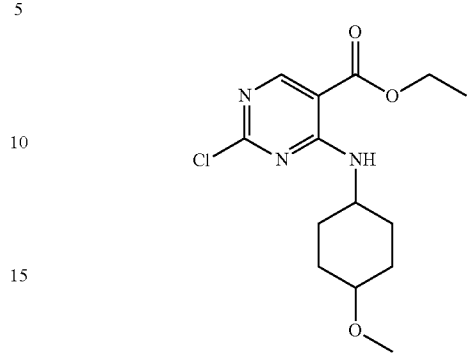

DIPEA (3.24 mL, 18.58 mmol) was added to ethyl 2,4-dichloropyrimidine-5-carboxylate (3.42 g, 15.5 mmol) and 4-methoxycyclohexan-1-amine (2.0 g, 15.5 mmol) in acetonitrile (80 mL) at 0° C. The reaction mixture was stirred at rt for 16 h. The solvent was removed to under reduced pressure. The crude product was purified by fcc, eluting with 0-5% EtOAc in petroleum ether, to afford the title compound (3.60 g, 74%) as a white solid; $^1$H NMR (400 MHz, CDCl$_3$) 1.26-1.50 (4H, m), 1.38 (3H, t), 2.02-2.18 (4H, m), 3.15-3.27 (1H, m), 3.37 (3H, s), 4.04-4.18 (1H, m), 4.35 (2H, q), 8.34 (1H, d), 8.66 (1H, s); m/z MH$^+$ 314.

Intermediate 28: 2-chloro-4-((4-methoxycyclohexyl)amino)pyrimidine-5-carboxylic Acid

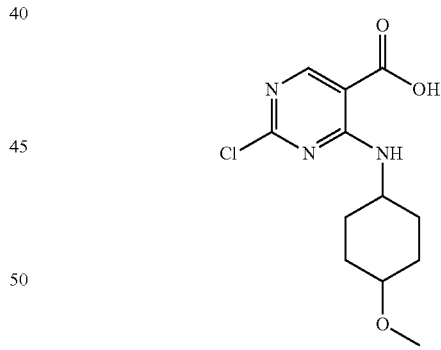

LiOH (0.549 g, 22.95 mmol) was added to ethyl 2-chloro-4-((4-methoxycyclohexyl)amino)pyrimidine-5-carboxylate (3.6 g, 11.5 mmol) in THF (25 mL) and water (25 mL) at 0° C. The reaction mixture was stirred at rt for 16 h. The organic solvent was removed under reduced pressure and the mixture was acidified with 2 M aq. HCl. The resulting precipitate was collected by filtration, washed with water (20 mL) and dried in vacuo to afford the title compound (3.10 g, 95%) as a white solid, which was used without further purification; $^1$H NMR (300 MHz, DMSO) 1.19-1.49 (4H, m), 1.91-2.04 (4H, m), 3.14-3.20 (1H, m), 3.25 (3H, s), 3.85-4.02 (1H, m), 8.51 (1H, d), 8.59 (1H, s), 13.8 (1H, s); m/z MH$^+$ 286.

Intermediate 29: 2-chloro-9-(4-methoxycyclohexyl)-7,9-dihydro-8H-purin-8-one

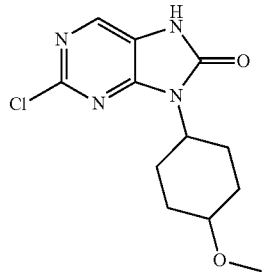 [SMILES: COC1CCC(n2c(=O)[nH]c3cnc(Cl)nc32)CC1]

Diphenylphosphoryl azide (2.34 mL, 10.9 mmol) was added to 2-chloro-4-((4-methoxycyclohexyl)amino)pyrimidine-5-carboxylic acid (3.1 g, 10.9 mmol) and Et$_3$N (1.51 mL, 10.9 mmol) in THF (50 mL) at rt. The reaction mixture was stirred at 80° C. for 16 h. The reaction mixture was diluted with water. The precipitate was collected by filtration, washed with water (150 mL) and dried under vacuum to afford the title compound (2.50 g, 82%) as a white solid, which was used without further purification; $^1$H NMR (300 MHz, DMSO) 1.21-1.35 (2H, m), 1.79 (2H, dd), 2.13 (2H, dd), 2.15-2.35 (2H, m), 3.15-3.25 (1H, m), 3.28 (3H, s), 4.09-4.26 (1H, m), 8.13 (1H, s), 11.64 (1H, s); m/z MH$^+$ 283.

Intermediate 30: 2-chloro-9-(4-methoxycyclohexyl)-7-methyl-7,9-dihydro-8H-purin-8-one

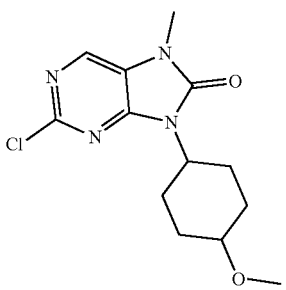 [SMILES: COC1CCC(n2c(=O)n(C)c3cnc(Cl)nc32)CC1]

NaH (0.240 g, 6.01 mmol) was added to 2-chloro-9-(4-methoxycyclohexyl)-7,9-dihydro-8H-purin-8-one (1.7 g, 6.01 mmol) in DMF (25 mL) at 0° C. under air. The reaction mixture was stirred at 0° C. for 30 minutes. MeI (1.13 mL, 18.0 mmol) was added. The reaction mixture was stirred at rt for 5 h. The reaction mixture was diluted with water. The precipitate was collected by filtration, washed with water (75 mL) and dried in vacuo to afford the title compound (1.33 g, 75%) as a white solid, which was used without further purification; $^1$H NMR (300 MHz, DMSO) 1.17-1.37 (2H, m), 1.79 (2H, dd), 2.10 (2H, dd), 2.17-2.36 (2H, m), 3.15-3.24 (1H, m), 3.27 (3H, s), 3.35 (3H, s), 4.12-4.29 (1H, m), 8.35 (1H, s); m/z MH$^+$ 297.

Example 6: 9-((1r,4r)-4-methoxycyclohexyl)-7-methyl-2-((7-methyl-[1,2,4]triazolo[1,5-a]pyridin-6-yl)amino)-7,9-dihydro-8H-purin-8-one

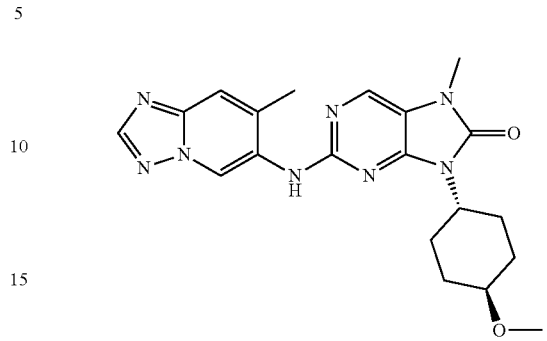

Brettphos precat G3 (45.8 mg, 0.05 mmol) was added to 2-chloro-9-(4-methoxycyclohexyl)-7-methyl-7,9-dihydro-8H-purin-8-one (150 mg, 0.51 mmol), 7-methyl-[1,2,4]triazolo[1,5-a]pyridin-6-amine (74.9 mg, 0.51 mmol) and cesium carbonate (329 mg, 1.01 mmol) in 1,4-dioxane (4 mL) under nitrogen. The reaction mixture was stirred at 100° C. for 16 h. The solvent was removed under reduced pressure. The crude product was purified by preparative HPLC to afford the title compound (136 mg, 66%) as a white solid; $^1$H NMR (400 MHz, DMSO) 1.21 (2H, qd), 1.75 (2H, dd), 2.07 (2H, dd), 2.30 (2H, qd), 2.41 (3H, s), 3.11 (1H, tt), 3.24 (3H, s), 3.30 (3H, s), 4.10-4.23 (1H, m), 7.71 (1H, s), 8.11 (1H, s), 8.38 (1H, s), 8.66 (1H, s), 9.21 (1H, s); m/z MH$^+$ 409.

Intermediate 31: ethyl 2-chloro-4-[[(3S)-tetrahydropyran-3-yl]amino]pyrimidine-5-carboxylate

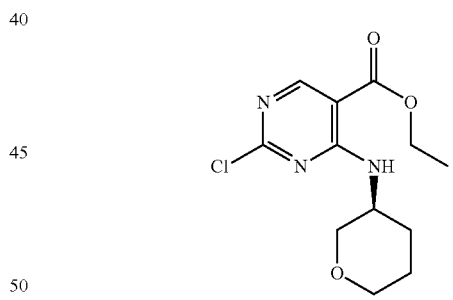

(3S)-Tetrahydro-2H-pyran-3-amine hydrochloride (1.99 g, 14.5 mmol) in MeCN (10 ml) was added dropwise to a mixture of DIPEA (6.30 ml, 36.2 mmol) and ethyl 2,4-dichloropyrimidine-5-carboxylate (3.2 g, 14.5 mmol) in MeCN (60 ml) at 0° C. over a period of 5 minutes under air. The reaction mixture was stirred for 4 h, slowly allowing to warm to rt as the ice bath melted. The reaction mixture was stirred at rt for 18 h. The reaction mixture was evaporated to dryness to remove MeCN, diluted with EtOAc (100 mL), and washed with water then sat. brine. The organic layer was dried over MgSO$_4$, filtered and evaporated to afford crude product. The crude product was purified by fcc, eluting with 0-40% EtOAc in heptane to afford the title compound (3.24 g, 78%) as a yellow oil; $^1$H NMR (400 MHz, DMSO) 1.32 (3H, t), 1.49-1.6 (1H, m), 1.63-1.79 (2H, m), 1.83-1.94 (1H, m), 3.48 (1H, dd), 3.54-3.65 (2H, m), 3.74 (1H, dd), 4.08-4.19 (1H, m), 4.33 (2H, q), 8.57 (1H, d), 8.64 (1H, s); m/z [M-H]⁻ 284.

Intermediate 32: 2-chloro-4-[[(3S)-tetrahydropyran-3-yl]amino]pyrimidine-5-carboxylic Acid

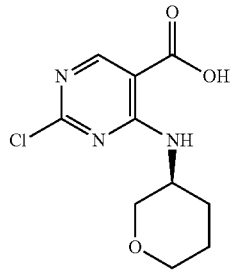 [SMILES: O=C(O)c1cnc(Cl)nc1N[C@H]1CCCOC1]

Lithium hydroxide hydrate (0.933 g, 22.23 mmol) was added in one portion to ethyl 2-chloro-4-[[(3 S)-tetrahydropyran-3-yl]amino]pyrimidine-5-carboxylate (3.24 g, 11.1 mmol) in THF (20 mL) and water (20 mL) at 0° C. The reaction mixture was stirred at rt for 16 h. The organic solvent was removed in vacuo. The reaction mixture was acidified with 2 M aq. HCl. The precipitate was collected by filtration, washed with water (50 mL) and air dried under vacuum overnight. The resulting white solid was further dried in vacuo at 50° C. for 24 h to afford the title compound (2.40 g, 84%) as a white solid; ¹H NMR (400 MHz, DMSO) 1.55 (1H, dq), 1.61-1.77 (2H, m), 1.85-1.95 (1H, m), 3.45 (1H, dd), 3.59 (2H, t), 3.75 (1H, dd), 4.06-4.16 (1H, m), 8.60 (1H, s), 8.76 (1H, d), 13.62 (1H, s); m/z MH⁺ 258.

Intermediate 33: (S)-2-chloro-9-(tetrahydro-2H-pyran-3-yl)-7,9-dihydro-8H-purin-8-one

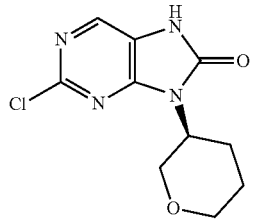 [SMILES: O=c1[nH]c2cnc(Cl)nc2n1[C@H]1CCCOC1]

Diphenylphosphoryl azide (2.00 ml, 9.29 mmol) was added in one portion to a solution of 2-chloro-4-[[(3S)-tetrahydropyran-3-yl]amino]pyrimidine-5-carboxylic acid (2.40 g, 9.29 mmol) and triethylamine (1.30 ml, 9.29 mmol) in THF (50 ml) at rt. The reaction mixture was stirred at 80° C. for 24 h. The reaction mixture was allowed to cool then was poured into water (40 mL). THF was removed in vacuo causing a white precipitate to form in the water which was filtered off under vacuum, washed with water, air dried under vacuum for 2 h, then dried in vacuo at 50° C. to afford the title compound (1.84 g, 78%) as a white solid; ¹H NMR (400 MHz, DMSO) 1.61-1.82 (2H, m), 1.88-1.99 (1H, m), 2.40-2.49 (1H, m), 3.3-3.37 (1H, m), 3.78-3.93 (3H, m), 4.2-4.32 (1H, m), 8.13 (1H, s), 11.63 (1H, s); m/z MH⁺ 255.

Intermediate 34: 2-chloro-7-methyl-9-[(3S)-tetrahydropyran-3-yl]purin-8-one

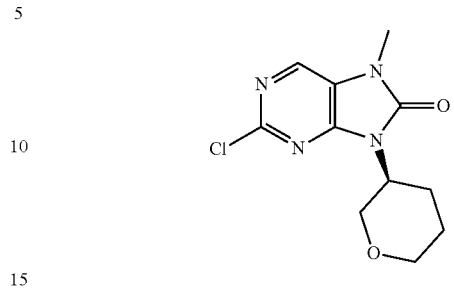

Sodium hydride (60%) (0.434 g, 10.9 mmol) was added portionwise to (S)-2-chloro-9-(tetrahydro-2H-pyran-3-yl)-7,9-dihydro-8H-purin-8-one (1.84 g, 7.24 mmol) in DMF (25 mL) at 0° C. The reaction mixture was stirred for 30 minutes then iodomethane (1.36 mL, 21.7 mmol) was added dropwise. The reaction mixture was stirred at 0° C. for 1 h. The reaction mixture was quenched with water (50 mL) and the resulting precipitate was filtered off and dried in vacuo to afford the title compound (1.62 g, 83%) as a cream solid; ¹H NMR (400 MHz, DMSO) 1.64-1.82 (2H, m), 1.90-1.98 (1H, m), 2.41-2.48 (1H, m), 3.32-3.38 (4H, m), 3.79-3.91 (3H, m), 4.25-4.34 (1H, m), 8.35 (1H, s); m/z MH⁺ 269

Example 7: (S)-7-methyl-2-((7-methyl-[1,2,4]triazolo[1,5-a]pyridin-6-yl)amino)-9-(tetrahydro-2H-pyran-3-yl)-7,9-dihydro-8H-purin-8-one

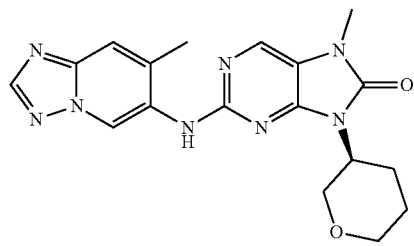 [SMILES: Cc1cc2ncnn2cc1Nc1ncc2c(n1)n([C@H]1CCCOC1)c(=O)n2C]

Cesium carbonate (303 mg, 0.93 mmol) was added to 2-chloro-7-methyl-9-[(3S)-tetrahydropyran-3-yl]purin-8-one (125 mg, 0.47 mmol) and 7-methyl-[1,2,4]triazolo[1,5-a]pyridin-6-amine (68.9 mg, 0.47 mmol) in 1,4-dioxane (4 mL). The reaction was degassed and Brettphos precat G3 (42.2 mg, 0.05 mmol) was added and the reaction mixture was stirred at 100° C. for 2 h. The reaction was cooled to rt and was concentrated. The solid was redissolved in DCM and filtered through celite. The filtrate was purified by fcc, eluting with 0-8% MeOH in DCM, and the resulting solid was triturated with diethyl ether, filtered and dried in vacuo to afford the title compound (110 mg, 62%) as an orange solid; ¹H NMR (400 MHz, DMSO) 1.62-1.74 (2H, m), 1.89 (1H, d), 2.41 (3H, s), 2.42-2.47 (1H, m), 3.19-3.26 (1H, m), 3.30 (3H, s), 3.76-3.86 (2H, m), 3.92 (1H, t), 4.22-4.32 (1H, m), 7.71 (1H, s), 8.11 (1H, s), 8.37 (1H, s), 8.65 (1H, s), 9.18 (1H, s); m/z MH⁺ 381.

Intermediate 35: ethyl 2-chloro-4-[[(3R)-tetrahydropyran-3-yl]amino]pyrimidine-5-carboxylate

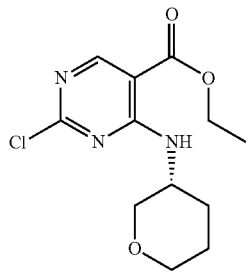 [SMILES: CCOC(=O)c1cnc(Cl)nc1N[C@@H]1CCCOC1]

(R)-tetrahydro-2H-pyran-3-amine hydrochloride (1.00 g, 7.27 mmol) in acetonitrile (5 ml) was added dropwise to a mixture of DIPEA (3.16 ml, 18.2 mmol) and ethyl 2,4-dichloropyrimidine-5-carboxylate (1.61 g, 7.27 mmol) in acetonitrile (30 ml) at 0° C. over a period of 5 minutes under air. The resulting suspension was stirred for 4 h, slowly allowing to warm to rt and stirred at rt overnight. The reaction mixture was evaporated to dryness to remove MeCN, diluted with EtOAc (100 mL), and washed with water then sat. brine. The organic layer was dried over MgSO$_4$, filtered and evaporated. The resulting crude product was purified by fcc, elution gradient 0 to 50% EtOAc in heptane, to afford the title compound (0.936 g, 45%) as a yellow oil; $^1$H NMR (400 MHz, DMSO) 1.33 (3H, t), 1.57 (1H, dt), 1.71 (2H, dtd), 1.91 (1H, ddt), 3.48 (1H, dd), 3.55-3.66 (2H, m), 3.75 (1H, dd), 4.11-4.2 (1H, m), 4.33 (2H, q), 8.58 (1H, d), 8.65 (1H, s); m/z MH$^+$ 286.

Intermediate 36: 2-chloro-4-[[(3R)-tetrahydropyran-3-yl]amino]pyrimidine-5-carboxylic Acid

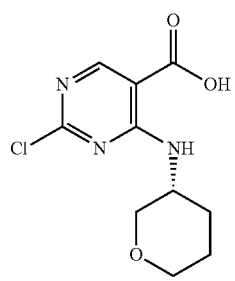 [SMILES: O=C(O)c1cnc(Cl)nc1N[C@@H]1CCCOC1]

Lithium hydroxide hydrate (276 mg, 6.57 mmol) was added in one portion to ethyl 2-chloro-4-[[(3R)-tetrahydropyran-3-yl]amino]pyrimidine-5-carboxylate (939 mg, 3.29 mmol) in THF (1.23 mL) and water (4.10 mL) at rt. The reaction mixture was stirred at rt for 30 minutes. The organic solvent was removed under reduced pressure. The reaction mixture was acidified with 2 M aq. HCl. The resulting white solid was filtered to afford the title compound (806 mg, 95%) as a white solid which was dried in vacuo at 45° C. overnight; $^1$H NMR (400 MHz, DMSO) 1.56 (1H, dq), 1.70 (2H, ddt), 1.91 (1H, ddt), 3.46 (1H, dd), 3.60 (2H, t), 3.76 (1H, dd), 4.12 (1H, d), 8.61 (1H, s), 8.77 (1H, d); m/z MH$^+$ 258.

Intermediate 37: 2-chloro-9-[(3R)-tetrahydropyran-3-yl]-7H-purin-8-one

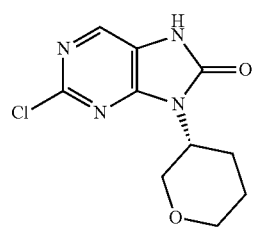

Diphenylphosphoryl azide (0.674 mL, 3.13 mmol) was added in one portion to a solution of 2-chloro-4-[[(3R)-tetrahydropyran-3-yl]amino]pyrimidine-5-carboxylic acid (806 mg, 3.13 mmol) and triethylamine (0.436 mL, 3.13 mmol) in THF (17.3 mL) at rt. The reaction mixture was stirred at 80° C. for 24 h, then was allowed to cool and poured into water (20 mL). The THF was removed in vacuo causing a white precipitate to form in the water. The precipitate was collected by filtration and dried in vacuo to afford the title compound (565 mg, 71%) as a white solid; $^1$H NMR (400 MHz, DMSO) 1.64-1.83 (2H, m), 1.93 (1H, d), 2.42-2.49 (1H, m), 3.35 (1H, dd), 3.8-3.92 (3H, m), 4.21-4.36 (1H, m), 8.13 (1H, s), 11.6 (1H, s); m/z MH$^+$ 255.

Intermediate 38: 2-chloro-7-methyl-9-[(3R)-tetrahydropyran-3-yl]purin-8-one

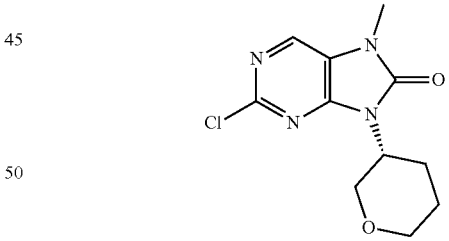

Sodium hydride (60%) (133 mg, 3.33 mmol) was added portionwise to 2-chloro-9-[(3R)-tetrahydropyran-3-yl]-7H-purin-8-one (565 mg, 2.22 mmol) in DMF (5.13 mL) at 0° C. The reaction mixture was stirred for 30 minutes then iodomethane (416 μL, 6.66 mmol) was added dropwise. The reaction mixture was stirred at ice bath temperature for 1 h. The reaction mixture was quenched with water (50 mL) and the resulting precipitate was filtered off and dried overnight to afford the title compound (535 mg, 90%) as a white solid which was used directly in the next step; $^1$H NMR (400 MHz, DMSO) 1.73 (2H, dddd), 1.94 (1H, d), 2.41-2.49 (1H, m), 3.34-3.38 (1H, m), 3.36 (3H, s), 3.81-3.92 (3H, m), 4.24-4.36 (1H, m), 8.36 (1H, s); m/z MH$^+$ 269.

Example 8: (R)-7-methyl-2-((7-methyl-[1,2,4]triazolo[1,5-a]pyridin-6-yl)amino)-9-(tetrahydro-2H-pyran-3-yl)-7,9-dihydro-8H-purin-8-one

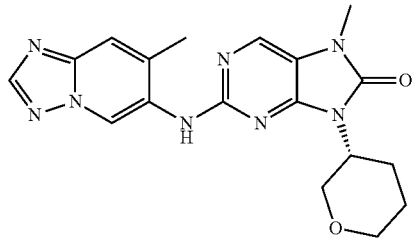 [SMILES: Cc1cc2ncnn2cc1Nc1ncc2c(n1)n([C@@H]1CCCOC1)c(=O)n2C]

Cesium carbonate (364 mg, 1.12 mmol) was added in one portion to 7-methyl-[1,2,4]triazolo[1,5-a]pyridin-6-amine (83 mg, 0.56 mmol) and 2-chloro-7-methyl-9-[(3R)-tetrahydropyran-3-yl]purin-8-one (150 mg, 0.56 mmol) in 1,4-dioxane (5 mL) at rt and degassed by bubbling nitrogen through the mixture for 5 minutes. Brettphos precat G3 (51 mg, 0.06 mmol) was added and the reaction was heated at 100° C. for 2 h. The mixture was diluted with DCM and filtered. The DCM layer was evaporated and the residue was purified by fcc, elution gradient 0 to 5% MeOH in DCM, then triturated with MeCN, filtered and dried in vacuo to afford the title compound (92 mg, 43%) as a cream solid; $^1$H NMR (400 MHz, DMSO) 1.59-1.77 (2H, m), 1.90 (1H, d), 2.41 (3H, s), 2.43-2.49 (1H, m), 3.25 (1H, td), 3.31 (3H, s), 3.76-3.88 (2H, m), 3.92 (1H, t), 4.27 (1H, ddt), 7.72 (1H, s), 8.12 (1H, s), 8.37 (1H, s), 8.66 (1H, s), 9.19 (1H, s); m/z MH$^+$ 381.

Intermediate 39: 2-chloro-9-(4-hydroxy-4-methylcyclohexyl)-7-methyl-7,9-dihydro-8H-purin-8-one

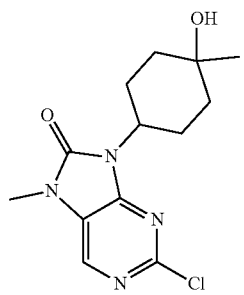

Methyl magnesium bromide (3M, 0.89 mL, 2.67 mmol) was added to 2-chloro-7-methyl-9-(4-oxocyclohexyl)-7,9-dihydro-8H-purin-8-one (500 mg, 1.78 mmol) in THF (10 mL) at 0° C. under nitrogen. The reaction mixture was stirred at rt for 4 h. The solvent was removed under reduced pressure. The crude product was purified by preparative HPLC to afford the title compound (400 mg, 76%) as a white solid (mixture of diastereoisomers); $^1$H NMR (major diastereoisomer) (300 MHz, CDCl$_3$) 1.30 (3H, s), 1.47 (1H, s), 1.51-1.74 (4H, m), 1.76-92 (2H, m), 2.62-2.83 (2H, m), 3.44 (3H, s), 4.26-4.50 (1H, m), 8.01 (1H, s); m/z MH$^+$ 297.

Example 9: 9-((1r,4r)-4-hydroxy-4-methylcyclohexyl)-7-methyl-2-((7-methyl-[1,2,4]triazolo[1,5-a]pyridin-6-yl)amino)-7,9-dihydro-8H-purin-8-one
and
Example 10: 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one

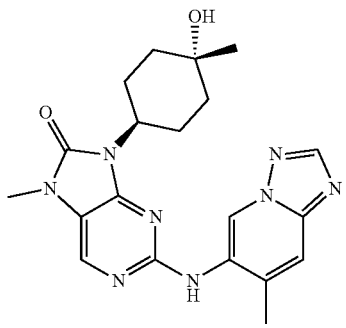
Example 9

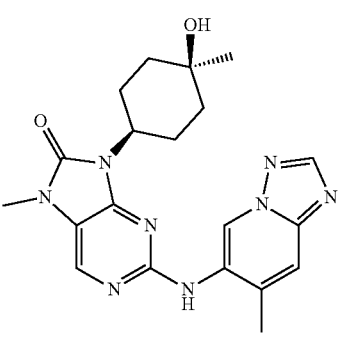
Example 10

Brettphos precat G3 (169 mg, 0.20 mmol) and 2-dicyclohexylphosphino-2',6'-di-i-propoxy-1,1'-biphenyl (94 mg, 0.20 mmol) were added to 2-chloro-9-(4-hydroxy-4-methylcyclohexyl)-7-methyl-7,9-dihydro-8H-purin-8-one (300 mg, 1.01 mmol), 7-methyl-[1,2,4]triazolo[1,5-a]pyridin-6-amine (180 mg, 1.21 mmol) and cesium carbonate (659 mg, 2.02 mmol) in 1,4-dioxane (5 mL) under nitrogen. The reaction mixture was stirred at 100° C. for 5 h. The crude product was purified by preparative HPLC to afford 9-((1r,4r)-4-hydroxy-4-methylcyclohexyl)-7-methyl-2-((7-methyl-[1,2,4]triazolo[1,5-a]pyridin-6-yl)amino)-7,9-dihydro-8H-purin-8-one (73 mg, 18%) as a white solid; $^1$H NMR (400 MHz, DMSO) 0.66 (3H, s), 1.33-1.45 (2H, m), 1.45-1.57 (4H, m), 2.11-2.27 (2H, m), 2.33 (3H, s), 3.29 (3H, s), 3.99-4.13 (1H, m), 4.33 (1H, s), 7.71 (1H, s), 8.10 (1H, s), 8.38 (1H, s), 8.70 (1H, s), 8.97 (1H, s); m/z MH$^+$ 409; and 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one (190 mg, 46%) as a white solid; $^1$H NMR (400 MHz, DMSO) 1.15 (3H, s), 1.34-1.51 (4H, m), 1.66 (2H, d), 2.39 (3H, s), 2.57-2.73 (2H, m), 3.29 (3H, s), 4.04 (1H, s), 4.08-4.21 (1H, m), 7.70 (1H, s), 8.05 (1H, s), 8.38 (1H, s), 8.59 (1H, s), 9.14 (1H, s); m/z MH$^+$ 409.

Form A

The final product, 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one, was analysed by XRPD and DSC and found to be crystalline. XRPD of a sample of the material gave rise to a diffraction pattern as shown in FIG. 3. 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one Form A is characterised by at least one peak at a 2θ value of 8.8° and 12.7°, measured using CuKα radiation. The ten most prominent peaks of the XRPD are shown in Table B.

TABLE B

Ten most prominent XRPD peaks for 9-((1s,4s)-4-hydroxy-4-methylcyclohexyl)-7-methyl-2-((7-methyl-[1,2,4]triazolo-[1,5-a]pyridin-6-yl)amino)-7,9-dihydro-8H-purin-8-one Form A.

| Angle 2-Theta (2θ) | Intensity % |
|---|---|
| 12.7 | 100 |
| 14.8 | 83.3 |
| 8.8 | 82.3 |
| 23.8 | 57.4 |
| 16.5 | 53.1 |
| 5.1 | 43.6 |
| 13.0 | 42.6 |
| 10.3 | 42 |
| 13.8 | 40.3 |
| 24.2 | 38.6 |

Intermediate 40: ethyl 2-chloro-4-[[(3S)-tetrahydrofuran-3-yl]amino]pyrimidine-5-carboxylate

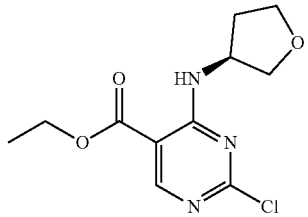 [SMILES: CCOC(=O)c1cnc(Cl)nc1N[C@H]1CCOC1]

DIPEA (4.74 mL, 27.1 mmol) was added dropwise to ethyl 2,4-dichloropyrimidine-5-carboxylate (5 g, 22.6 mmol) and (S)-tetrahydrofuran-3-amine (1.97 g, 22.6 mmol) in acetonitrile (100 mL) at 0° C. over a period of 2 min. The reaction mixture was allowed to warm to rt then was stirred at rt for 16 h and concentrated in vacuo. The resulting crude product was purified by fcc, elution gradient 0 to 5% EtOAc in petroleum ether, to afford the title compound (4.60 g, 75%) as a white solid; $^1$H NMR (400 MHz, DMSO) 1.32 (3H, t), 1.83-1.95 (1H, m), 2.21-2.35 (1H, m), 3.65 (1H, dd), 3.69-3.92 (3H, m), 4.27-4.37 (2H, m), 4.57-4.68 (1H, m), 8.44 (1H, d), 8.63 (1H, s); m/z MH$^+$ 272.

Intermediate 41: 2-chloro-4-[[(3S)-tetrahydrofuran-3-yl]amino]pyrimidine-5-carboxylic Acid

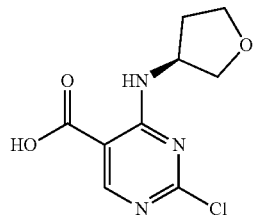 [SMILES: O=C(O)c1cnc(Cl)nc1N[C@H]1CCOC1]

LiOH (0.811 g, 33.9 mmol) was added in one portion to ethyl 2-chloro-4-[[(3S)-tetrahydrofuran-3-yl]amino]pyrimidine-5-carboxylate (4.60 g, 16.93 mmol) in THF (50 mL) and water (25 mL) at 0° C. The reaction mixture was allowed to warm to rt, stirred at rt for 2 h, partially concentrated in vacuo and acidified with 2 M aq. HCl. The resulting precipitate was isolated by filtration, washed with water (20 mL) and dried in vacuo to afford the title compound (3.50 g, 85%) as a white solid; $^1$H NMR (400 MHz, DMSO) 1.81-1.93 (1H, m), 2.21-2.35 (1H, m), 3.60-3.68 (1H, m), 3.69-3.94 (3H, m), 4.56-4.68 (1H, m), 8.61 (1H, s), 8.65 (1H, s) 13.84 (1H, s); m/z MH$^+$ 244.

Intermediate 42: 2-chloro-9-[(3S)-tetrahydro-3-furanyl]-7,9-dihydro-8H-purin-8-one

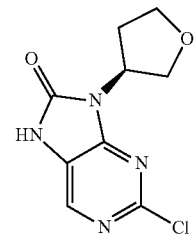 [SMILES: O=c1[nH]c2cnc(Cl)nc2n1[C@H]1CCOC1]

Diphenylphosphoryl azide (3.10 mL, 14.37 mmol) was added in one portion to 2-chloro-4-[[(3S)-tetrahydrofuran-3-yl]amino]pyrimidine-5-carboxylic acid (3.5 g, 14.4 mmol) and Et$_3$N (2.00 mL, 14.4 mmol) in THF (100 mL) at rt. The reaction mixture was heated at 80° C. for 2 days. The solvent was removed under reduced pressure. The resulting crude product was purified by fcc, elution gradient 0 to 50% EtOAc in petroleum ether, to afford the title compound (3.20 g, 93%) as a white solid; $^1$H NMR (400 MHz, DMSO) 2.16-2.32 (1H, m), 2.35-2.48 (1H, m), 3.81-3.92 (2H, m), 3.97 (1H, t), 4.10 (1H, q), 4.91-5.03 (1H, m), 8.14 (1H, s), 11.66 (1H, s); m/z MH$^+$ 241.

Intermediate 43: 2-chloro-7-methyl-9-[(3S)-tetrahydro-3-furanyl]-7,9-dihydro-8H-purin-8-one

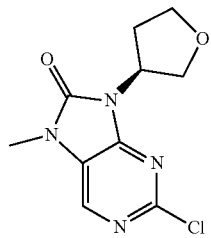 [SMILES: Cn1c(=O)n([C@H]2CCOC2)c2nc(Cl)ncc21]

NaH (0.532 g, 13.30 mmol) was added in one portion to 2-chloro-9-[(3S)-tetrahydro-3-furanyl]-7,9-dihydro-8H-purin-8-one (3.2 g, 13.30 mmol) in DMF (30 mL) at 0° C. The reaction mixture was stirred at rt for 30 min. MeI (2.49 mL, 39.9 mmol) was added. The reaction mixture was stirred at rt for 16 h, then was quenched with water (5 mL) and concentrated in vacuo. The crude product was purified by fcc, elution gradient 0 to 40% EtOAc in petroleum ether, to afford the title compound (2.90 g, 86%) as a yellow solid; $^1$H NMR (400 MHz, DMSO) 2.18-2.32 (1H, m), 2.35-2.48 (1H, m), 3.36 (3H, s), 3.82-3.94 (2H, m), 3.98 (1H, t), 4.11 (1H, q), 4.95-5.07 (1H, m), 8.36 (1H, s); m/z MH$^+$ 255.

Example 11: (S)-7-methyl-2-((7-methyl-[1,2,4]triazolo[1,5-a]pyridin-6-yl)amino)-9-(tetrahydrofuran-3-yl)-7,9-dihydro-8H-purin-8-one

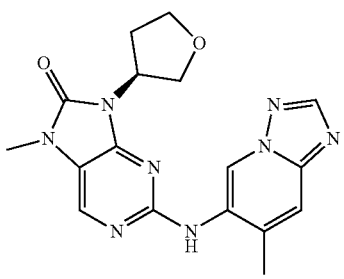 [SMILES: Cc1cc2ncnn2cc1Nc1ncc2c(n1)n([C@H]1CCOC1)c(=O)n2C]

RuPhos Pd (13.96 mg, 0.02 mmol) was added to 2-chloro-7-methyl-9-[(3S)-tetrahydro-3-furanyl]-7,9-dihydro-8H-purin-8-one (85 mg, 0.33 mmol), 7-methyl-[1,2,4]triazolo[1,5-a]pyridin-6-amine (49.5 mg, 0.33 mmol), RuPhos (15.57 mg, 0.03 mmol) and Cs$_2$CO$_3$ (326 mg, 1.00 mmol) in 1,4-dioxane (1 mL). The reaction mixture was stirred at 100° C. for 16 h, then allowed to cool to rt and concentrated in vacuo. The resulting crude product was purified by flash C18 chromatography, elution gradient 0 to 55% MeOH in water with 0.1% formic acid to afford the title compound (87 mg, 71%) as a white solid; $^1$H NMR (300 MHz, CD$_3$OD) 2.30-2.40 (1H, m), 2.47-2.55 (1H, m), 2.51 (3H, s), 3.42 (3H, s), 3.87 (1H, q), 4.00-4.14 (2H, m), 4.20 (1H, q), 5.02-5.30 (1H, m), 7.64 (1H, s), 8.07 (1H, s), 8.33 (1H, s), 9.43 (1H, s), NH proton not observed; m/z MH$^+$ 367.

Intermediate 44: ethyl 2-chloro-4-((4-hydroxy-1-methylcyclohexyl)amino)pyrimidine-5-carboxylate

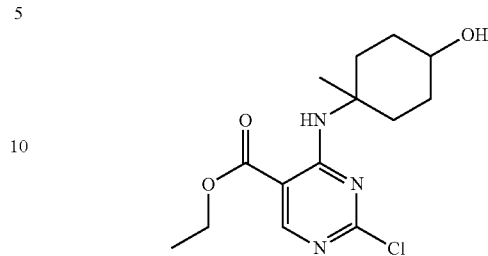

DIPEA (4.28 mL, 24.5 mmol) was added dropwise to ethyl 2,4-dichloropyrimidine-5-carboxylate (2.46 g, 11.1 mmol) and 4-amino-4-methyl-cyclohexanol hydrochloride (2.00 g, 11.1 mmol) in acetonitrile (40 mL) at 0° C. over 5 min. The reaction mixture was allowed to warm to rt, then was stirred at rt for 6 h and concentrated in vacuo, diluted with EtOAc (300 mL) and washed with sat. brine (100 mL×2). The organic layer was isolated and dried over MgSO$_4$ and concentrated in vacuo. The resulting crude product was purified by fcc, elution gradient 0 to 20% EtOAc in n-heptane, to afford the title compound (2.82 g, 81%) as a pale yellow gum; $^1$H NMR (400 MHz, DMSO) 1.36-1.44 (3H, m), 1.44-1.58 (6H, m), 1.57-1.71 (1H, m), 1.72-2.13 (3H, m), 2.41-2.54 (2H, m), 3.63-3.75 (1H, m), 4.36 (2H, q), 8.52-8.59 (1H, m), 8.67 (1H, d); m/z MH$^+$ 314.

Intermediate 45: 2-chloro-4-((4-hydroxy-1-methylcyclohexyl)amino)pyrimidine-5-carboxylic Acid

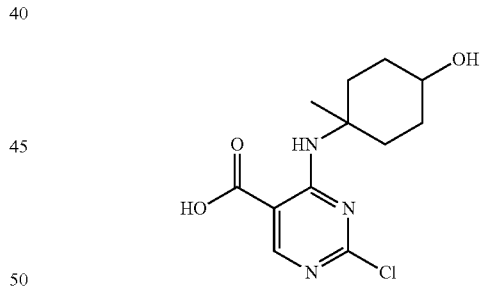

LiOH (0.43 g, 17.97 mmol) was added in one portion to ethyl 2-chloro-4-((4-hydroxy-1-methylcyclohexyl)amino)pyrimidine-5-carboxylate (2.82 g, 8.99 mmol) in THF (25 mL) and water (25 mL) at 0° C. The reaction mixture was allowed to warm to rt and was stirred at rt for 5 h, then was partially concentrated in vacuo and acidified with 2 M aq. HCl. The resulting precipitate was isolated by filtration, washed with water (20 mL) and dried in vacuo to afford the title compound (2.17 g, 85%) as a white solid; $^1$H NMR (400 MHz, DMSO) 1.18-1.32 (2H, m), 1.34-1.52 (2H, m), 1.43 (3H, s), 1.52-1.79 (2H, m), 2.21-2.30 (2H, m), 3.37-3.49 (1H, m), 4.55 (1H, s), 8.59 (1H, d), 8.74 (1H, s), 13.85 (1H, s); m/z MH$^+$ 286.

Intermediate 46: 2-chloro-9-(4-hydroxy-1-methylcyclohexyl)-7,9-dihydro-8H-purin-8-one

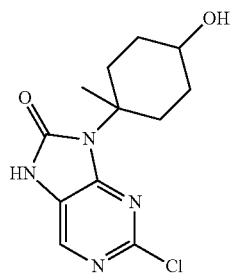 [SMILES: CC1(n2c(=O)[nH]c3cnc(Cl)nc32)CCC(O)CC1]

Diphenylphosphoryl azide (1.64 mL, 7.59 mmol) was added in one portion to 2-chloro-4-((4-hydroxy-1-methylcyclohexyl)amino)pyrimidine-5-carboxylic acid (2.17 g, 7.59 mmol) and Et$_3$N (1.06 mL, 7.59 mmol) in THF (20 mL) at rt. The reaction mixture was heated at 80° C. for 2 days, then was concentrated in vacuo. The resulting crude product was purified by fcc, elution gradient 0 to 50% EtOAc in DCM, to afford the title compound (1.79 g, 83%) as a white solid; $^1$H NMR (400 MHz, DMSO) 1.09-1.25 (2H, m), 1.34 (3H, s), 1.36-1.64 (2H, m), 1.65-1.77 (2H, m), 3.17 (2H, d), 3.41-3.57 (1H, m), 4.07-4.15 (1H, m), 8.10 (1H, d), 11.61 (1H, s); m/z MH$^+$ 283.

Intermediates 47 and 48: 2-chloro-9-((1s,4s)-4-hydroxy-1-methylcyclohexyl)-7-methyl-7,9-dihydro-8H-purin-8-one and 2-chloro-9-((1r,4r)-4-hydroxy-1-methylcyclohexyl)-7-methyl-7,9-dihydro-8H-purin-8-one

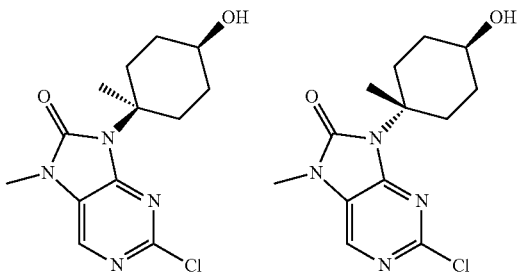 [SMILES: Cn1c(=O)n([C@]2(C)CC[C@H](O)CC2)c2nc(Cl)ncc21 ; Cn1c(=O)n([C@]2(C)CC[C@@H](O)CC2)c2nc(Cl)ncc21]

A solution of NaOH (1.27 g, 31.66 mmol) in water (24 mL) was added to a stirred mixture of 2-chloro-9-(4-hydroxy-1-methylcyclohexyl)-7,9-dihydro-8H-purin-8-one (1.79 g, 6.33 mmol), iodomethane (1.97 mL, 31.66 mmol) and tetrabutylammonium bromide (0.204 g, 0.63 mmol) in DCM (40 mL) at rt. The reaction mixture was stirred at rt for 16 h, then was extracted with DCM (3×50 mL). The combined organic layers were dried over MgSO$_4$, filtered and concentrated in vacuo. The resulting crude product was purified by fcc, elution gradient 0 to 40% EtOAc in DCM, to afford the title compounds:

Minor product 2-chloro-9-((1 s,4s)-4-hydroxy-1-methylcyclohexyl)-7-methyl-7,9-dihydro-8H-purin-8-one (0.26 g, 14%) as a white solid; $^1$H NMR (400 MHz, CDCl$_3$) 1.66 (3H, s), 1.67-1.85 (4H, m), 2.19-2.31 (2H, m), 2.91-3.02 (2H, m), 3.41 (3H, s), 3.89-3.99 (1H, m), 7.99 (1H, s), one exchangeable proton not observed; m/z MH$^+$ 297.

Major product 2-chloro-9-((1 r,4r)-4-hydroxy-1-methylcyclohexyl)-7-methyl-7,9-dihydro-8H-purin-8-one (1.44 g, 77%) as a white solid; $^1$H NMR (400 MHz, CDCl$_3$) 1.42-1.50 (2H, m), 1.51 (3H, s), 1.58-1.88 (2H, m), 1.88-2.00 (2H, m), 3.40 (3H, s), 3.52-3.63 (2H, m), 3.72-3.84 (1H, m), 7.99 (1H, s), one exchangeable proton not observed; m/z MH$^+$ 297.

Example 12: 9-((1s,4s)-4-hydroxy-1-methylcyclohexyl)-7-methyl-2-((7-methyl-[1,2,4]triazolo[1,5-a]pyridin-6-yl)amino)-7,9-dihydro-8H-purin-8-one

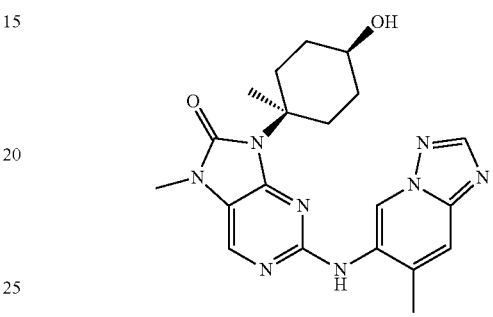

RuPhos Pd (5.64 mg, 6.74 µmol) was added to 2-chloro-9-((1s,4s)-4-hydroxy-1-methylcyclohexyl)-7-methyl-7,9-dihydro-8H-purin-8-one (40 mg, 0.13 mmol), 7-methyl-[1,2,4]triazolo[1,5-a]pyridin-6-amine (22 mg, 0.15 mmol), Cs$_2$CO$_3$ (132 mg, 0.40 mmol) and RuPhos (6.3 mg, 0.01 mmol) in 1,4-dioxane (4 mL). The reaction mixture was stirred at 100° C. for 3 h, allowed to cool to rt and concentrated in vacuo. The crude product was purified by flash C18-flash chromatography, elution gradient 0 to 90% MeOH in water eluent with 0.1% formic acid, then further purified by preparative HPLC, to afford the title compound (20 mg, 36%) as a white solid; $^1$H NMR (300 MHz, DMSO) 1.34-1.43 (2H, m), 1.43 (3H, s), 1.50-1.58 (2H, m), 1.96 (2H, t), 2.38 (3H, s), 2.78-2.83 (2H, m), 3.26 (3H, s), 3.60-3.61 (1H, m), 4.40 (1H, d), 7.70 (1H, m), 8.09 (1H, s), 8.37 (1H, s), 8.55 (1H, s), 9.04 (1H, s); m/z MH$^+$ 409.

Intermediate 49: ethyl 2-chloro-4-(cyclohexylamino)pyrimidine-5-carboxylate

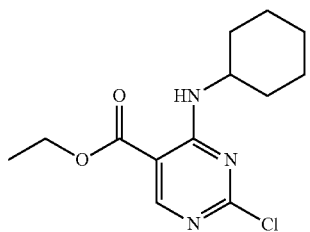 [SMILES: CCOC(=O)c1cnc(Cl)nc1NC1CCCCC1]

Cyclohexanamine (4.92 ml, 43.0 mmol) in acetonitrile (30 mL) was added dropwise to a mixture of DIPEA (11.2 mL, 64.5 mmol) and ethyl 2,4-dichloropyrimidine-5-carboxylate (9.5 g, 43.0 mmol) in acetonitrile (200 mL) at 0° C. over a period of 5 min under air. The reaction mixture was stirred at 0° C. for 4 h, slowly allowing to warm to room temperature as the ice bath melted. The reaction mixture was concentrated in vacuo, diluted with EtOAc (200 mL), and washed with water (75 mL) and sat. brine (50 mL). The organic layer was dried over MgSO₄ and concentrated in vacuo. The resulting crude product was purified by fcc, elution gradient 0 to 50% EtOAc in heptane, to afford the title compound (8.84 g, 73%) as a colourless oil which solidified on standing; $^1$H NMR (400 MHz, CDCl₃) 1.24-1.35 (3H, m), 1.38 (3H, t), 1.38-1.51 (2H, m), 1.63 (1H, dt), 1.75 (2H, dq), 1.92-2.02 (2H, m), 4.06-4.21 (1H, m), 4.35 (2H, q), 8.36 (1H, d), 8.64 (1H, s); m/z: MH⁺ 284.

Intermediate 50: 2-chloro-4-(cyclohexylamino)pyrimidine-5-carboxylic Acid

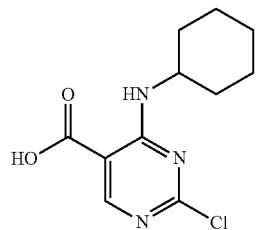 [SMILES: O=C(O)c1cnc(Cl)nc1NC1CCCCC1]

Lithium hydroxide hydrate (2.61 g, 62.3 mmol) was added in one portion to ethyl 2-chloro-4-(cyclohexylamino)pyrimidine-5-carboxylate (8.84 g, 31.2 mmol) in THF (50 mL) and water (50 mL) at 0° C. The reaction mixture was stirred at rt for 16 h, then was partially concentrated in vacuo, and acidified with 2 M aq. HCl. The resulting precipitate was collected by filtration, washed with water (50 mL) and dried in vacuo at 50° C. for 2 days to afford the title compound (7.58 g, 95%) as a white solid; $^1$H NMR (400 MHz, DMSO) 1.18-1.45 (5H, m), 1.52-1.62 (1H, m), 1.64-1.73 (2H, m), 1.83-1.95 (2H, m), 3.91-4.04 (1H, m), 8.54-8.6 (2H, m), 13.74 (1H, s); m/z: MH⁺ 256.

Intermediate 51: 2-chloro-9-cyclohexyl-7,9-dihydro-8H-purin-8-one

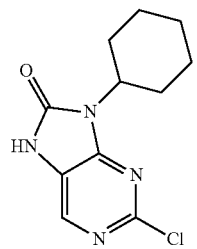 [SMILES: O=c1[nH]c2cnc(Cl)nc2n1C1CCCCC1]

Diphenylphosphoryl azide (6.39 ml, 29.6 mmol) was added in one portion to a solution of 2-chloro-4-(cyclohexylamino)pyrimidine-5-carboxylic acid (7.58 g, 29.6 mmol) and triethylamine (4.1 ml, 29.6 mmol) in THF (150 ml) at rt. The reaction mixture was stirred at 80° C. for 26 h. The reaction mixture was allowed to cool to rt then poured into water (80 mL), and the resulting mixture was partially concentrated in vacuo. The resulting precipitate was collected by filtration, washed with water and dried in vacuo overnight at 50° C. to afford the title compound (7.69 g, 103%) as a white solid; $^1$H NMR (400 MHz, DMSO) 1.12-1.27 (1H, m), 1.36 (2H, qd), 1.63-1.7 (1H, m), 1.71-1.79 (2H, m), 1.79-1.88 (2H, m), 2.18 (2H, qd), 4.14 (1H, tt), 8.11 (1H, s), 11.57 (1H, s); m/z MH⁺ 253.

Intermediate 52: 2-chloro-9-cyclohexyl-7-methyl-7,9-dihydro-8H-purin-8-one

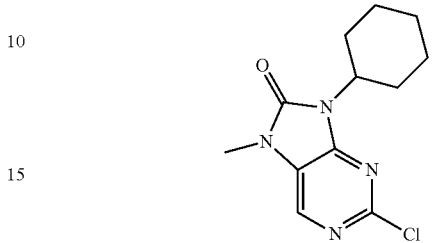

Sodium hydride (60%) (0.261 g, 6.53 mmol) was added portionwise to 2-chloro-9-cyclohexyl-7,9-dihydro-8H-purin-8-one (1.1 g, 4.35 mmol) in DMF (10 mL) at 0° C. The reaction mixture was stirred for 30 min then iodomethane (0.817 mL, 13.16 mmol) was added dropwise. The reaction mixture was stirred at 0° C. for 1 h, then was quenched with water (50 mL) and the resulting precipitate was collected by filtration and dried in vacuo overnight to afford the title compound (1.08 g, 93%) as a cream solid; $^1$H NMR (400 MHz, DMSO) 1.21 (1H, ddd), 1.38 (2H, tdd), 1.65 (1H, d), 1.74 (2H, d), 1.83 (2H, d), 2.09-2.26 (2H, m), 3.30 (3H, s), 4.18 (1H, tt), 8.34 (1H, s); m/z MH⁺ 267.

Example 13: 9-cyclohexyl-7-methyl-2-((7-methyl-[1,2,4]triazolo[1,5-a]pyridin-6-yl)amino)-7,9-dihydro-8H-purin-8-one

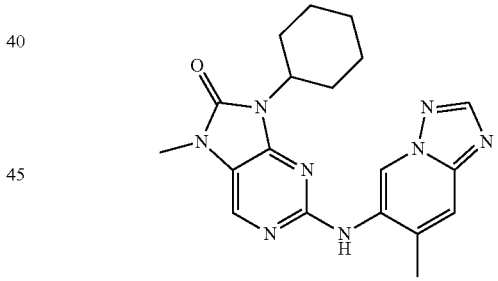

Cesium carbonate (733 mg, 2.25 mmol) was added in one portion to 2-chloro-9-cyclohexyl-7-methyl-7,9-dihydro-8H-purin-8-one (300 mg, 1.12 mmol) and 7-methyl-[1,2,4]triazolo[1,5-a]pyridin-6-amine (167 mg, 1.12 mmol) in 1,4-dioxane (8 mL) at rt. The reaction was degassed by bubbling nitrogen through the mixture for 5 min. Brettphos precat G3 (102 mg, 0.11 mmol) was added and the reaction was heated at 100° C. for 2 h. The mixture was diluted with DCM and filtered. The filtrate was concentrated in vacuo and the residue was purified by fcc, elution gradient 0 to 5% MeOH in DCM, then further purified by trituration with MeCN and dried in vacuo at 45° C. overnight to afford the title compound (233 mg, 55%) as a cream solid; $^1$H NMR (400 MHz, DMSO) 1.16 (1H, q), 1.33 (2H, q), 1.62 (1H, d), 1.71 (2H, d), 1.80 (2H, d), 2.14-2.3 (2H, m), 2.42 (3H, s), 3.31 (3H, s), 4.16 (1H, ddd), 7.71 (1H, s), 8.11 (1H, s), 8.37 (1H, s), 8.60 (1H, s), 9.20 (1H, s); m/z MH⁺ 379.

REFERENCES

An J et al. DNA-PKcs plays a dominant role in the regulation of H2AX phosphorylation in response to DNA damage and cell cycle progression. BMC Mol Biol 2010; 11: 18

Ashley A K. DNA-PK phosphorylation of RPA32 Ser4/Ser8 regulates replication stress checkpoint activation, fork restart, homologous recombination and mitotic catastrophe. DNA Repair 2014; 21: 131-139

Buisson R et al. Distinct but concerted roles of ATR, DNA-PK and Chk1 in countering replication stress during S phase. Molecular Cell 2015; 59: 1011-1024

Chan D W et al. Autophosphorylation of the DNA-dependent protein kinase catalytic subunit is required for rejoining of DNA double-strand breaks. Genes Dev 2002; 16: 2333-2338

Ciszewski W M et al. DNA-PK inhibition by NU7441 sensitizes breast cancer cells to ionizing radiation and doxorubicin. Breast Cancer Res Treat 2014; 143: 47-55

Deitlein F et al. A functional cancer genomics screen identifies a druggable synthetic lethal interaction between MSH3 and PRKDC. Cancer Discovery 2014; 4: 592-605

Douglas P et al. Identification of in vitro and in vivo phosphorylation sites in the catalytic subunit of the DNA dependent protein kinase. Biochem J 2002; 368: 243-251

Escribano-Diaz C. et al. A cell cycle dependent regulatory circuit composed of 53BP1-RIF1 and BRCA1-CtIP controls DNA repair pathway choice. Mol Cell 2013; 49: 872-883

Goodwin J F and Knudsen K E. Beyond DNA repair: DNA-PK function in cancer. Cancer Discovery 2014; 4: 1126-1139

Goodwin J F et al. A hormone-DNA repair circuit governs the response to genotoxic insult. Cancer Discovery 2013; 3: 1254-1271

Hartlerode A J and Scully R. Mechanisms of double-strand break repair in somatic mammalian cells. Biochem J 2009; 423: 157-168

Lin Y-F et al. DNA-PKcs is required to maintain stability of Chk1 and claspin for optimal replication stress response. Nucleic Acids Res 2014; 42: 4463-4473

Medunjanin S et al. Interaction of the double strand break repair kinase DNA-PK and estrogen receptor alpha. Mol Biol Cell 2010; 21: 1620-1628

Munck J M et al. Chemosensitization of cancer cells by KU-0060648, a dual inhibitor of DNA-PK and PI-3K. Mol Cancer Ther 2012; 11: 1789-1798

Neal J A and Meek K. Choosing the right path: does DNA-PK help make the decision? Mutat Res 2011; 711: 73-86

Riabinska A et al. Therapeutic targeting of a robust non-oncogene addiction to PRKDC in ATM-defective tumors. Science Translational Medicine 2013; 189: 189ra78

San Filippo J et al. Mechanism of ukaryotic homologous recombination. Annu Rev Biochem 2008; 77: 229-257

Smith G C M and Jackson S P. The DNA dependent protein kinase. Genes and Development 1999; 13: 916-934

Symington L S and Gautier J. Double strand break end resection and repair pathway choice. Annu Rev Genet 2011; 45: 247-271

Willmore E et al. A novel DNA-dependent protein kinase inhibitor, NU7026, potentiates the cytotoxicity of topoisomerase II poisons used in the treatment of leukemia Blood 2004; 103: 4659-4665

Yoo S and Dynan W S. Geometry of a complex formed by double strand break repair proteins at a single DNA end: recruitment of DNA-PKcs induces inward translocation of Ku protein. Nucleic Acids Res 1999; 27: 4679-4686

The invention claimed is:

1. A method for treating cancer in a warm-blooded animal in need of such treatment, which comprises administering to the warm-blooded animal a therapeutically effective amount of a compound of Formula (I):

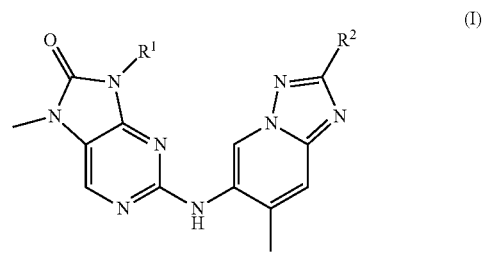

or a pharmaceutically acceptable salt thereof, wherein:

$R^1$ is a cyclohexyl, tetrahydrofuranyl or oxanyl ring, each of which is optionally substituted by one or more groups selected from hydroxyl, methoxy and methyl; and $R^2$ is hydrogen or methyl; and wherein the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer, non-small cell lung cancer, and sarcomas.

2. The method of claim 1, wherein $R^1$ is oxanyl.

3. The method of claim 2, wherein $R^1$ is oxan-4-yl.

4. The method of claim 1, wherein $R^1$ is cyclohexyl.

5. The method of claim 1, wherein $R^1$ is 1-hydroxy-1-methyl-cyclohex-4-yl.

6. The method of claim 1, wherein $R^2$ is hydrogen.

7. The method of claim 1, wherein the compound is selected from the group consisting of:

9-((1r,4r)-4-hydroxycyclohexyl)-7-methyl-2-((7-methyl-[1,2,4]triazolo[1,5-a]pyridin-6-yl)amino)-7,9-dihydro-8H-purin-8-one;

9-((1s,4s)-4-hydroxycyclohexyl)-7-methyl-2-((7-methyl-[1,2,4]triazolo[1,5-a]pyridin-6-yl)amino)-7,9-dihydro-8H-purin-8-one;

7-methyl-2-((7-methyl-[1,2,4]triazolo[1,5-a]pyridin-6-yl)amino)-9-(tetrahydro-2H-pyran-4-yl)-7,9-dihydro-8H-purin-8-one;

2-((2,7-dimethyl-[1,2,4]triazolo[1,5-a]pyridin-6-yl)amino)-7-methyl-9-(tetrahydro-2H-pyran-4-yl)-7,9-dihydro-8H-purin-8-one;

9-((1s,4s)-4-methoxycyclohexyl)-7-methyl-2-((7-methyl-[1,2,4]triazolo[1,5-a]pyridin-6-yl)amino)-7,9-dihydro-8H-purin-8-one;

9-((1r,4r)-4-methoxycyclohexyl)-7-methyl-2-((7-methyl-[1,2,4]triazolo[1,5-a]pyridin-6-yl)amino)-7,9-dihydro-8H-purin-8-one;

(S)-7-methyl-2-((7-methyl-[1,2,4]triazolo[1,5-a]pyridin-6-yl)amino)-9-(tetrahydro-2H-pyran-3-yl)-7,9-dihydro-8H-purin-8-one;

(R)-7-methyl-2-((7-methyl-[1,2,4]triazolo[1,5-a]pyridin-6-yl)amino)-9-(tetrahydro-2H-pyran-3-yl)-7,9-dihydro-8H-purin-8-one;

9-((1r,4r)-4-hydroxy-4-methylcyclohexyl)-7-methyl-2-((7-methyl-[1,2,4]triazolo[1,5-a]pyridin-6-yl)amino)-7,9-dihydro-8H-purin-8-one;

9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one;

(S)-7-methyl-2-((7-methyl-[1,2,4]triazolo[1,5-a]pyridin-6-yl)amino)-9-(tetrahydrofuran-3-yl)-7,9-dihydro-8H-purin-8-one;

9-((1s,4s)-4-hydroxy-1-methylcyclohexyl)-7-methyl-2-((7-methyl-[1,2,4]triazolo[1,5-a]pyridin-6-yl)amino)-7,9-dihydro-8H-purin-8-one; and 9-cyclohexyl-7-methyl-2-((7-methyl-[1,2,4]triazolo[1,5-a]pyridin-6-yl)amino)-7,9-dihydro-8H-purin-8-one.

8. The method of claim 1, wherein the compound is selected from the group consisting of:

7-methyl-2-((7-methyl-[1,2,4]triazolo[1,5-a]pyridin-6-yl)amino)-9-(tetrahydro-2H-pyran-4-yl)-7,9-dihydro-8H-purin-8-one;

9-((1r,4r)-4-hydroxy-4-methylcyclohexyl)-7-methyl-2-((7-methyl-[1,2,4]triazolo[1,5-a]pyridin-6-yl)amino)-7,9-dihydro-8H-purin-8-one; and 9-((1s,4s)-4-hydroxy-4-methylcyclohexyl)-7-methyl-2-((7-methyl-[1,2,4]triazolo[1,5-a]pyridin-6-yl)amino)-7,9-dihydro-8H-purin-8-one.

9. The method of claim 1, wherein the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer and non-small cell lung cancer.

10. A method for treating cancer in a warm-blooded animal in need of such treatment, which comprises administering to the warm-blooded animal a therapeutically effective amount of 7-methyl-2-((7-methyl-[1,2,4]triazolo[1,5-a]pyridin-6-yl)amino)-9-(tetrahydro-2H-pyran-4-yl)-7,9-dihydro-8H-purin-8-one, or a pharmaceutically acceptable salt thereof; wherein the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer, non-small cell lung cancer, and sarcomas.

11. The method of claim 10, wherein 7-methyl-2-((7-methyl-[1,2,4]triazolo[1,5-a]pyridin-6-yl)amino)-9-(tetrahydro-2H-pyran-4-yl)-7,9-dihydro-8H-purin-8-one is administered to the warm-blooded animal.

12. The method of claim 10, wherein a pharmaceutically acceptable salt of 7-methyl-2-((7-methyl-[1,2,4]triazolo[1,5-a]pyridin-6-yl)amino)-9-(tetrahydro-2H-pyran-4-yl)-7,9-dihydro-8H-purin-8-one is administered to the warm-blooded animal.

13. The method of claim 10, wherein the warm-blooded animal is a human.

14. The method of claim 13, wherein the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, small cell lung cancer and non-small cell lung cancer.

15. The method of claim 13, wherein the cancer is ovarian cancer.

16. The method of claim 13, wherein the cancer is breast cancer.

17. The method of claim 13, wherein the cancer is non-small cell lung cancer.

18. The method of claim 13, wherein the cancer is head and neck squamous cell carcinoma.

19. The method of claim 13, wherein the method further comprises administering radiotherapy to the human.

20. The method of claim 13, wherein the method further comprises administering to the human at least one additional anti-tumour substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, durvalumab, AZD1775, AZD6738, AZD1390, and AZD0156.

21. The method of claim 13, wherein the method further comprises administering a PARP inhibitor to the human.

22. The method of claim 13, wherein the method further comprises administering olaparib to the human.

23. The method of claim 13, wherein the method further comprises administering doxorubicin to the human.

24. The method of claim 13, wherein the method further comprises administering liposomal doxorubicin to the human.

25. The method of claim 1, wherein the cancer is a sarcoma.

26. The method of claim 25, wherein the sarcoma is selected from the group consisting of osteosarcoma, chondrosarcoma, leiomyosarcoma, soft tissue sarcoma, and Ewing's sarcoma.

27. The method of claim 10, wherein the cancer is a sarcoma.

28. The method of claim 27, wherein the sarcoma is selected from the group consisting of osteosarcoma, chondrosarcoma, leiomyosarcoma, soft tissue sarcoma, and Ewing's sarcoma.

* * * * *